(12) United States Patent
Qian et al.

(10) Patent No.: US 12,358,994 B2
(45) Date of Patent: Jul. 15, 2025

(54) ANTIBODY-MODIFIED CHIMERIC ANTIGEN RECEPTOR MODIFIED T CELL AND USES THEREOF

(71) Applicant: Shanghai Cell Therapy Group Co., Ltd., Shanghai (CN)

(72) Inventors: Qijun Qian, Shanghai (CN); Huajun Jin, Shanghai (CN); Duqing Jiang, Shanghai (CN); Zhou He, Shanghai (CN); Shumei You, Shanghai (CN); Xi Tang, Shanghai (CN); Linfang Li, Shanghai (CN); Chao Wang, Shanghai (CN); Lianzhen Cui, Shanghai (CN)

(73) Assignee: SHANGHAI CELL THERAPY GROUP CO., LTD., Shanghai (CN)

( * ) Notice: Subject to any disclaimer, the term of this patent is extended or adjusted under 35 U.S.C. 154(b) by 1417 days.

(21) Appl. No.: 16/958,630

(22) PCT Filed: Dec. 28, 2018

(86) PCT No.: PCT/CN2018/124692
§ 371 (c)(1),
(2) Date: Jan. 25, 2021

(87) PCT Pub. No.: WO2019/129177
PCT Pub. Date: Jul. 4, 2019

(65) Prior Publication Data
US 2021/0155702 A1 May 27, 2021

(30) Foreign Application Priority Data
Dec. 28, 2017 (CN) .......................... 201711462801.X

(51) Int. Cl.
| | | |
|---|---|---|
| A61K 35/17 | (2025.01) | |
| A61K 40/11 | (2025.01) | |
| A61K 40/31 | (2025.01) | |
| A61K 40/42 | (2025.01) | |
| A61P 35/00 | (2006.01) | |
| C07K 14/705 | (2006.01) | |
| C07K 16/18 | (2006.01) | |
| C07K 16/28 | (2006.01) | |
| C12N 5/0783 | (2010.01) | |
| A61K 39/00 | (2006.01) | |

(52) U.S. Cl.
CPC .......... *C07K 16/2878* (2013.01); *A61K 40/11* (2025.01); *A61K 40/31* (2025.01); *A61K 40/4204* (2025.01); *A61K 40/4211* (2025.01); *A61K 40/4255* (2025.01); *A61K 40/4257* (2025.01); *A61P 35/00* (2018.01); *C07K 14/70503* (2013.01); *C07K 14/70578* (2013.01); *C07K 16/18* (2013.01); *C07K 16/2803* (2013.01); *C07K 16/2809* (2013.01); *C07K 16/2812* (2013.01); *C07K 16/2815* (2013.01); *C07K 16/2818* (2013.01); *C07K 16/2863* (2013.01); *C12N 5/0636* (2013.01); *A61K 2039/505* (2013.01); *A61K 2239/31* (2023.05); *A61K 2239/38* (2023.05); *A61K 2239/48* (2023.05); *A61K 2239/55* (2023.05); *A61K 2239/59* (2023.05); *C07K 2317/524* (2013.01); *C07K 2317/526* (2013.01); *C07K 2317/53* (2013.01); *C07K 2317/622* (2013.01); *C07K 2317/75* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search
CPC ....................................................... A61K 35/17
See application file for complete search history.

(56) References Cited

U.S. PATENT DOCUMENTS

| | | | |
|---|---|---|---|
| 8,568,725 B2 | 10/2013 | Nobuaki et al. | |
| 2016/0376328 A1 | 12/2016 | Poma et al. | |

FOREIGN PATENT DOCUMENTS

| | | | | |
|---|---|---|---|---|
| CN | 1922316 A | * | 2/2007 | ....... A61K 39/39533 |
| CN | 105950561 A | | 9/2016 | |
| CN | 106414503 A | | 2/2017 | |
| CN | 107034235 A | * | 8/2017 | |
| CN | 107074957 | | 8/2017 | |
| JP | 2016-508728 | | 3/2016 | |
| WO | WO2014134165 | | 9/2014 | |
| WO | WO2015001085 | | 1/2015 | |
| WO | WO-2015/105522 | | 7/2015 | |

(Continued)

OTHER PUBLICATIONS

Maus et al. (2014, Blood, vol. 123(17), pp. 2625-2635). (Year: 2014).*

(Continued)

*Primary Examiner* — Anoop K Singh
*Assistant Examiner* — David A Montanari
(74) *Attorney, Agent, or Firm* — MORRISON & FOERSTER LLP

(57) ABSTRACT

The invention relates to a T cell expressing an antibody or comprising the coding sequence of the antibody or an expression vector thereof; the antibody contains an optional signal peptide, an antigen binding sequence and a mutant type Fc segment, wherein the mutant type Fc segment is a Fc segment in which amino acid residues at the 17th site and the 79th site of the IgG4 Fc segment shown by SEQ ID NO: 25 are mutated into E and Q respectively. Preferably, the T cell is a CAR-T cell. The present invention further relates to a treatment application of the T cell in malignant tumors.

13 Claims, 29 Drawing Sheets
Specification includes a Sequence Listing.

(56) References Cited

FOREIGN PATENT DOCUMENTS

| WO | WO2017136829 | 8/2017 |
| WO | WO2017165683 | 9/2017 |
| WO | WO2017219937 | 12/2017 |

OTHER PUBLICATIONS

Curran et al., "Enhancing Antitumor Efficacy of Chimeric Antigen Receptor T cells Through Constitutive CD40L Expression," Molecular Therapy (2015) 23(4) 769-778.
Jonnalagadda et al., "Chimeric Antigen Receptors With Mutated IgG4 Fc Spacer Avoid Fc Receptor Binding and Improve T Cell Persistence and Antitumor Efficacy," Molecular Therapy (2014) 23(4):757-768.
Supplementary European Search Report for EP 18893977.1, mailed Aug. 30, 2021, 14 pages.
International Search Report mailed Mar. 27, 2019, directed to International Application No. PCT/CN2018/124692; 9 pages.
Li et al., "Enhanced Cancer Immunotherapy by Chimeric Antigen Receptor-Modified T Cells Engineered to Secrete Checkpoint Inhibitors," Clinical cancer research (2017), 23(22): 6982-6992.
Wang et al., "IgG Fc engineering to modulate antibody effector functions," Protein & cell (2018), 9(1): 63-73.

\* cited by examiner

```
SEQUENCE LISTING

<160> NUMBER OF SEQ ID NOS: 25

<210> SEQ ID NO 1
<211> LENGTH: 497
<212> TYPE: PRT
<213> ORGANISM: Artificial Sequence
<220> FEATURE:
<223> OTHER INFORMATION: Description of Artificial Sequence: amino acid
      sequence of mutant anti-CD40 antibody

<400> SEQUENCE: 1

Met Glu Ala Pro Ala Gln Leu Leu Phe Leu Leu Leu Trp Leu Pro
1               5                   10                  15

Asp Thr Thr Gly Gln Val Gln Leu Val Gln Ser Gly Ala Glu Val Lys
                20                  25                  30

Lys Pro Gly Ala Ser Val Lys Val Ser Cys Lys Ala Ser Gly Tyr Thr
            35                  40                  45

Phe Thr Gly Tyr Tyr Met His Trp Val Arg Gln Ala Pro Gly Gln Gly
        50                  55                  60

Leu Glu Trp Met Gly Trp Ile Asn Pro Asp Ser Gly Gly Thr Asn Tyr
65                  70                  75                  80

Ala Gln Lys Phe Gln Gly Arg Val Thr Met Thr Arg Asp Thr Ser Ile
                85                  90                  95

Ser Thr Ala Tyr Met Glu Leu Asn Arg Leu Arg Ser Asp Asp Thr Ala
            100                 105                 110

Val Tyr Tyr Cys Ala Arg Asp Gln Pro Leu Gly Tyr Cys Thr Asn Gly
        115                 120                 125

Val Cys Ser Tyr Phe Asp Tyr Trp Gly Gln Gly Thr Leu Val Thr Val
    130                 135                 140

Ser Ser Gly Gly Gly Ser Gly Gly Gly Ser Gly Gly Gly Gly
145                 150                 155                 160

Ser Asp Ile Gln Met Thr Gln Ser Pro Ser Ser Val Ser Ala Ser Val
                165                 170                 175

Gly Asp Arg Val Thr Ile Thr Cys Arg Ala Ser Gln Gly Ile Tyr Ser
            180                 185                 190

Trp Leu Ala Trp Tyr Gln Gln Lys Pro Gly Lys Ala Pro Asn Leu Leu
        195                 200                 205

Ile Tyr Thr Ala Ser Thr Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240
```

Pro Glu Asp Phe Ala Thr Tyr Tyr Cys Gln Gln Ala Asn Ile Phe Pro
                245                 250                 255

Leu Thr Phe Gly Gly Gly Thr Lys Val Glu Ile Lys Glu Ser Lys Tyr
            260                 265                 270

Gly Pro Pro Cys Pro Pro Cys Pro Ala Pro Glu Phe Glu Gly Gly Pro
                275                 280                 285

Ser Val Phe Leu Phe Pro Pro Lys Pro Lys Asp Thr Leu Met Ile Ser
290                 295                 300

Arg Thr Pro Glu Val Thr Cys Val Val Val Asp Val Ser Gln Glu Asp
305                 310                 315                 320

Pro Glu Val Gln Phe Asn Trp Tyr Val Asp Gly Val Glu Val His Asn
                325                 330                 335

Ala Lys Thr Lys Pro Arg Glu Glu Gln Phe Gln Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Gly Leu Pro Ser Ser Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Arg Leu Thr Val Asp Lys
    450                 455                 460

Ser Arg Trp Gln Glu Gly Asn Val Phe Ser Cys Ser Val Met His Glu
465                 470                 475                 480

Ala Leu His Asn His Tyr Thr Gln Lys Ser Leu Ser Leu Ser Leu Gly
                485                 490                 495

Lys

<210> SEQ ID NO 2
<211> LENGTH: 1491
<212> TYPE: DNA
<213> ORGANISM: Artificial Sequence
<220> FEATURE:
<223> OTHER INFORMATION: Description of Artificial Sequence: nucleotide
      sequence of mutant anti-CD40 antibody

<400> SEQUENCE: 2
atggaagccc cagctcagct tctcttcctc ctgctactct ggctcccaga taccaccgga      60
caggtgcagc tggtgcagtc tggggctgag gtgaagaagc ctggggcctc agtgaaggtc     120
tcctgcaagg cttctggata caccttcacc ggctactata tgcactgggt gcgacaggcc     180
cctggacaag gcttgagtg gatgggatgg atcaaccctg acagtggtgg cacaaactat     240
gcacagaagt tcagggcag gtcaccatg accaggaca cgtccatcag cacagcctac       300
atggagctga acaggctgag atctgacgac acggccgtgt attactgtgc gagagatcag     360
cccctaggat attgtactaa tggtgtatgc tcctactttg actactgggg ccagggaacc     420
ctggtcaccg tctcctcagg tgaggcggt tcaggcggag gtggcagcgg cggtggcggg      480
tcggacatcc agatgaccca gtctccatct tccgtgtctg catctgtagg agacagagtc     540

```
accatcactt gtcgggcgag tcagggtatt tacagctggt tagcctggta tcagcagaaa      600
ccagggaaag cccctaacct cctgatctat actgcatcca ctttacaaag tggggtccca      660
tcaaggttca gcggcagtgg atctgggaca gatttcactc tcaccatcag cagcctgcaa      720
cctgaagatt ttgcaactta ctattgtcaa caggctaaca ttttcccgct cactttcggc      780
ggagggacca aggtggagat caaagagtcc aaatatggtc ccccatgccc accatgccca      840
gcacctgagt tcgagggggg accatcagtc ttcctgttcc ccccaaaacc caaggacact      900
ctcatgatct cccggacccc tgaggtcacg tgcgtggtgg tggacgtgag ccaggaagac      960
cccgaggtcc agttcaactg gtacgtggat ggcgtggagg tgcataatgc caagacaaag     1020
ccgcgggagg agcagttcca gagcacgtac cgtgtggtca gcgtcctcac cgtcctgcac     1080
caggactggc tgaacggcaa ggagtacaag tgcaaggtct ccaacaaagg cctcccgtcc     1140
tccatcgaga aaaccatctc caaagccaaa gggcagcccc gagagccaca ggtgtacacc     1200
ctgcccccat cccaggagga gatgaccaag aaccaggtca gcctgacctg cctggtcaaa     1260
ggcttctacc ccagcgacat cgccgtggag tgggagagca atgggcagcc ggagaacaac     1320
tacaagacca cgcctcccgt gctggactcc gacggctcct tcttcctcta cagcaggcta     1380
accgtggaca agagcaggtg gcaggagggg aatgtcttct catgctccgt gatgcatgag     1440
gctctgcaca accactacac acagaagagc ctctccctgt ctctgggtaa a              1491
```

<210> SEQ ID NO 3
<211> LENGTH: 495
<212> TYPE: PRT
<213> ORGANISM: Artificial Sequence
<220> FEATURE:
<223> OTHER INFORMATION: Description of Artificial Sequence: amino acid
      sequence of mutant anti-PD-1 antibody

<400> SEQUENCE: 3

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Lys Gly
        35                  40                  45

Val Ser Thr Ser Gly Tyr Ser Tyr Leu His Trp Tyr Gln Gln Lys Pro
    50                  55                  60

Gly Gln Ala Pro Arg Leu Leu Ile Tyr Leu Ala Ser Tyr Leu Glu Ser
65                  70                  75                  80

Gly Val Pro Ala Arg Phe Ser Gly Ser Gly Ser Gly Thr Asp Phe Thr
                85                  90                  95

Leu Thr Ile Ser Ser Leu Glu Pro Glu Asp Phe Ala Val Tyr Tyr Cys
            100                 105                 110

Gln His Ser Arg Asp Leu Pro Leu Thr Phe Gly Gly Gly Thr Lys Val
        115                 120                 125

Glu Ile Lys Gly Gly Gly Gly Ser Gly Gly Gly Gly Ser Gly Gly Gly
    130                 135                 140

Gly Ser Gln Val Gln Leu Val Gln Ser Gly Val Glu Val Lys Lys Pro
145                 150                 155                 160

Gly Ala Ser Val Lys Val Ser Cys Lys Ala Ser Gly Tyr Thr Phe Thr
                165                 170                 175

Asn Tyr Tyr Met Tyr Trp Val Arg Gln Ala Pro Gly Gln Gly Leu Glu
            180                 185                 190
```

Trp Met Gly Gly Ile Asn Pro Ser Asn Gly Thr Asn Phe Asn Glu
            195                 200                 205

Lys Phe Lys Asn Arg Val Thr Leu Thr Thr Asp Ser Thr Thr Thr
210                 215                 220

Ala Tyr Met Glu Leu Lys Ser Leu Gln Phe Asp Thr Ala Val Tyr
225                 230                 235                 240

Tyr Cys Ala Arg Arg Asp Tyr Arg Phe Asp Met Gly Phe Asp Tyr Trp
                245                 250                 255

Gly Gln Gly Thr Thr Val Thr Val Ser Ser Glu Ser Lys Tyr Gly Pro
                260                 265                 270

Pro Cys Pro Pro Cys Pro Ala Pro Glu Phe Glu Gly Gly Pro Ser Val
                275                 280                 285

Phe Leu Phe Pro Pro Lys Pro Lys Asp Thr Leu Met Ile Ser Arg Thr
290                 295                 300

Pro Glu Val Thr Cys Val Val Val Asp Val Ser Gln Glu Asp Pro Glu
305                 310                 315                 320

Val Gln Phe Asn Trp Tyr Val Asp Gly Val Glu Val His Asn Ala Lys
                325                 330                 335

Thr Lys Pro Arg Glu Glu Gln Phe Gln Ser Thr Tyr Arg Val Val Ser
                340                 345                 350

Val Leu Thr Val Leu His Gln Asp Trp Leu Asn Gly Lys Glu Tyr Lys
                355                 360                 365

Cys Lys Val Ser Asn Lys Gly Leu Pro Ser Ser Ile Glu Lys Thr Ile
                370                 375                 380

Ser Lys Ala Lys Gly Gln Pro Arg Glu Pro Gln Val Tyr Thr Leu Pro
385                 390                 395                 400

Pro Ser Gln Glu Glu Met Thr Lys Asn Gln Val Ser Leu Thr Cys Leu
                405                 410                 415

Val Lys Gly Phe Tyr Pro Ser Asp Ile Ala Val Glu Trp Glu Ser Asn
                420                 425                 430

Gly Gln Pro Glu Asn Asn Tyr Lys Thr Thr Pro Pro Val Leu Asp Ser
                435                 440                 445

Asp Gly Ser Phe Phe Leu Tyr Ser Arg Leu Thr Val Asp Lys Ser Arg
450                 455                 460

Trp Gln Glu Gly Asn Val Phe Ser Cys Ser Val Met His Glu Ala Leu
465                 470                 475                 480

His Asn His Tyr Thr Gln Lys Ser Leu Ser Leu Ser Leu Gly Lys
                485                 490                 495

<210> SEQ ID NO 4
<211> LENGTH: 1488
<212> TYPE: DNA
<213> ORGANISM: Artificial Sequence
<220> FEATURE:
<223> OTHER INFORMATION: Description of Artificial Sequence: nucleotide
      sequence of mutant anti-PD-1 antibody

<400> SEQUENCE: 4
atggaagccc agctcagct tctcttcctc ctgctactct ggctcccaga taccaccgga      60
gaaattgtgt tgacacagtc tccagccacc ctgtctttgt ctccagggga aagagccacc    120
ctctcctgca gggccagcaa aggtgtcagt acatctggct atagttattt gcactggtat    180
caacagaaac ctggccaggc tcccaggctc ctcatctatc ttgcatccta cctagaatct    240
ggcgtcccag ccaggttcag tggtagtggg tctgggacag acttcactct caccatcagc    300

-continued

```
agcctagagc ctgaagattt tgcagtttat tactgtcagc acagcaggga ccttccgctc      360
acgttcggcg agggaccaa  agtggagatc aaaggtggag gcggttcagg cggaggtggc      420
agcggcggtg gcgggtcgca ggtgcagctg gtgcagtccg gcgtggaggt gaagaagcct      480
ggcgcctccg tcaaggtgtc ctgtaaggcc tccggctaca ccttcaccaa ctactacatg      540
tactgggtgc ggcaggcccc aggccaggga ctggagtgga tgggcggcat caacccttcc      600
aacggcggca ccaacttcaa cgagaagttc aagaaccggg tgaccctgac cacccactcc      660
tccaccacaa ccgcctacat ggaactgaag tccctgcagt cgacgacac  cgccgtgtac      720
tactgcgcca gcgggacta  ccggttcgac atgggcttcg actactgggg ccagggcacc      780
accgtgaccg tgtcctccga gtccaaatat ggtcccccat gcccaccatg cccagcacct      840
gagttcgagg ggggaccatc agtcttcctg ttccccccaa acccaagga  cactctcatg      900
atctcccgga cccctgaggt cacgtgcgtg gtggtggacg tgagccagga agaccccgag      960
gtccagttca actggtacgt ggatggcgtg gaggtgcata atgccaagac aaagccgcgg     1020
gaggagcagt tccagagcac gtaccgtgtg gtcagcgtcc tcaccgtcct gcaccaggac     1080
tggctgaacg gcaaggagta caagtgcaag gtctccaaca aaggcctccc gtcctccatc     1140
gagaaaacca tctccaaagc caaagggcag ccccgagagc cacaggtgta caccctgccc     1200
ccatcccagg aggagatgac caagaaccag gtcagcctga cctgcctggt caaaggcttc     1260
taccccagcg acatcgccgt ggagtgggag agcaatgggc agccggagaa caactacaag     1320
accacgcctc ccgtgctgga ctccgacggc tccttcttcc tctacagcag gctaaccgtg     1380
gacaagagca ggtggcagga ggggaatgtc ttctcatgct ccgtgatgca tgaggctctg     1440
cacaaccact acacacagaa gagcctctcc ctgtctctgg gtaaatga                  1488
```

<210> SEQ ID NO 5
<211> LENGTH: 367
<212> TYPE: PRT
<213> ORGANISM: Artificial Sequence
<220> FEATURE:
<223> OTHER INFORMATION: Description of Artificial Sequence: amino acid sequence of anti-CD47 antibody

<400> SEQUENCE: 5

```
Met Glu Ala Pro Ala Gln Leu Leu Phe Leu Leu Leu Leu Trp Leu Pro
1               5                   10                  15

Asp Thr Thr Gly Glu Glu Leu Gln Ile Ile Gln Pro Asp Lys Ser
            20                  25                  30

Val Leu Val Ala Ala Gly Glu Thr Ala Thr Leu Arg Cys Thr Ile Thr
        35                  40                  45

Ser Leu Phe Pro Val Gly Pro Ile Gln Trp Phe Arg Gly Ala Gly Pro
    50                  55                  60

Gly Arg Val Leu Ile Tyr Asn Gln Arg Gln Gly Pro Phe Pro Arg Val
65                  70                  75                  80

Thr Thr Val Ser Asp Thr Thr Lys Arg Asn Asn Met Asp Phe Ser Ile
                85                  90                  95

Arg Ile Gly Asn Ile Thr Pro Ala Asp Ala Gly Thr Tyr Tyr Cys Ile
            100                 105                 110

Lys Phe Arg Lys Gly Ser Pro Asp Asp Val Glu Phe Lys Ser Gly Ala
        115                 120                 125

Gly Thr Glu Leu Ser Val Arg Ala Lys Pro Glu Ser Lys Tyr Gly Pro
    130                 135                 140

Pro Cys Pro Pro Cys Pro Ala Pro Glu Phe Glu Gly Gly Pro Ser Val
```

| | | | | 145 | | | | 150 | | | | 155 | | | | 160 |

Phe Leu Phe Pro Pro Lys Pro Lys Asp Thr Leu Met Ile Ser Arg Thr
              165                      170                    175

Pro Glu Val Thr Cys Val Val Val Asp Val Ser Gln Glu Asp Pro Glu
            180                      185                    190

Val Gln Phe Asn Trp Tyr Val Asp Gly Val Glu Val His Asn Ala Lys
              195                    200                  205

Thr Lys Pro Arg Glu Glu Gln Phe Gln Ser Thr Tyr Arg Val Val Ser
    210                      215                    220

Val Leu Thr Val Leu His Gln Asp Trp Leu Asn Gly Lys Glu Tyr Lys
225                    230                    235                240

Cys Lys Val Ser Asn Lys Gly Leu Pro Ser Ser Ile Glu Lys Thr Ile
            245                      250                    255

Ser Lys Ala Lys Gly Gln Pro Arg Glu Pro Gln Val Tyr Thr Leu Pro
            260                      265                  270

Pro Ser Gln Glu Glu Met Thr Lys Asn Gln Val Ser Leu Thr Cys Leu
              275                    280                  285

Val Lys Gly Phe Tyr Pro Ser Asp Ile Ala Val Glu Trp Glu Ser Asn
    290                      295                    300

Gly Gln Pro Glu Asn Asn Tyr Lys Thr Thr Pro Pro Val Leu Asp Ser
305                    310                    315                320

Asp Gly Ser Phe Phe Leu Tyr Ser Arg Leu Thr Val Asp Lys Ser Arg
              325                    330                  335

Trp Gln Glu Gly Asn Val Phe Ser Cys Ser Val Met His Glu Ala Leu
            340                      345                  350

His Asn His Tyr Thr Gln Lys Ser Leu Ser Leu Ser Leu Gly Lys
              355                    360                  365

<210> SEQ ID NO 6
<211> LENGTH: 1104
<212> TYPE: DNA
<213> ORGANISM: Artificial Sequence
<220> FEATURE:
<223> OTHER INFORMATION: Description of Artificial Sequence: nucleotide
     sequence of anti-CD47 antibody

<400> SEQUENCE: 6

```
atggaagccc cagctcagct tctcttcctc ctgctactct ggctcccaga taccaccgga      60
gaggaggagc tgcagatcat tcagcctgac aagtccgtgt tggttgcagc tggagagaca     120
gccactctgc gctgcactat cacctctctg ttccctgtgg ggcccatcca gtggttcaga     180
ggagctggac caggccgggt gttaatctac aatcaaagac agggccccct ccccgggta     240
acaactgttt cagacaccac aaagagaaac aacatggact tttccatccg catcggtaac     300
atcaccccag cagatgccgg cacctactac tgtatcaagt ccggaaaagg agccccgat     360
gacgtggagt ttaagtctgg agcaggcact gagctgtctg tgcgcgccaa cccgagtcc     420
aaatatggtc cccatgcccc accatgccca gcacctgagt cgaggggggg accatcagtc     480
ttcctgttcc cccaaaacc caaggacact ctcatgatct cccggacccc tgaggtcacg     540
tgcgtggtgg tggacgtgag ccaggaagac cccgaggtcc agttcaactg gtacgtggat     600
ggcgtggagg tgcataatgc caagacaaag ccgcgggagg agcagttcca gagcacgtac     660
cgtgtggtca gcgtcctcac cgtcctgcac caggactggc tgaacggcaa ggagtacaag     720
tgcaaggtct ccaacaaagg cctcccgtcc tccatcgaga aaaccatctc aaagccaaa     780
gggcagcccc gagagccaca ggtgtacacc ctgcccccat cccaggagga gatgaccaag     840
```

```
aaccaggtca gcctgacctg cctggtcaaa ggcttctacc ccagcgacat cgccgtggag    900
tgggagagca atgggcagcc ggagaacaac tacaagacca cgcctccgt gctggactcc    960 gacggctcct tcttcctcta cagcaggcta accgtggaca gagcaggtg gcaggagggg   1020 aatgtcttct catgctccgt gatgcatgag gctctgcaca accactacac acagaagagc   1080
ctctccctgt ctctgggtaa atga                                          1104
```

<210> SEQ ID NO 7
<211> LENGTH: 486
<212> TYPE: PRT
<213> ORGANISM: Artificial Sequence
<220> FEATURE:
<223> OTHER INFORMATION: Description of Artificial Sequence: amino acid
sequence of CD19CAR

<400> SEQUENCE: 7

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300
```

```
Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
        340                 345                 350

Thr Thr Gln Glu Glu Asp Gly Cys Ser Cys Arg Phe Pro Glu Glu Glu
    355                 360                 365

Glu Gly Gly Cys Glu Leu Arg Val Lys Phe Ser Arg Ser Ala Asp Ala
370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 8
<211> LENGTH: 1461
<212> TYPE: DNA
<213> ORGANISM: Artificial Sequence
<220> FEATURE:
<223> OTHER INFORMATION: Description of Artificial Sequence: nucleotide
      sequence of CD19CAR

<400> SEQUENCE: 8
atggccttac cagtgaccgc cttgctcctg ccgctggcct tgctgctcca cgccgccagg    60
ccggacatcc agatgacaca gactacatcc tccctgtctg cctctctggg agacagagtc   120
accatcagtt gcagggcaag tcaggacatt agtaaatatt taaattggta tcagcagaaa   180
ccagatggaa ctgttaaact cctgatctac catacatcaa gattacactc aggagtccca   240
tcaaggttca gtggcagtgg gtctggaaca gattattctc tcaccattag caacctggag   300
caagaagata ttgccactta cttttgccaa cagggtaata cgcttccgta cacgttcgga   360
gggggtggga actcagttcg gaaaaacagg aatctaactt aggcagctctc acactggtagt   420 ggcgggtcgg aggtgaaact gcaggagtca ggacctggcc tggtggcgcc ctcacagagc   480
ctgtccgtca catgcactgt ctcagggtc tcattacccg actatggtgt aagctggatt   540
cgccagcctc cacgaaaggg tctggagtgg ctgggagtaa tatgggggta gtgaaaccaca   600 tactataatt cagctctcaa atccagactg accatcatca aggacaactc caagagccaa   660
gttttcttaa aaatgaacag tctgcaaact gatgacacag ccatttacta ctgtgccaaa   720
cattattact acggtggtag ctatgctatg gactactggg gtcaaggaac ctcagtcacc   780
gtctcctcaa ccacgacgcc agcgccgcga ccaccaacac cggcgcccac catcgcgtcg   840
cagcccctgt ccctgcgccc agaggcgtgc cggccagcgg cgggggggcgc agtgcacacg   900 agggggctgg acttcgcctg tgatatctac atctgggcgc cctgggccgg gacttgtggg   960
```

-continued

```
gtccttctcc tgtcactggt tatcacccct tactgcaaac ggggcagaaa gaagctcctg    1020
tatatattca acaaccatt tatgagacca gtacaaacta ctcaagagga agatggctgt    1080
agctgccgat ttccagaaga agaagaagga ggatgtgaac tgagagtgaa gttcagcagg    1140
agcgcagacg ccccgcgta ccagcagggc cagaaccagc tctataacga gctcaatcta    1200
ggacgaagag aggagtacga tgttttggac aagagacgtg gccgggaccc tgagatgggg    1260
ggaaagccga aaggaagaa ccctcaggaa ggcctgtaca atgaactgca gaaagataag    1320
atggcggagg cctacagtga gattgggatg aaggcgagc gccggagggg caaggggcac    1380
gatggccttt accagggtct cagtacagcc accaaggaca cctacgacgc ccttcacatg    1440
caggccctgc cccctcgctg a                                             1461
```

<210> SEQ ID NO 9
<211> LENGTH: 681
<212> TYPE: PRT
<213> ORGANISM: Artificial Sequence
<220> FEATURE:
<223> OTHER INFORMATION: Description of Artificial Sequence: amino acid sequence of mesoCAR

<400> SEQUENCE: 9

```
Met Ala Leu Pro Val Thr Ala Leu Leu Leu Pro Leu Ala Leu Leu Leu
1               5                   10                  15

His Ala Ala Arg Pro Ser Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asp Leu Gly Phe Tyr Phe Tyr Ala Cys Trp Val Arg Gln Ala Pro
    50                  55                  60

Gly Lys Gly Leu Glu Trp Val Ser Cys Ile Tyr Thr Ala Gly Ser Gly
65                  70                  75                  80

Ser Thr Tyr Tyr Ala Ser Trp Ala Lys Gly Arg Phe Thr Ile Ser Arg
                85                  90                  95

Asp Asn Ser Lys Asn Thr Leu Tyr Leu Gln Met Asn Ser Leu Arg Ala
            100                 105                 110

Glu Asp Thr Ala Val Tyr Tyr Cys Ala Arg Ser Thr Ala Asn Thr Arg
        115                 120                 125

Ser Thr Tyr Tyr Leu Asn Leu Trp Gly Gln Gly Thr Leu Val Thr Val
    130                 135                 140

Ser Ser Gly Gly Gly Ser Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Gln Ala Ser Gln Arg Ile Ser Ser
            180                 185                 190

Tyr Leu Ser Trp Tyr Gln Gln Lys Pro Gly Lys Val Pro Lys Leu Leu
        195                 200                 205

Ile Tyr Gly Ala Ser Thr Leu Ala Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Val Ala Thr Tyr Tyr Cys Gln Ser Tyr Ala Tyr Phe Asp
                245                 250                 255

Ser Asn Asn Trp His Ala Phe Gly Gly Gly Thr Lys Val Glu Ile Lys
            260                 265                 270
```

```
Glu Ser Lys Tyr Gly Pro Pro Cys Pro Pro Cys Pro Ala Pro Pro Val
        275                 280                 285
Ala Gly Pro Ser Val Phe Leu Phe Pro Pro Lys Pro Lys Asp Thr Leu
    290                 295                 300
Met Ile Ser Arg Thr Pro Glu Val Thr Cys Val Val Val Asp Val Ser
305                 310                 315                 320
Gln Glu Asp Pro Glu Val Gln Phe Asn Trp Tyr Val Asp Gly Val Glu
                325                 330                 335
Val His Asn Ala Lys Thr Lys Pro Arg Glu Glu Gln Phe Gln Ser Thr
                340                 345                 350
Tyr Arg Val Val Ser Val Leu Thr Val Leu His Gln Asp Trp Leu Asn
                355                 360                 365
Gly Lys Glu Tyr Lys Cys Lys Val Ser Asn Lys Gly Leu Pro Ser Ser
        370                 375                 380
Ile Glu Lys Thr Ile Ser Lys Ala Lys Gly Gln Pro Arg Glu Pro Gln
385                 390                 395                 400
Val Tyr Thr Leu Pro Pro Ser Gln Glu Glu Met Thr Lys Asn Gln Val
                405                 410                 415
Ser Leu Thr Cys Leu Val Lys Gly Phe Tyr Pro Ser Asp Ile Ala Val
                420                 425                 430
Glu Trp Glu Ser Asn Gly Gln Pro Glu Asn Asn Tyr Lys Thr Thr Pro
        435                 440                 445
Pro Val Leu Asp Ser Asp Gly Ser Phe Phe Leu Tyr Ser Arg Leu Thr
        450                 455                 460
Val Asp Lys Ser Arg Trp Gln Glu Gly Asn Val Phe Ser Cys Ser Val
465                 470                 475                 480
Met His Glu Ala Leu His Asn His Tyr Thr Gln Lys Ser Leu Ser Leu
                485                 490                 495
Ser Leu Gly Lys Pro Phe Trp Val Leu Val Val Val Gly Gly Val Leu
                500                 505                 510
Ala Cys Tyr Ser Leu Leu Val Thr Val Ala Phe Ile Ile Phe Trp Val
        515                 520                 525
Arg Ser Lys Arg Ser Arg Leu Leu His Ser Asp Tyr Met Asn Met Thr
        530                 535                 540
Pro Arg Arg Pro Gly Pro Thr Arg Lys His Tyr Gln Pro Tyr Ala Pro
545                 550                 555                 560
Pro Arg Asp Phe Ala Ala Tyr Arg Ser Arg Val Lys Phe Ser Arg Ser
                565                 570                 575
Ala Asp Ala Pro Ala Tyr Gln Gln Gly Gln Asn Gln Leu Tyr Asn Glu
                580                 585                 590
Leu Asn Leu Gly Arg Arg Glu Glu Tyr Asp Val Leu Asp Lys Arg Arg
        595                 600                 605
Gly Arg Asp Pro Glu Met Gly Gly Lys Pro Arg Arg Lys Asn Pro Gln
        610                 615                 620
Glu Gly Leu Tyr Asn Glu Leu Gln Lys Asp Lys Met Ala Glu Ala Tyr
625                 630                 635                 640
Ser Glu Ile Gly Met Lys Gly Glu Arg Arg Gly Lys Gly His Asp
                645                 650                 655
Gly Leu Tyr Gln Gly Leu Ser Thr Ala Thr Lys Asp Thr Tyr Asp Ala
                660                 665                 670
Leu His Met Gln Ala Leu Pro Pro Arg
        675                 680
```

<210> SEQ ID NO 10
<211> LENGTH: 2043
<212> TYPE: DNA
<213> ORGANISM: Artificial Sequence
<220> FEATURE:
<223> OTHER INFORMATION: Description of Artificial Sequence: nucleotide sequence of mesoCAR

<400> SEQUENCE: 10

| | | | | | |
|---|---|---|---|---|---|
| atggccttac | cagtgaccgc | cttgctcctg | ccgctggcct | tgctgctcca | cgccgccagg | 60 |
| ccgagcgagg | tgcagctggt | ggagtccggg | ggaggcctgg | tccagcctgg | gggatccctg | 120 |
| agactctcct | gcgcagcctc | tggattcgac | ctcggtttct | acttttacgc | ctgttgggtc | 180 |
| cgccaggctc | cagggaaggg | cctggagtgg | gtctcatgca | tttatactgc | tggtagtggt | 240 |
| agcacgtact | acgcgagctg | ggcgaaaggc | cgattcacca | tctccagaga | caattcgaag | 300 |
| aacacgctgt | atctgcaaat | gaacagtctg | agagccgagg | acacggccgt | gtattactgt | 360 |
| gcgagatcta | ctgctaatac | tagaagtact | tattatctta | acttgtgggg | ccaaggcacc | 420 |
| ctggtcaccg | tctcctcagg | cggaggcgga | tcaggtggtg | gcggatctgg | aggtggcgga | 480 |
| agcgacatcc | agatgaccca | gtctccatcc | tccctgtctg | catctgtggg | agacagagtc | 540 |
| accatcactt | gccaggccag | tcagaggatt | agtagttact | tatcctggta | tcagcagaaa | 600 |
| ccagggaaag | ttcccaagct | cctgatctat | ggtgcatcca | ctctggcatc | tggggtcccc | 660 |
| tcgcggttca | gtggcagtgg | atctgggaca | gatttcactc | tcaccatcag | cagcctgcag | 720 |
| cctgaagatg | ttgccactta | ctactgtcag | agttatgctt | attttgatag | taataattgg | 780 |
| catgctttcg | gcggagggac | caaggtggag | atcaaagagt | ccaaatatgg | tcccccatgc | 840 |
| ccaccatgcc | cagcacctcc | cgtggccgga | ccatcagtct | tcctgttccc | cccaaaaccc | 900 |
| aaggacactc | tcatgatctc | ccggaccccg | gaggtcacgt | gcgtggtggt | ggacgtgagc | 960 |
| caggaagacc | ccgaggtcca | gttcaactgg | tacgtggatg | gcgtggaggt | gcataatgcc | 1020 |
| aagacaaagc | cgcgggagga | gcagttccag | agcacgtacc | gtgtggtcag | cgtcctcacc | 1080 |
| gtcctgcacc | aggactggct | gaacggcaag | gagtacaagt | gcaaggtctc | caacaaaggc | 1140 |
| ctcccgtcct | ccatcgagaa | aaccatctcc | aaagccaaag | gcagccccg | agagccacag | 1200 |
| gtgtacaccc | tgcccccatc | ccaggaggag | atgaccaaga | accaggtcag | cctgacctgc | 1260 |
| ctggtcaaag | gcttctaccc | cagcgacatc | gccgtggagt | gggagagcaa | tgggcagccg | 1320 |
| gagaacaact | acaagaccac | gcctcccgtg | ctggactccg | acggctcctt | cttcctctac | 1380 |
| agcaggctaa | ccgtggacaa | gagcaggtgg | caggagggga | atgtcttctc | atgctccgtg | 1440 |
| atgcatgagg | ctctgcacaa | ccactacaca | cagaagagcc | tctccctgtc | tctgggtaaa | 1500 |
| cccttttggg | tgctggtggt | ggttggtgga | gtcctggctt | gctatagctt | gctagtaaca | 1560 |
| gtggccttta | ttattttctg | ggtgaggagt | aagaggagca | ggctcctgca | cagtgactac | 1620 |
| atgaacatga | ctccccgccg | ccccgggccc | acccgcaagc | attaccagcc | ctatgcccca | 1680 |
| ccacgcgact | tcgcagccta | tcgctccaga | gtgaagttca | gcaggagcgc | agacgccccc | 1740 |
| gcgtaccagc | agggccagaa | ccagctctat | aacgagctca | atctaggacg | aagagaggag | 1800 |
| tacgatgttt | tggacaagag | acgtggccgg | gaccctgaga | tggggggaaa | gccgagaagg | 1860 |
| aagaaccctc | aggaaggcct | gtacaatgaa | ctgcagaaag | ataagatggc | ggaggcctac | 1920 |
| agtgagattg | ggatgaaagg | cgagcgccgg | aggggcaagg | gcacgatgg | cctttaccag | 1980 |
| ggtctcagta | cagccaccaa | ggacacctac | gacgcccttc | acatgcaggc | cctgccccct | 2040 | cgc                                                                 2043

<210> SEQ ID NO 11
<211> LENGTH: 679
<212> TYPE: PRT
<213> ORGANISM: Artificial Sequence
<220> FEATURE:
<223> OTHER INFORMATION: Description of Artificial Sequence: amino acid
      sequence of Meso3CAR

<400> SEQUENCE: 11

Met Glu Ala Pro Ala Gln Leu Leu Phe Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asp
        35                  40                  45

Leu Gly Phe Tyr Phe Tyr Ala Cys Trp Val Arg Gln Ala Pro Gly Lys
    50                  55                  60

Gly Leu Glu Trp Val Ser Cys Ile Tyr Thr Ala Ser Gly Ser Thr
65                  70                  75                  80

Tyr Tyr Ala Ser Trp Ala Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Ser Thr Ala Asn Thr Arg Ser Thr
        115                 120                 125

Tyr Tyr Leu Asn Leu Trp Gly Gln Gly Thr Leu Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Gln Ala Ser Gln Arg Ile Ser Ser Tyr Leu
            180                 185                 190

Ser Trp Tyr Gln Gln Lys Pro Gly Lys Val Pro Lys Leu Leu Ile Tyr
        195                 200                 205

Gly Ala Ser Thr Leu Ala Ser Gly Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Ser Tyr Ala Tyr Phe Asp Ser Asn
                245                 250                 255

Asn Trp His Ala Phe Gly Gly Gly Thr Lys Val Glu Ile Lys Glu Ser
            260                 265                 270

Lys Tyr Gly Pro Pro Cys Pro Pro Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser Gln Glu
305                 310                 315                 320

Asp Pro Glu Val Gln Phe Asn Trp Tyr Val Asp Gly Val Glu Val His
                325                 330                 335

Asn Ala Lys Thr Lys Pro Arg Glu Glu Gln Phe Gln Ser Thr Tyr Arg
            340                 345                 350

Val Val Ser Val Leu Thr Val His Gln Asp Trp Leu Asn Gly Lys
            355                 360                 365

Glu Tyr Lys Cys Lys Val Ser Asn Lys Gly Leu Pro Ser Ser Ile Glu
370                 375                 380

Lys Thr Ile Ser Lys Ala Lys Gly Gln Pro Arg Glu Pro Gln Val Tyr
385                 390                 395                 400

Thr Leu Pro Pro Ser Gln Glu Glu Met Thr Lys Asn Gln Val Ser Leu
                405                 410                 415

Thr Cys Leu Val Lys Gly Phe Tyr Pro Ser Asp Ile Ala Val Glu Trp
                420                 425                 430

Glu Ser Asn Gly Gln Pro Glu Asn Asn Tyr Lys Thr Thr Pro Pro Val
            435                 440                 445

Leu Asp Ser Asp Gly Ser Phe Phe Leu Tyr Ser Arg Leu Thr Val Asp
450                 455                 460

Lys Ser Arg Trp Gln Glu Gly Asn Val Phe Ser Cys Ser Val Met His
465                 470                 475                 480

Glu Ala Leu His Asn His Tyr Thr Gln Lys Ser Leu Ser Leu Ser Leu
                485                 490                 495

Gly Lys Pro Phe Trp Val Leu Val Val Val Gly Gly Val Leu Ala Cys
            500                 505                 510

Tyr Ser Leu Leu Val Thr Val Ala Phe Ile Ile Phe Trp Val Arg Ser
            515                 520                 525

Lys Arg Ser Arg Leu Leu His Ser Asp Tyr Met Asn Met Thr Pro Arg
530                 535                 540

Arg Pro Gly Pro Thr Arg Lys His Tyr Gln Pro Tyr Ala Pro Pro Arg
545                 550                 555                 560

Asp Phe Ala Ala Tyr Arg Ser Arg Val Lys Phe Ser Arg Ser Ala Asp
                565                 570                 575

Ala Pro Ala Tyr Gln Gln Gly Gln Asn Gln Leu Tyr Asn Glu Leu Asn
            580                 585                 590

Leu Gly Arg Arg Glu Glu Tyr Asp Val Leu Asp Lys Arg Arg Gly Arg
            595                 600                 605

Asp Pro Glu Met Gly Gly Lys Pro Arg Arg Lys Asn Pro Gln Glu Gly
610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
                645                 650                 655

Tyr Gln Gly Leu Ser Thr Ala Thr Lys Asp Thr Tyr Asp Ala Leu His
            660                 665                 670

Met Gln Ala Leu Pro Pro Arg
            675

<210> SEQ ID NO 12
<211> LENGTH: 2040
<212> TYPE: DNA
<213> ORGANISM: Artificial Sequence
<220> FEATURE:
<223> OTHER INFORMATION: Description of Artificial Sequence: nucleotide
      sequence of Meso3CAR

<400> SEQUENCE: 12
atggaagccc agctcagct tctcttcctc ctgctactct ggctcccaga taccaccgga      60
gaggtgcagt ggtggagtc cgggggaggc ctggtccagc ctgggggatc cctgagactc     120
tcctgcgcag cctctggatt cgacctcggt ttctactttt acgcctgttg ggtccgccag     180

```
gctccaggga agggcctgga gtgggtctca tgcatttata ctgctggtag tggtagcacg    240
tactacgcga gctgggcgaa aggccgattc accatctcca gagacaattc gaagaacacg    300
ctgtatctgc aaatgaacag tctgagagcc gaggacacgg ccgtgtatta ctgtgcgaga    360
tctactgcta atactagaag tacttattat cttaacttgt ggggccaagg caccctggtc    420
accgtctcct caggcggagg cggatcaggt ggtggcggat ctggaggtgg cggaagcgac    480
atccagatga cccagtctcc atcctccctg tctgcatctg tgggagacag agtcaccatc    540
acttgccagg ccagtcagag gattagtagt tacttatcct ggtatcagca gaaaccaggg    600
aaagttccca agtccctgat ctatggtgca tccactctgg catctggggt ccctcgcgg    660 ttcagtggca gtggatctgg gacagatttc actctcacca tcagcagcct gcagcctgaa    720
gatgttgcca cttactactg tcagagttat gcttattttg atagtaataa ttggcatgct    780
ttcggcggag ggaccaaggt ggagatcaaa gagtccaaat atggtccccc atgcccacca    840
tgcccagcac ctcccgtggc cggaccatca gtcttcctgt tccccccaaa acccaaggac    900
actctcatga tctcccggac ccctgaggtc acgtgcgtgg tggtggacgt gagccaggaa    960 gacccc gagg tccagttcaa ctggtacgtg atggcgtgg aggtgcataa tgccaagaca   1020
aagccgcggg aggagcagtt ccagagcacg taccgtgtgg tcagcgtcct caccgtcctg   1080
caccaggact ggctgaacgg caaggagtac aagtgcaagg tctccaacaa aggcctcccg   1140
tcctccatcg agaaaaccat ctccaaagcc aagggcagc cccgagagcc acaggtgtac   1200
accctgcccc catcccagga ggagatgacc aagaaccagg tcagcctgac ctgcctggtc   1260
aaaggcttct accccagcga catcgccgtg gagtgggaga gcaatgggca gccggagaac   1320
aactacaaga ccacgcctcc cgtgctggac tccgacggct ccttcttcct ctacagcagg   1380
ctaaccgtgg acaagagcag gtggcaggag gggaatgtct tctcatgctc cgtgatgcat   1440
gaggctctgc acaaccacta cacacagaag agcctctccc tgtctctggg taaaccctt   1500 tgggtgctgg tggtggttgg tggagtcctg gcttgctata gcttgctagt aacagtggcc   1560
tttattattt tctgggtgag gagtaagagg agcaggctcc tgcacagtga ctacatgaac   1620
atgactcccc gccgccccgg gcccacccgc aagcattacc agcccctgc ccaccacgc   1680 gacttcgcag cctatcgctc cagagtgaag ttcagcagga gcgcagacgc ccccgcgtac   1740
cagcagggcc agaaccagct ctataacgag ctcaatctag gacgaagaga ggagtacgat   1800
gttttggaca agagacgtgg ccgggaccct gagatggggg gaaagccgag aaggaagaac   1860
cctcaggaag gcctgtacaa tgaactgcag aaagataaga tggcggaggc ctacagtgag   1920
attgggatga aggcgagcg ccggagggc aaggggcacg atggcctta ccagggtctc   1980 agtacagcca ccaaggacac ctacgacgcc cttcacatgc aggccctgcc ccctcgctga   2040
```

<210> SEQ ID NO 13
<211> LENGTH: 580
<212> TYPE: PRT
<213> ORGANISM: Artificial Sequence
<220> FEATURE:
<223> OTHER INFORMATION: Description of Artificial Sequence: amino acid
      sequence of ErbBCAR

<400> SEQUENCE: 13

Met Ala Leu Pro Val Thr Ala Leu Leu Leu Pro Leu Ala Leu Leu Leu
1               5                   10                  15

His Ala Ala Arg Pro Ser Val Val Ser His Phe Asn Asp Cys Pro Leu
            20                  25                  30

```
Ser His Asp Gly Tyr Cys Leu His Asp Gly Val Cys Met Tyr Ile Glu
         35                  40                  45

Ala Leu Asp Lys Tyr Ala Cys Asn Cys Val Val Gly Tyr Ile Gly Glu
 50                  55                  60

Arg Cys Gln Tyr Arg Asp Leu Lys Trp Trp Glu Leu Arg Glu Ala Ala
 65                  70                  75                  80

Ala Lys Glu Ala Ala Lys Glu Ala Ala Lys Gly Thr His Ser
             85                  90                  95

Leu Pro Pro Arg Pro Ala Ala Val Pro Val Pro Leu Arg Met Gln Pro
                 100                 105                 110

Gly Pro Ala His Pro Val Leu Ser Phe Leu Arg Pro Ser Trp Asp Leu
             115                 120                 125

Val Ser Ala Phe Tyr Ser Leu Pro Leu Ala Pro Leu Ser Pro Thr Ser
 130                 135                 140

Val Pro Ile Ser Pro Val Ser Val Gly Arg Gly Pro Asp Pro Asp Ala
 145                 150                 155                 160

His Val Ala Val Asp Leu Ser Arg Tyr Glu Gly Ser Lys Tyr Gly
             165                 170                 175

Pro Pro Cys Pro Pro Cys Pro Ala Pro Pro Val Ala Gly Pro Ser Val
             180                 185                 190

Phe Leu Phe Pro Pro Lys Pro Lys Asp Thr Leu Met Ile Ser Arg Thr
         195                 200                 205

Pro Glu Val Thr Cys Val Val Val Asp Val Ser Gln Glu Asp Pro Glu
         210                 215                 220

Val Gln Phe Asn Trp Tyr Val Asp Gly Val Glu Val His Asn Ala Lys
225                 230                 235                 240

Thr Lys Pro Arg Glu Glu Gln Phe Gln Ser Thr Tyr Arg Val Val Ser
                 245                 250                 255

Val Leu Thr Val Leu His Gln Asp Trp Leu Asn Gly Lys Glu Tyr Lys
             260                 265                 270

Cys Lys Val Ser Asn Lys Gly Leu Pro Ser Ser Ile Glu Lys Thr Ile
         275                 280                 285

Ser Lys Ala Lys Gly Gln Pro Arg Glu Pro Gln Val Tyr Thr Leu Pro
         290                 295                 300

Pro Ser Gln Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                 325                 330                 335

Gly Gln Pro Glu Asn Asn Tyr Lys Thr Thr Pro Pro Val Leu Asp Ser
             340                 345                 350

Asp Gly Ser Phe Phe Leu Tyr Ser Arg Leu Thr Val Asp Lys Ser Arg
             355                 360                 365

Trp Gln Glu Gly Asn Val Phe Ser Cys Ser Val Met His Glu Ala Leu
         370                 375                 380

His Asn His Tyr Thr Gln Lys Ser Leu Ser Leu Ser Leu Gly Lys Pro
385                 390                 395                 400

Phe Trp Val Leu Val Val Val Gly Gly Val Leu Ala Cys Tyr Ser Leu
                 405                 410                 415

Leu Val Thr Val Ala Phe Ile Ile Phe Trp Val Arg Ser Lys Arg Ser
             420                 425                 430

Arg Leu Leu His Ser Asp Tyr Met Asn Met Thr Pro Arg Arg Pro Gly
             435                 440                 445
```

```
Pro Thr Arg Lys His Tyr Gln Pro Tyr Ala Pro Pro Arg Asp Phe Ala
    450                 455                 460

Ala Tyr Arg Ser Arg Val Lys Phe Ser Arg Ser Ala Asp Ala Pro Ala
465                 470                 475                 480

Tyr Gln Gln Gly Gln Asn Gln Leu Tyr Asn Glu Leu Asn Leu Gly Arg
                485                 490                 495

Arg Glu Glu Tyr Asp Val Leu Asp Lys Arg Arg Gly Arg Asp Pro Glu
                500                 505                 510

Met Gly Gly Lys Pro Arg Arg Lys Asn Pro Gln Glu Gly Leu Tyr Asn
            515                 520                 525

Glu Leu Gln Lys Asp Lys Met Ala Glu Ala Tyr Ser Glu Ile Gly Met
    530                 535                 540

Lys Gly Glu Arg Arg Arg Gly Lys Gly His Asp Gly Leu Tyr Gln Gly
545                 550                 555                 560

Leu Ser Thr Ala Thr Lys Asp Thr Tyr Asp Ala Leu His Met Gln Ala
                565                 570                 575

Leu Pro Pro Arg
            580

<210> SEQ ID NO 14
<211> LENGTH: 1740
<212> TYPE: DNA
<213> ORGANISM: Artificial Sequence
<220> FEATURE:
<223> OTHER INFORMATION: Description of Artificial Sequence: nucleotide
      sequence of ErbBCAR

<400> SEQUENCE: 14
atggccttac cagtgaccgc cttgctcctg ccgctggcct tgctgctcca cgccgccagg      60
ccgagcgtgg tgtcccattt taatgactgt ccctgtccc acgatgggta ctgcctccat     120
gatggtgtgt gcatgtatat tgaagcattg acaagtatg catgcaactg tgttgttggc     180
tacatcgggg agcgatgtca gtaccgagac ctgaagtggt gggaactgcg cgaagctgcc     240
gctaaggagg ccgcagccaa agaggccgct gcaaagggca cccacagcct gcccccccgc     300
cccgccgccg tgcccgtgcc cctgcgcatg cagcccggcc ccgccacccc cgtgctgagc     360
ttcctgcgcc ccagctggga cctggtgagc gccttctaca gcctgccct ggccccctg      420 agccccacca gcgtgcccat cagccccgtg agcgtgggcc gcggcccga ccccgacgcc      480 cacgtggccg tggacctgag ccgctacgag ggcgagtcca aatatggtcc ccatgcccca     540
ccatgcccag cacctcccgt ggccggacca tcagtcttcc tgttcccccc aaaacccaag     600
gacactctca tgatctcccg gacccctgag gtcacgtgcg tggtggtgga cgtgagccag     660
gaagaccccg aggtccagtt caactggtac gtggatggcg tggaggtgca taatgccaag     720
acaaagccgc gggaggagca gttccagagc acgtaccgtg tggtcagcgt cctcaccgtc     780
ctgcaccagg actggctgaa cggcaaggag tacaagtgca aggtctccaa caaaggcctc     840
ccgtcctcca tcgagaaaac catctccaaa gccaagggc agccccgaga gccacaggtg     900
tacaccctgc cccatcccca ggaggagatg accaagaacc aggtcagcct gacctgcctg     960
gtcaaaggct tctaccccag cgacatcgcc gtggagtggg agagcaatgg gcagccggag    1020
aacaactaca agaccacgcc tcccgtgctg gactccgacg gctccttctt cctctacagc    1080
aggctaaccg tggacaagag caggtggcag gaggggaatg tcttctcatg ctccgtgatg    1140
catgaggctc tgcacaacca ctacacacag aagagcctct ccctgtctct gggtaaaccc    1200
ttttgggtgc tggtggtggt tggtggagtc ctggcttgct atagcttgct agtaacagtg    1260
```

```
gcctttatta ttttctgggt gaggagtaag aggagcaggc tcctgcacag tgactacatg      1320
aacatgactc cccgccgccc cgggcccacc cgcaagcatt accagcccta tgccccacca      1380
cgcgacttcg cagcctatcg ctccagagtg aagttcagca ggagcgcaga cgccccgcg       1440 taccagcagg gccagaacca gctctataac gagctcaatc taggacgaag agaggagtac      1500
gatgttttgg acaagagacg tggccgggac cctgagatgg ggggaaagcc gagaaggaag      1560
aaccctcagg aaggcctgta caatgaactg cagaaagata gatggcgga ggcctacagt       1620 gagattggga tgaaggcgga cgccggagg ggcaaggggc acgatggcct ttaccagggt        1680
ctcagtacag ccaccaagga cacctacgac gcccttcaca tgcaggccct gccccctcgc      1740
```

<210> SEQ ID NO 15
<211> LENGTH: 678
<212> TYPE: PRT
<213> ORGANISM: Artificial Sequence
<220> FEATURE:
<223> OTHER INFORMATION: Description of Artificial Sequence: amino acid
      sequence of Muc1CAR

<400> SEQUENCE: 15

Met Ala Leu Pro Val Thr Ala Leu Leu Leu Pro Leu Ala Leu Leu Leu
1               5                   10                  15

His Ala Ala Arg Pro Ser Asp Ile Val Ile Thr Gln Ser Thr Ala Ser
                20                  25                  30

Leu Gly Val Ser Leu Gly Gln Arg Ala Thr Ile Ser Cys Arg Ala Ser
            35                  40                  45

Lys Ser Val Ser Thr Ser Gly Tyr Ser Tyr Met His Trp Tyr Gln Gln
        50                  55                  60

Arg Pro Gly Gln Pro Pro Lys Leu Leu Ile Tyr Leu Ala Ser Asn Leu
65                  70                  75                  80

Glu Ser Gly Val Pro Ala Arg Phe Ser Gly Ser Gly Ser Gly Thr Asp
                85                  90                  95

Phe Thr Leu Asn Ile His Pro Val Glu Glu Asp Ala Ala Thr Tyr
            100                 105                 110

Tyr Cys Gln His Ser Arg Glu Leu Pro Phe Thr Phe Gly Gly Gly Thr
        115                 120                 125

Lys Leu Glu Ile Lys Gly Gly Gly Gly Ser Gly Gly Gly Gly Ser Gly
    130                 135                 140

Gly Gly Gly Ser Glu Val Gln Leu Glu Glu Ser Gly Gly Gly Leu Val
145                 150                 155                 160

Lys Pro Gly Gly Ser Leu Lys Leu Ser Cys Ala Ala Ser Gly Phe Thr
                165                 170                 175

Phe Ser Gly Tyr Ala Met Ser Trp Val Arg Gln Thr Pro Glu Lys Arg
            180                 185                 190

Leu Glu Trp Val Ala Thr Ile Ser Ser Gly Gly Thr Tyr Ile Tyr Tyr
        195                 200                 205

Pro Asp Ser Val Lys Gly Arg Phe Thr Ile Ser Arg Asp Asn Ala Lys
    210                 215                 220

Asn Thr Leu Tyr Leu Gln Met Ser Ser Leu Arg Ser Glu Asp Thr Ala
225                 230                 235                 240

Met Tyr Tyr Cys Ala Arg Leu Gly Gly Asp Asn Tyr Tyr Glu Tyr Phe
                245                 250                 255

Asp Val Trp Gly Ala Gly Thr Thr Val Thr Val Ser Ser Glu Ser Lys
            260                 265                 270

```
Tyr Gly Pro Pro Cys Pro Pro Cys Pro Ala Pro Pro Val Ala Gly Pro
            275                 280                 285

Ser Val Phe Leu Phe Pro Pro Lys Pro Lys Asp Thr Leu Met Ile Ser
        290                 295                 300

Arg Thr Pro Glu Val Thr Cys Val Val Val Asp Val Ser Gln Glu Asp
305                 310                 315                 320

Pro Glu Val Gln Phe Asn Trp Tyr Val Asp Gly Val Glu Val His Asn
                325                 330                 335

Ala Lys Thr Lys Pro Arg Glu Glu Gln Phe Gln Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Gly Leu Pro Ser Ser Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Arg Leu Thr Val Asp Lys
    450                 455                 460

Ser Arg Trp Gln Glu Gly Asn Val Phe Ser Cys Ser Val Met His Glu
465                 470                 475                 480

Ala Leu His Asn His Tyr Thr Gln Lys Ser Leu Ser Leu Ser Leu Gly
                485                 490                 495

Lys Pro Phe Trp Val Leu Val Val Val Gly Gly Val Leu Ala Cys Tyr
            500                 505                 510

Ser Leu Leu Val Thr Val Ala Phe Ile Ile Phe Trp Val Arg Ser Lys
        515                 520                 525

Arg Ser Arg Leu Leu His Ser Asp Tyr Met Asn Met Thr Pro Arg Arg
530                 535                 540

Pro Gly Pro Thr Arg Lys His Tyr Gln Pro Tyr Ala Pro Pro Arg Asp
545                 550                 555                 560

Phe Ala Ala Tyr Arg Ser Arg Val Lys Phe Ser Arg Ser Ala Asp Ala
                565                 570                 575

Pro Ala Tyr Gln Gln Gly Gln Asn Gln Leu Tyr Asn Glu Leu Asn Leu
            580                 585                 590

Gly Arg Arg Glu Glu Tyr Asp Val Leu Asp Lys Arg Gly Arg Asp
        595                 600                 605

Pro Glu Met Gly Gly Lys Pro Arg Arg Lys Asn Pro Gln Glu Gly Leu
610                 615                 620

Tyr Asn Glu Leu Gln Lys Asp Lys Met Ala Glu Ala Tyr Ser Glu Ile
625                 630                 635                 640

Gly Met Lys Gly Glu Arg Arg Arg Gly Lys Gly His Asp Gly Leu Tyr
                645                 650                 655

Gln Gly Leu Ser Thr Ala Thr Lys Asp Thr Tyr Asp Ala Leu His Met
            660                 665                 670

Gln Ala Leu Pro Pro Arg
        675
```

```
<210> SEQ ID NO 16
<211> LENGTH: 2037
<212> TYPE: DNA
<213> ORGANISM: Artificial Sequence
<220> FEATURE:
<223> OTHER INFORMATION: Description of Artificial Sequence: nucleotide
      sequence of Muc1CAR

<400> SEQUENCE: 16
atggccttac cagtgaccgc cttgctcctg ccgctggcct tgctgctcca cgccgccagg     60
ccgagcgaca ttgtgatcac acagtctaca gcttccttag gtgtatctct ggggcagagg    120
gccaccatct catgcagggc cagcaaaagt gtcagtacat ctggctatag ttatatgcac    180
tggtaccaac agagaccagg acagccaccc aaactcctca tctatcttgc atccaaccta    240
gaatctgggg tccctgccag gttcagtggc agtgggtctg gacagactt caccctcaac    300 atccatcctg tggaggagga ggatgctgca acctattact gtcagcacag tagggagctt    360
ccgttcacgt tcggagggg gaccaagctg gagataaaag gtggaggcgg ttcaggcgga    420
ggtggcagcg gcggtggcgg gtcggaggtc cagctggagg agtcagggggg aggcttagtg    480 aagcctggag ggtccctgaa actctcctgt gcagcctctg gattcacttt cagtggctat    540
gccatgtctt ggttcgcca gactccggag aagaggctgg agtgggtcgc aaccattagt    600
agtggtggta cttatatcta ctatccagac agtgtgaagg ggcgattcac catctccaga    660
gacaatgcca agaacaccct gtacctgcaa atgagcagtc tgaggtctga ggacacggcc    720
atgtattact gtgcaagact tggggggat aattactacg aatacttcga tgtctggggc    780
gcagggacca cggtcaccgt ctcctccgag tccaaatatg gtcccccatg ccaccatgc    840 ccagcacctc ccgtggccgg accatcagtc ttcctgttcc ccccaaaacc caaggacact    900
ctcatgatct cccggacccc tgaggtcacg tgcgtggtgg tggacgtgag ccaggaagac    960
cccgaggtcc agttcaactg gtacgtggat ggcgtggagg tgcataatgc caagacaaag   1020
ccgcgggagg agcagttcca gagcacgtac cgtgtggtca gcgtcctcac cgtcctgcac   1080
caggactggc tgaacggcaa ggagtacaag tgcaaggtct ccaacaaagg cctcccgtcc   1140
tccatcgaga aaaccatctc caaagccaaa gggcagcccc gagagccaca ggtgtacacc   1200 ctgccccat cccaggagga gatgaccaag aaccaggtca gcctgacctg cctggtcaaa   1260
ggcttctacc ccagcgacat cgccgtggag tgggagagca atgggcagcc ggagaacaac   1320
tacaagacca cgcctcccgt gctggactcc gacggctcct tcttcctcta cagcaggcta   1380
accgtggaca gagcaggtg gcaggagggg aatgtcttct catgctccgt gatgcatgag   1440
gctctgcaca accactacac acagaagagc ctctccctgt ctctgggtaa acccttttgg   1500
gtgctggtgg tggttggtgg agtcctggct tgctatagct tgctagtaac agtggccttt   1560
attattttct gggtgaggag taagaggagc aggctcctgc acagtgacta catgaacatg   1620
actccccgcc gccccgggcc cacccgcaag cattaccagc cctatgcccc accacgcgac   1680
ttcgcagcct atcgctccag agtgaagttc agcaggagcg cagacgcccc cgcgtaccag   1740
cagggccaga accagctcta taacgagctc aatctaggac gaagagagga gtacgatgtt   1800
ttggacaaga gacgtggccg ggaccctgag atggggggaa agccgagaag gaagaaccct   1860
caggaaggcc tgtacaatga actgcagaaa gataagatgg cggaggccta cagtgagatt   1920
gggatgaaag gcgagcgccg gagggcaag gggcacgatg gcctttacca gggtctcagt   1980
acagccacca aggacaccta cgacgccctt cacatgcagg ccctgccccc tcgctga      2037
```

```
<210> SEQ ID NO 17
<211> LENGTH: 497
<212> TYPE: PRT
<213> ORGANISM: Artificial Sequence
<220> FEATURE:
<223> OTHER INFORMATION: Description of Artificial Sequence: amino acid
      sequence of EGFR-CAR

<400> SEQUENCE: 17

Met Ala Leu Pro Val Thr Ala Leu Leu Leu Pro Leu Ala Leu Leu Leu
1               5                   10                  15

His Ala Ala Arg Pro Ser Asp Ile Leu Leu Thr Gln Ser Pro Val Ile
            20                  25                  30

Leu Ser Val Ser Pro Gly Glu Arg Val Ser Phe Ser Cys Arg Ala Ser
        35                  40                  45

Gln Ser Ile Gly Thr Asn Ile His Trp Tyr Gln Gln Arg Thr Asn Gly
    50                  55                  60

Ser Pro Arg Leu Leu Ile Lys Tyr Ala Ser Glu Ser Ile Ser Gly Ile
65                  70                  75                  80

Pro Ser Arg Phe Ser Gly Ser Gly Ser Gly Thr Asp Phe Thr Leu Ser
                85                  90                  95

Ile Asn Ser Val Glu Ser Glu Asp Ile Ala Asp Tyr Tyr Cys Gln Gln
            100                 105                 110

Asn Asn Asn Trp Pro Thr Thr Phe Gly Ala Gly Thr Lys Leu Glu Leu
        115                 120                 125

Lys Gly Gly Gly Gly Ser Gly Gly Gly Gly Ser Gly Gly Gly Gly Ser
130                 135                 140

Gln Val Gln Leu Lys Gln Ser Gly Pro Gly Leu Val Gln Pro Ser Gln
145                 150                 155                 160

Ser Leu Ser Ile Thr Cys Thr Val Ser Gly Phe Ser Leu Thr Asn Tyr
                165                 170                 175

Gly Val His Trp Val Arg Gln Ser Pro Gly Lys Gly Leu Glu Trp Leu
            180                 185                 190

Gly Val Ile Trp Ser Gly Gly Asn Thr Asp Tyr Asn Thr Pro Phe Thr
        195                 200                 205

Ser Arg Leu Ser Ile Asn Lys Asp Asn Ser Lys Ser Gln Val Phe Phe
    210                 215                 220

Lys Met Asn Ser Leu Gln Ser Asn Asp Thr Ala Ile Tyr Tyr Cys Ala
225                 230                 235                 240

Arg Ala Leu Thr Tyr Tyr Asp Tyr Glu Phe Ala Tyr Trp Gly Gln Gly
                245                 250                 255

Thr Leu Val Thr Val Ser Ser Phe Val Pro Val Phe Leu Pro Ala Lys
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Asn His Arg Ser Lys Arg Ser Arg Leu Leu
            340                 345                 350

His Ser Asp Tyr Met Asn Met Thr Pro Arg Arg Pro Gly Pro Thr Arg
        355                 360                 365
```

```
Lys His Tyr Gln Pro Tyr Ala Pro Pro Arg Asp Phe Ala Ala Tyr Arg
    370                 375                 380
Ser Arg Val Lys Phe Ser Arg Ser Ala Asp Ala Pro Ala Tyr Gln Gln
385                 390                 395                 400
Gly Gln Asn Gln Leu Tyr Asn Glu Leu Asn Leu Gly Arg Arg Glu Glu
                405                 410                 415
Tyr Asp Val Leu Asp Lys Arg Arg Gly Arg Asp Pro Glu Met Gly Gly
            420                 425                 430
Lys Pro Arg Arg Lys Asn Pro Gln Glu Gly Leu Tyr Asn Glu Leu Gln
        435                 440                 445
Lys Asp Lys Met Ala Glu Ala Tyr Ser Glu Ile Gly Met Lys Gly Glu
    450                 455                 460
Arg Arg Arg Gly Lys Gly His Asp Gly Leu Tyr Gln Gly Leu Ser Thr
465                 470                 475                 480
Ala Thr Lys Asp Thr Tyr Asp Ala Leu His Met Gln Ala Leu Pro Pro
                485                 490                 495
Arg
```

<210> SEQ ID NO 18
<211> LENGTH: 1494
<212> TYPE: DNA
<213> ORGANISM: Artificial Sequence
<220> FEATURE:
<223> OTHER INFORMATION: Description of Artificial Sequence: nucleotide
      sequence of EGFR-CAR

<400> SEQUENCE: 18

```
atggccttac cagtgaccgc cttgctcctg ccgctggcct tgctgctcca cgccgccagg    60
ccgagcgaca tcttgctgac tcagtctcca gtcatcctgt ctgtgagtcc aggagaaaga   120
gtcagtttct cctgcagggc cagtcagagt attggcacaa acatacactg gtatcagcaa   180
agaacaaatg ttctccaag gcttctcata aagtatgctt ctgagtctat ctctgggatc    240
ccttccaggt ttagtggcag tggatcaggg acagatttta ctcttagcat caacagtgtg   300
gagtctgaag atattgcaga ttattactgt caacaaaata taactggcc aaccacgttc    360 ggtgctggga ccaagctgga gctgaaaggt ggaggcggtt caggcggagg tggcagcggc   420
ggtggcgggt cgcaggtgca gctgaagcag tcaggacctg gcctagtgca gccctcacag   480
agcctgtcca tcacctgcac agtctctggt ttctcattaa ctaactatgg tgtacactgg   540
gttcgccagt ctccaggaaa gggtctggag tggctgggag tgatatggag tggtggaaac   600
acagactata tacacccttt cacatccaga ctgagcatca caaggacaa ttccaagagc    660 caagttttct ttaaaatgaa cagtctgcaa tctaatgaca cagccatata ttactgtgcc   720
agagccctca cctactatga ttacgagttt gcttactggg gccaagggac tctggtcact   780
gtctcttcgt tcgtgccggt cttcctgcca gcgaagccca ccacgacgcc agcgccgcga   840
ccaccaacac cggcgcccac catcgcgtcg cagcccctgt ccctgcgccc agaggcgtgc   900
cggccagcgg cggggggcgc agtgcacacg agggggctgg acttcgcctg tgatatctac   960
atctgggcgc ccctggccgg gacttgtggg gtccttctcc tgtcactggt tatcaccctt  1020
tactgcaacc acaggagtaa gaggagcagg ctcctgcaca gtgactacat gaacatgact  1080
ccccgccgcc ccgggcccac ccgcaagcat taccagccct atgccccacc acgcgacttc  1140
gcagcctatc gctccagagt gaagttcagc aggagcgcag acgcccccgc gtaccagcag  1200
ggccagaacc agctctataa cgagctcaat ctaggacgaa gagaggagta cgatgttttg  1260
```

```
gacaagagac gtggccggga ccctgagatg gggggaaagc cgagaaggaa gaaccctcag   1320
gaaggcctgt acaatgaact gcagaaagat aagatggcgg aggcctacag tgagattggg   1380
atgaaaggcg agcgccggag gggcaagggg cacgatggcc tttaccaggg tctcagtaca   1440
gccaccaagg acacctacga cgcccttcac atgcaggccc tgccccctcg ctga         1494
```

<210> SEQ ID NO 19
<211> LENGTH: 78
<212> TYPE: DNA
<213> ORGANISM: Artificial Sequence
<220> FEATURE:
<223> OTHER INFORMATION: Description of Artificial Sequence: nucleotide
      sequence of Linker 2A

<400> SEQUENCE: 19

```
cgtaggaaac gaggcagcgg cgccacaaac ttctctctgc taaagcaagc aggtgatgtt   60
gaagaaaacc ccgggcct                                                 78
```

<210> SEQ ID NO 20
<211> LENGTH: 197
<212> TYPE: DNA
<213> ORGANISM: Artificial Sequence
<220> FEATURE:
<223> OTHER INFORMATION: Description of Artificial Sequence: nucleotide
      sequence of IRES

<400> SEQUENCE: 20

```
ccggcgggtt tctgacatcc ggcgggtttc tgacatccgg cgggtttctg acatccggcg   60
ggtttctgac atccggcggg tttctgacat ccggcgggtt tctgacatcc ggcgggtttc   120
tgacatccgg cgggtttctg acatccggcg ggtttctgac atccggcggg tgactcacaa   180
ccccagaaac agacata                                                  197
```

<210> SEQ ID NO 21
<211> LENGTH: 94
<212> TYPE: PRT
<213> ORGANISM: Artificial Sequence
<220> FEATURE:
<223> OTHER INFORMATION: Description of Artificial Sequence: amino acid
      sequence of mesothelin Region I

<400> SEQUENCE: 21

```
Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
            20                  25                  30

Asp Ala Ala Leu Leu Ala Thr Gln Met Asp Arg Val Asn Ala Ile Pro
        35                  40                  45

Phe Thr Tyr Glu Gln Leu Asp Val Leu Lys His Lys Leu Asp Glu Leu
    50                  55                  60

Tyr Pro Gln Gly Tyr Pro Glu Ser Val Ile Gln His Leu Gly Tyr Leu
65                  70                  75                  80

Phe Leu Lys Met Ser Pro Glu Asp Ile Arg Lys Trp Asn Val
                85                  90
```

<210> SEQ ID NO 22
<211> LENGTH: 111
<212> TYPE: PRT
<213> ORGANISM: Artificial Sequence
<220> FEATURE:
<223> OTHER INFORMATION: Description of Artificial Sequence: amino acid
      sequence of mesothelin Region III

<400> SEQUENCE: 22

Tyr Pro Lys Ala Arg Leu Ala Phe Gln Asn Met Asn Gly Ser Glu Tyr
1               5                   10                  15

Phe Val Lys Ile Gln Ser Phe Leu Gly Gly Ala Pro Thr Glu Asp Leu
            20                  25                  30

Lys Ala Leu Ser Gln Gln Asn Val Ser Met Asp Leu Ala Thr Phe Met
        35                  40                  45

Lys Leu Arg Thr Asp Ala Val Leu Pro Leu Thr Val Ala Glu Val Gln
50                  55                  60

Lys Leu Leu Gly Pro His Val Glu Gly Leu Lys Ala Glu Glu Arg His
65                  70                  75                  80

Arg Pro Val Arg Asp Trp Ile Leu Arg Gln Arg Gln Asp Asp Leu Asp
                85                  90                  95

Thr Leu Gly Leu Gly Leu Gln Gly Gly Ile Pro Asn Gly Tyr Leu
            100                 105                 110

<210> SEQ ID NO 23
<211> LENGTH: 240
<212> TYPE: PRT
<213> ORGANISM: Artificial Sequence
<220> FEATURE:
<223> OTHER INFORMATION: Description of Artificial Sequence: amino acid
      sequence of anti-mesothelin Region I scFv

<400> SEQUENCE: 23

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Asp Ile Glu Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Gly Arg Phe Ser Gly Ser Gly Ser Gly Asn Ser Tyr Ser Leu Thr Ile
        195                 200                 205

Ser Ser Val Glu Ala Glu Asp Asp Ala Thr Tyr Tyr Cys Gln Gln Trp
    210                 215                 220

Ser Lys His Pro Leu Thr Tyr Gly Ala Gly Thr Lys Leu Glu Ile Lys
225                 230                 235                 240

<210> SEQ ID NO 24
<211> LENGTH: 45
<212> TYPE: PRT
<213> ORGANISM: Artificial Sequence
<220> FEATURE:
<223> OTHER INFORMATION: Description of Artificial Sequence: amino acid
      sequence of Muc1 membrane-proximal end

<400> SEQUENCE: 24

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 25
<211> LENGTH: 229
<212> TYPE: PRT
<213> ORGANISM: Artificial Sequence
<220> FEATURE:
<223> OTHER INFORMATION: Description of Artificial Sequence: amino acid
      sequence of wild type IgG4Fc

<400> SEQUENCE: 25

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

ANTIBODY-MODIFIED CHIMERIC ANTIGEN RECEPTOR MODIFIED T CELL AND USES THEREOF

CROSS REFERENCE TO RELATED APPLICATION

This application is a national stage application under 35 U.S.C. § 371 of International Application No. PCT/CN2018/124692, filed internationally on Dec. 28, 2018, which claims priority to Chinese Patent Application No. 201711462801.X filed on Dec. 28, 2017, the content of each of which is incorporated by reference in its entirety.

INCORPORATION BY REFERENCE OF SEQUENCE LISTING

The present application is being filed along with a Sequence Listing in electronic format. The Sequence Listing is provided as a file entitled 699532000500SeqList.txt, created on Jan. 25, 2021, which is 71,051 bytes in size. The information in the electronic format of the Sequence Listing is incorporated by reference in its entirety.

TECHNICAL FIELD

The invention relates to antibody-modified chimeric antigen receptor modified T cell and uses thereof.

BACKGROUND

Chimeric antigen receptor T cell (CAR-T) therapy technology is undoubtedly a rising star in the field of tumor immune cell therapy. CAR-T technology includes: splicing the gene sequence of the antibody variable region that recognizes an antigen molecule with the sequence of the intracellular region of a T lymphocyte immune receptor by genetic engineering technology, introducing the linked sequences into lymphocytes by retrovirus or lentiviral vector, transposon or transposase system or directly mRNA transduction, and expressing the fusion proteins on the cell surface. Such T lymphocytes can recognize specific antigens in a non-MHC-restricted manner, which enhances their ability to recognize and kill tumors.

The structure of CAR was first proposed by the Eshhar research team of Israeli in 1989. After nearly 30 years of development, T cells modified by the CAR structure have been shown to have good efficacy in tumor immunotherapy. The first-generation CAR receptors contain extracellular fragments that specifically recognize tumor antigens (single-chain variable fragment, scFv), and intracellular activation signals are transmitted by the CD3ζ signal chain. However, the first-generation CAR receptor lacks the co-stimulatory signal of T cells, which causes T cells to exert only an instant effect, with a short duration in the body and little secretion of cytokines. The second-generation CAR receptor further contains the intracellular domains of a co-stimulatory signaling molecule, including domains of CD28, CD134/OX40, CD137/4-1BB, lymphocyte-specific protein tyrosine kinase (LCK), inducible T-cell co-stimulator (ICOS) and DNAX-activation protein 10 (DAP10) and the like, enhancing the proliferation of T cells and the secretion of cytokines, and increasing IL-2, IFN-γ and GM-CSF. Therefore, the second-generation CAR receptor is not affected by immunosuppression of the tumor microenvironment, and extends AICD (activation induced cell death). The third-generation CAR receptor further fuses a secondary co-stimulatory molecule such as 4-1BB between the co-stimulatory structure CD28 and the ITAM signal chain, thus generating a triple-signal CAR receptor. T cells engineered by the third-generation CAR receptor have better effector function and longer survival time in vivo. The commonly used typical CAR-T structure is that of the second-generation CAR receptor, which can be divided into the following four parts: antibody single-chain variable region (scFv) that recognizes a tumor antigen, hinge region, transmembrane region, and intracellular stimulation signal regions. The hinge region of the CAR is responsible for forming the correct conformation and forming dimers. The length and amino acid sequence characteristic of the hinge region determine the spatial conformation of the CAR and its ability to bind to tumor cell surface antigens.

At present, CAR-T cells against different targets are undergoing clinical trials for solid tumors treatment, the targets including GD2, FR-α, L1-CAM, HER2, EGFR, EGFRvIII, VEGFR-2, IL-13Rα2, FAP, Mesothelin, c-MET, PSMA, CEA, GPC3, EphA2, MUC1, CAIX (carbonic anhydrase IX), etc. Some clinical trials have relatively good results. For example, in the clinical trial of CAR-T cells against GD2 for the treatment of high-risk neuroblastoma (19 patients), 8 patients had complete tumor regression after reinfusion, 3 patients that did not regress showed a complete response at the 6th week after reinfusion, 1 patients that completely responded still had CAR-T cells after 192 weeks; in the clinical trial of CAR-T cells against HER2 for the treatment of HER2-positive solid tumor (19 cases, of which 16 cases are osteosarcoma), 4 cases maintained a progression-free state for 12 weeks to 14 months, of which 3 cases had tumor regression, 1 case had more than 90% regression. However, compared with hematological tumors, CAR-T treatment for solid tumors generally has poor efficacy, mainly for the following reasons:

1. Immunosuppressive Microenvironment

Solid tumor tissue has an immunosuppressive microenvironment, including Treg cells, tumor-associated fibroblasts, bone marrow-derived immature DC cells, M2-type macrophages, and cytokines secreted by them, such as IL-6, IL-10, IDO, VEGF, TGFβ, etc. These cells and their secreted cytokines can inhibit the function of T cells directly or indirectly. The immunosuppressive microenvironment of the solid tumor can be affected, therefore improving the survival ability and killing effect of infiltrating CAR-T cells, by methods including destroying tumor microenvironment by radiotherapy and chemotherapy, specifically blocking related signaling pathways by immune checkpoint antibodies (such as PD1/PDL1) or negative immunoregulators (such as small molecule inhibitors of IDO), overall adjusting immune microenvironment by inhibitors of epigenetic modification-related enzymes, over-expressing positive immunoregulatory factors (such as IL-12), and direct targeted removal of tumor stromal cells (such as CAR-T targeting FAP-positive tumor-associated fibroblasts).

2. Lack of Suitable CAR-T Treatment Targets

Solid tumors are highly heterogeneous, and there are huge differences between solid tumors of different patients, different lesions in the same patient, or different tumor cells in the same lesion. This high degree of heterogeneity has led to the disadvantage of lacking ideal universal and broad-spectrum targets for tumor targeted therapy, which limits the efficacy of CAR-T cells in the treatment of solid tumors.

Therefore, in order to make CAR-T cells kill more kinds of tumors, some scholars have proposed the idea of TanCAR by connecting two scFvs that bind to different tumor-associated antigens together to form a new CAR that can simultaneously recognize and bind to two targets, which effectively improves the efficacy of CAR-T cells.

3. It is Difficult to Reach an Effective Amount in the Body

T cells need a cluster effect to kill tumor cells, that is, killing one tumor cell requires the cooperation of several T cells. Therefore, only after the effector cells reach a certain number, the tumor cells can be effectively killed. Therefore, T cells can rapidly proliferate upon contacting tumor cells with specific targets, and amplify the killing effect through direct contact and paracrine pathways. CAR-T cells are administered intravenously. In the case of blood tumor, CAR-T cells are very easy to contact tumor cells, leading the number of CAR-T cells rapidly enlarged, or even excessively enlarged to form a cytokine storm; therefore the efficacy is relatively good. However, in the case of solid tumor, CAR-T cells need to reach the tumor site to receive stimulation due to the number of tumor cells in the circulation is limited; therefore it is difficult to achieve an effective amount.

Therefore, if CAR-T cells, especially those can broadly recognize tumor membrane antigens, express antibodies that directly or indirectly stimulate T cell proliferation and survival, the difficulty in CAR-T treatment for solid tumor can be effectively overcame, and the efficacy can be greatly improved.

SUMMARY

The present disclosure provides a T cell expressing an antibody or comprising a coding sequence of the antibody or an expression vector thereof, the antibody comprising an optional signal peptide, an antigen binding sequence, and a mutant Fc segment, wherein, the mutant Fc segment is a mutant Fc segment in which the amino acid residues at positions corresponding to positions 17 and 79 of the IgG4 Fc segment shown as SEQ ID NO: 25 are mutated to E and Q, respectively.

In one or more embodiments, the mutant Fc segment is a mutant IgG4 Fc segment, and its amino acid sequence is preferably as shown in amino acid residues 269-497 of SEQ ID NO: 1, preferably its coding sequence is as shown in nucleotide residues 805-1491 of SEQ ID NO: 2.

In one or more embodiments, an expression cassette of the antibody is integrated into the T cell genome.

In one or more embodiments, the signal peptide is a light chain signal peptide, and its amino acid sequence is preferably as shown in amino acid residues 1-20 of SEQ ID NO: 1, preferably its coding sequence is as shown in nucleotide residues 1-60 of SEQ ID NO: 2.

In one or more embodiments, the antigen binding sequence is derived from an antibody or an antigen-binding fragment thereof that specifically binds to the antigen, such as a single-chain antibody, or from a ligand of a protein that functions in the tumor microenvironment or a fragment thereof that binds to the protein; preferably, the antibody is an agonistic antibody or an inhibitory antibody.

In one or more embodiments, the agonistic antibody is selected from antibodies directed against one or more of the following antigens: CD28, CD137, CD134, CD40, CD40L, ICOS, HVEM, CD2, CD27, CD30, GITR, LIGHT, DR3, SLAM, CD226, CD80 and CD86.

In one or more embodiments, the inhibitory antibody is selected from antibodies directed against one or more of the following antigens: PD-1, CTLA4, PDL1, PDL2, PDL3, TIM3, LAG3, CD47, BTLA, TIGIT, CD160, LAIR1, B7-H1, B7-1, VSIR and CD244; preferably, the ligand is a ligand of CD47.

In one or more embodiments, the agonistic antibody is a CD40 single chain antibody; preferably, the amino acid sequence of the light chain variable region of the CD40 single chain antibody is as shown in amino acid residues 21-146 of SEQ ID NO: 1, and/or the amino acid sequence of the heavy chain variable region of the CD40 single-chain antibody is as shown in amino acid residues 161-268 of SEQ ID NO: 1; preferably, the amino acid sequence of the CD40 single-chain antibody is as shown in amino acid residues 21-268 of SEQ ID NO: 1.

In one or more embodiments, the inhibitory antibody is a PD-1 single chain antibody; preferably, the amino acid sequence of the light chain variable region of the PD-1 single chain antibody is as shown in amino acid residues 21-131 of SEQ ID NO: 3, and/or the amino acid sequence of the heavy chain variable region of the PD-1 single-chain antibody is as shown in amino acid residues 147-266 of SEQ ID NO: 3; preferably, the amino acid sequence of the PD-1 single-chain antibody is as shown in amino acid residues 21-266 of SEQ ID NO: 3.

In one or more embodiments, the amino acid sequence of the CD47 ligand is shown as amino acid residues 21-138 of SEQ ID NO: 5.

In one or more embodiments, the coding sequence of the light chain variable region of the CD40 single-chain antibody is as shown in nucleotide residues 60-438 of SEQ ID NO: 2, and/or the coding sequence of the heavy chain variable region thereof may be as shown in nucleotide residues 481-804 of SEQ ID NO: 2; preferably, the coding sequence of the CD40 single chain antibody is shown as nucleotide residues 60-804 of SEQ ID NO: 2.

In one or more embodiments, the coding sequence of the light chain variable region of the PD-1 single-chain antibody is as shown in nucleotide residues 60-393 of SEQ ID NO: 4, and/or the coding sequence of the heavy chain variable region thereof is as shown in nucleotide residues 439-798 of SEQ ID NO: 4; preferably, the coding sequence of the PD-1 single chain antibody is shown as nucleotide residues 60-798 of SEQ ID NO: 4.

In one or more embodiments, the coding sequence of the CD47 ligand is shown as nucleotide residues 60-414 of SEQ ID NO: 6.

In one or more embodiments, the antibody is a CD40 antibody, PD-1 antibody, or CD47 antibody.

In one or more embodiments, the amino acid sequence of the CD40 antibody is as shown in amino acid residues 21-497 of SEQ ID NO: 1, or as shown in SEQ ID NO: 1, the amino acid sequence of the PD-1 antibody is as shown in amino acid residues 21-495 of SEQ ID NO: 3, or as shown in SEQ ID NO: 3, the amino acid sequence of the CD47 antibody is as shown in amino acid residues 21-367 of SEQ ID NO: 5, or as shown in SEQ ID NO: 5.

In one or more embodiments, the coding sequence of the antibody is as shown in nucleotide residues 60-1491 of SEQ ID NO: 2, or as shown in SEQ ID NO: 2; or is as shown in nucleotide residues 60-1485 of SEQ ID NO: 4, or as shown in SEQ ID NO: 4; or is as shown in nucleotide residues 60-1104 of SEQ ID NO: 6, or as shown in SEQ ID NO: 6.

In one or more embodiments, the T cell is a CAR-T cell expressing a chimeric antigen receptor, wherein the expression cassette of the antibody and the expression cassette of the chimeric antigen receptor are integrated into the genome of the T cell.

In one or more embodiments, the chimeric antigen receptor recognizes, targets, or specifically binds to one or more of the following antigens: CD19, CD20, CEA, GD2, FR, PSMA, PMEL, CA9, CD171/L1-CAM, IL-13Rα2, MART-1, ERBB2, NY-ESO-1, MAGE family proteins, BAGE family proteins, GAGE family proteins, AFP, MUC1, CD22, CD23, CD30, CD33, CD44v7/8, CD70, VEGFR1, VEGFR2, IL-11Rα, EGP-2, EGP-40, FBP, GD3, PSCA, FSA, PSA, HMGA2, fetal acetylcholine receptor, LeY, EpCAM, MSLN, IGFR1, EGFR, EGFRvIII, ERBB3, ERBB4, CA125, CA15-3, CA19-9, CA72-4, CA242, CA50, CYFRA21-1, SCC, AFU, EBV-VCA, POA, β2-MG and PROGRP; preferably the chimeric antigen receptor is those recognizes, targets, or specifically binds to CD19, mesothelin, EGFR, mucin or ErbB receptor family.

In one or more embodiments, the chimeric antigen receptor contains an optional signal peptide sequence, antigen recognition region, hinge region, transmembrane region, intracellular co-stimulatory signal domain and intracellular signal domain; wherein, the signal peptide is selected from the group consisting of a CD8 signal peptide, a CD28 signal peptide, a CD4 signal peptide and a light chain signal peptide; the antigen recognition region is an amino acid sequence that recognizes, targets or specifically binds to the target antigen; and the hinge region is selected from the group consisting of a extracellular hinge region of CD8, a hinge region of IgG1 Fc CH2CH3, a IgD hinge region, a extracellular hinge region of CD28, a hinge region of IgG4 Fc CH2CH3 and a extracellular hinge region of CD4, preferably the hinge region is 50 amino acid residues or more in length, more preferably 80 amino acid residues or more in length; preferably, the hinge region is a CD8a hinge region or a hinge region of IgG4 Fc CH2CH3; the transmembrane region is selected from the group consisting of a transmembrane region of CD28, a transmembrane region of CD8, a transmembrane region of CD3, a transmembrane region of CD134, a transmembrane region of CD137, a transmembrane region of ICOS and a transmembrane region of DAP10; preferably a transmembrane region of CD8 or a transmembrane region of CD28; the intracellular co-stimulatory signal domain is the intracellular domain of a co-stimulatory signal molecule, which is selected from the group consisting of a intracellular domains of CD28, CD134/OX40, CD137/4-1BB, lymphocyte-specific protein tyrosine kinase, a inducible T cell co-stimulatory factor and a DNAX activating protein 10, preferably a intracellular domain of CD137/4-1BB or a intracellular domain of CD28; and/or the intracellular signal domain is a intracellular signal domain of CD3 or a intracellular signal domain of FccRIγ, preferably a intracellular signal domain of CD3.

In one or more embodiments, the amino acid sequence of the signal peptide is as shown in amino acid residues 1-21 of SEQ ID NO: 7, or amino acid residues 1-22 of SEQ ID NO: 9, or amino acid residues 1-20 of SEQ ID NO: 11; the antigen recognition region is a single-chain antibody that recognizes, targets, or specifically binds to CD19, mesothelin, EGFR, or mucin, or consists of the amino acid sequence that recognizes, targets, or specifically binds to the ErbB receptor family; the amino acid sequence of the hinge region is as shown in amino acid residues 264-308 of SEQ ID NO: 7, or amino acid residues 273-500 of SEQ ID NO: 9, or amino acid residues 264-318 of SEQ ID NO: 17; the amino acid sequence of the transmembrane region is as shown in amino acid residues 309-332 of SEQ ID NO: 7, or amino acid residues 501-528 of SEQ ID NO: 9, or amino acid residues 319-344 of SEQ ID NO: 17; the amino acid sequence of the intracellular co-stimulatory signal domain is as shown in amino acid residues 333-374 of SEQ ID NO: 7, or amino acid residues 529-569 of SEQ ID NO: 9; and/or the amino acid sequence of the intracellular signal domain is as shown in amino acid residues 375-486 of SEQ ID NO: 7.

In one or more embodiments, the coding sequence of the signal peptide is as shown in the nucleotide residues 1-63 of SEQ ID NO: 8, or the nucleotide residues 1-66 of SEQ ID NO: 10, or the nucleotide residues 1-60 of SEQ ID NO: 12; the coding sequence of the hinge region is as shown in nucleotide residues 790-924 of SEQ ID NO: 8, or nucleotide residues 817-1500 of SEQ ID NO: 10, or nucleotide residues 790-954 of SEQ ID NO: 18; the coding sequence of the transmembrane region is as shown in the nucleotide residues 925-996 of SEQ ID NO: 8, or the nucleotide residues 1501-1584 of SEQ ID NO: 10, or the nucleotide residues 955-1032 of SEQ ID NO: 18; the coding sequence of the intracellular co-stimulatory signal domain is as shown in the nucleotide residues 997-1122 of SEQ ID NO: 8, or the nucleotide residues 1585-1707 of SEQ ID NO: 10; and/or the coding sequence of the intracellular signal domain is as shown in the nucleotide residues 1123-1458 of SEQ ID NO: 8.

In one or more embodiments, the amino acid sequence of the light chain variable region of the single-chain antibody that recognizes, targets or specifically binds to CD19 may be as shown in amino acid residues 22-128 of SEQ ID NO: 7, and/or the amino acid sequence of the heavy chain variable region thereof may be as shown in amino acid residues 144-263 of SEQ ID NO: 7; preferably, the amino acid sequence of the single-chain antibody is as shown in amino acid residues 22-263 of SEQ ID NO: 7.

In one or more embodiments, the single-chain antibody that recognizes, targets or specifically binds to mesothelin antigen is a single-chain antibody directed against Region I or III of mesothelin, preferably the single-chain antibody directed against Region III of mesothelin; preferably, the amino acid sequence of the light chain variable region of the anti-mesothelin Region III single-chain antibody is as shown in amino acid residues 23-146 of SEQ ID NO: 9, and/or the amino acid sequence of the heavy chain variable region of the anti-mesothelin Region III single-chain antibody is as shown in amino acid residues 162-272 of SEQ ID NO:9; preferably, the amino acid sequence of the single chain antibody that recognizes, targets or specifically binds to mesothelin antigen is as shown in amino acid residues 23-272 of SEQ ID NO: 9.

In one or more embodiments, the antigen recognition region that recognizes, targets or specifically binds to the ErbB receptor family contains a fusion protein of natural T1E and Herin; wherein, the T1E consists of 7 amino acids at the N-terminus of human transcription growth factor α (TGFα) and 48 amino acids at the C-terminus of epidermal growth factor (EGF), preferably, the amino acid sequence of T1E is as shown in amino acid residues 23-77 of SEQ ID NO: 13; Herin is the 79 amino acids encoded by intron 8 in Herstatin, preferably, the amino acid sequence of Herin is as shown in amino acid residues 93-171 of SEQ ID NO: 13; preferably, the antigen recognition region is as shown in amino acid residues 23-171 of SEQ ID NO: 13.

In one or more embodiments, the amino acid sequence of the light chain variable region and the amino acid sequence of the heavy chain variable region of the single-chain antibody that recognizes, targets or specifically binds to mucin antigen are derived from an antibody against the amino acid sequence of the membrane-proximal end of Muc1, preferably, the amino acid sequence of the membrane-proximal end of Muc1 is as shown in SEQ ID NO: 24; preferably, the amino acid sequence of the light chain variable region of the single chain antibody is as shown in amino acid residues 23-133 of SEQ ID NO: 15, and/or the amino acid sequence of the heavy chain variable region is as shown in amino acid residues 149-269 of SEQ ID NO:15; preferably, the amino acid sequence of the single chain antibody is as shown in amino acid residues 23-269 of SEQ ID NO: 15.

In one or more embodiments, the antigen recognition region that recognizes, targets, or specifically binds to EGFR is a single chain antibody formed by the light chain variable region and the heavy chain variable region of an antibody specific for EGFR; preferably, the amino acid sequence of the light chain variable region of the single-chain antibody is as shown in amino acid residues 23-129 of SEQ ID NO: 17, and/or the amino acid sequence of the heavy chain variable region is as shown in amino acid residues 145-263 of SEQ ID NO: 17; preferably, the amino acid sequence of the single chain antibody is as shown in amino acid residues 23-263 of SEQ ID NO: 17.

In one or more embodiments, the chimeric antigen receptor contains, in the order from the N-terminus to the C-terminus, an optional signal peptide sequence, antigen recognition region, CD8a hinge region or IgG4 CH2CH3 hinge region, CD8 transmembrane region or CD28 transmembrane region, 4-1BB or CD28 intracellular domain and CD3 intracellular signal domain.

In one or more embodiments, the chimeric antigen receptor is selected from the group consisting of:

(1) a chimeric antigen receptor targeting CD19, with the amino acid sequence thereof is as shown in amino acid residues 22-486 of SEQ ID NO:7, or as shown in SEQ ID NO:7, and the coding sequence thereof is preferably as shown in nucleotide residues 64-1458 of SEQ ID NO:8, or as shown in SEQ ID NO: 8;

(2) a chimeric antigen receptor targeting mesothelin, with the amino acid sequence thereof is as shown in amino acid residues 23-681 of SEQ ID NO: 9, or as shown in SEQ ID NO: 9, the coding sequence thereof is preferably as shown in nucleotide residues 67-2043 of SEQ ID NO:10, or as shown in SEQ ID NO: 10, or the amino acid sequence thereof is as shown in amino acid residues 21-679 of SEQ ID NO: 11, or as shown in SEQ ID NO: 11, the coding sequence thereof is preferably as shown in nucleotide residues 61-2037 of SEQ ID NO: 12, or as shown in SEQ ID NO: 12;

(3) an antigen recognition region targeting ErbB family, with the amino acid sequence thereof is as shown in amino acid residues 23-580 of SEQ ID NO: 13, or as shown in SEQ ID NO: 13, and the coding sequence thereof is preferably as shown in nucleotide residues 67-1740 of SEQ ID NO:14, or as shown in SEQ ID NO: 14;

(4) a chimeric antigen receptor targeting mucin, with the amino acid sequence thereof is as shown in amino acid residues 23-678 of SEQ ID NO: 15, or as shown in SEQ ID NO: 15, and the coding sequence thereof is preferably as shown in nucleotide residues 67-2034 of SEQ ID NO:16, or as shown in SEQ ID NO: 16; and (5) a chimeric antigen receptor targeting EGFR, with the amino acid sequence thereof is as shown in amino acid residues 23-497 of SEQ ID NO: 17, or as shown in SEQ ID NO: 17, and the coding sequence thereof is preferably as shown in nucleotide residues 67-1491 of SEQ ID NO: 18, or as shown in SEQ ID NO: 18.

The present invention also provides an antibody, comprising an optional signal peptide, an antigen binding sequence, and a mutant Fc segment, wherein, the mutant Fc segment is a mutant Fc segment in which the amino acid residues at positions corresponding to positions 17 and 79 of the IgG4 Fc segment shown as SEQ ID NO: 25 are mutated to E and Q, respectively.

In one or more embodiments, the mutant Fc segment is a mutant IgG4 Fc segment, and its amino acid sequence is preferably as shown in amino acid residues 269-497 of SEQ ID NO: 1, preferably its coding sequence is as shown in nucleotide residues 805-1491 of SEQ ID NO: 2.

In one or more embodiments, the signal peptide is a light chain signal peptide, and its amino acid sequence is preferably as shown in amino acid residues 1-20 of SEQ ID NO: 1, preferably its coding sequence is as shown in nucleotide residues 1-60 of SEQ ID NO: 2.

In one or more embodiments, the antigen binding sequence is derived from an antibody or an antigen-binding fragment thereof that specifically binds to the antigen, such as a single-chain antibody, or from a ligand of a protein that functions in the tumor microenvironment or a fragment thereof that binds to the protein; preferably, the antibody is an agonistic antibody or an inhibitory antibody; preferably, the agonistic antibody is selected from antibodies directed against one or more of the following antigens: CD28, CD137, CD134, CD40, CD40L, ICOS, HVEM, CD2, CD27, CD30, GITR, LIGHT, DR3, SLAM, CD226, CD80 and CD86; preferably, the inhibitory antibody is selected from antibodies directed against one or more of the following antigens: PD-1, CTLA4, PDL1, PDL2, PDL3, TIM3, LAG3, CD47, BTLA, TIGIT, CD160, LAIR1, B7-H1, B7-1, VSIR and CD244; preferably, the ligand is a ligand of CD47.

In one or more embodiments, the agonistic antibody is a CD40 single chain antibody; preferably, the amino acid sequence of the light chain variable region of the CD40 single chain antibody is as shown in amino acid residues 21-146 of SEQ ID NO: 1, and/or the amino acid sequence of the heavy chain variable region of the CD40 single-chain antibody is as shown in amino acid residues 161-268 of SEQ ID NO: 1; preferably, the amino acid sequence of the CD40 single-chain antibody is as shown in amino acid residues 21-268 of SEQ ID NO: 1.

In one or more embodiments, the inhibitory antibody is a PD-1 single chain antibody; preferably, the amino acid sequence of the light chain variable region of the PD-1 single chain antibody is as shown in amino acid residues 21-131 of SEQ ID NO: 3, and/or the amino acid sequence of the heavy chain variable region of the PD-1 single-chain antibody is as shown in amino acid residues 147-266 of SEQ ID NO: 3; preferably, the amino acid sequence of the PD-1 single-chain antibody is as shown in amino acid residues 21-266 of SEQ ID NO: 3.

In one or more embodiments, the amino acid sequence of the CD47 ligand is shown as amino acid residues 21-138 of SEQ ID NO: 5.

In one or more embodiments, the coding sequence of the light chain variable region of the CD40 single-chain antibody is as shown in nucleotide residues 60-438 of SEQ ID NO: 2, and/or the coding sequence of the heavy chain variable region thereof may be as shown in nucleotide residues 481-804 of SEQ ID NO: 2; preferably, the coding sequence of the CD40 single chain antibody is shown as nucleotide residues 60-804 of SEQ ID NO: 2.

In one or more embodiments, the coding sequence of the light chain variable region of the PD-1 single-chain antibody is as shown in nucleotide residues 60-393 of SEQ ID NO: 4, and/or the coding sequence of the heavy chain variable region thereof is as shown in nucleotide residues 439-798 of SEQ ID NO: 4; preferably, the coding sequence of the PD-1 single chain antibody is shown as nucleotide residues 60-798 of SEQ ID NO: 4.

In one or more embodiments, the coding sequence of the CD47 ligand is shown as nucleotide residues 60-414 of SEQ ID NO: 6.

In one or more embodiments, the antibody is a CD40 antibody, PD-1 antibody, or CD47 antibody.

In one or more embodiments, the amino acid sequence of the CD40 antibody is as shown in amino acid residues 21-497 of SEQ ID NO: 1, or as shown in SEQ ID NO: 1, the amino acid sequence of the PD-1 antibody is as shown in amino acid residues 21-495 of SEQ ID NO: 3, or as shown in SEQ ID NO: 3, the amino acid sequence of the CD47 antibody is as shown in amino acid residues 21-367 of SEQ ID NO: 5, or as shown in SEQ ID NO: 5.

In one or more embodiments, the coding sequence of the antibody is as shown in nucleotide residues 60-1491 of SEQ ID NO: 2, or as shown in SEQ ID NO: 2; or is as shown in nucleotide residues 60-1485 of SEQ ID NO: 4, or as shown in SEQ ID NO: 4; or is as shown in nucleotide residues 60-1104 of SEQ ID NO: 6, or as shown in SEQ ID NO: 6.

Also provided is a nucleic acid sequence, selected from the group consisting of the coding sequences of the antibodies described herein or complementary sequences thereof.

Also provided is a nucleic acid construct containing the nucleic acid sequence described herein; preferably, the nucleic acid construct is an expression cassette or vector.

In one or more embodiments, the nucleic acid construct is an expression vector or an integration vector for incorporating the expression cassette into the genome of a host cell.

In one or more embodiments, the integration vector is an integration vector comprising a promoter, the coding sequence of the antibody described herein, and a polyA tailing signal sequence, in operable linkage between 5'LTR and 3'LTR, and not comprising a transposase coding sequence.

Also provided is a composition comprising the vector described herein and an optional transfection reagent; preferably, the composition comprises the integration vector described herein and an integration vector for incorporating an expression cassette of a chimeric antigen receptor into the genome of a host cell; preferably, the chimeric antigen receptor is as defined in any of the embodiments herein.

In one or more embodiments, in the composition, the mass ratio of the integration vector for incorporating the expression cassette of the chimeric antigen receptor into the genome of the host cell and the integration vector for incorporating the expression cassette of the antibody described herein into the genome of the host cell is 1-7:1-7, such as 1-5:1-5, preferably 1-3:1-3, more preferably 1-2:1-2, and even more preferably 1-2:1.

Also provided is a kit comprising the vector described herein and an optional transfection reagent; preferably, the kit comprises the integration vector for incorporating the expression cassette of the antibody described herein into the genome of the host cell and an integration vector for incorporating a expression cassette of a chimeric antigen receptor into the genome of a host cell; preferably, the chimeric antigen receptor is as defined in any of the embodiments herein;

In one or more embodiments, the kit contains the composition described herein.

Also provided is a pharmaceutical composition containing the T cells described herein or the T cells and the antibodies described herein expressed by the T cells.

Also provided is a host cell containing the nucleic acid sequence or nucleic acid construct described herein.

Also provided is the use of the T cells, antibodies, nucleic acid sequences, nucleic acid constructs, and host cells described herein in the preparation of a medicament for treating or preventing malignant tumors.

In one or more embodiments, the malignant tumor is selected from the group consisting of: acute B-lymphocytic leukemia, chronic B-lymphocytic leukemia, mantle cell lymphoma, non-Hodgkin's lymphoma, and multiple myeloma; or is a malignant tumor in which a cancer cell abnormally expresses mesothelin, at least one EGFR family member protein, a Muc1 antigen, EGFR and/or CD47 on cell surface; or is a malignant tumor mediated by CD40 or PD1.

Also provided is a method for preparing T cells, including the step of transfecting the T cells with the following vectors:

(1) the vector that is for transferring the expression cassette of the chimeric antigen receptor into the genome of the T cell and contains a transposase coding sequence, and (2) the vector that is for transferring the expression cassette of the antibody into the genome of the T cell and contains no transposase coding sequence;

preferably, the mass ratio of the vectors of (1) and (2) is 1-7:1-7, such as 1-5:1-5, preferably 1-3:1-3, more preferably 1-2: 1-2, more preferably 1-2:1.

BRIEF DESCRIPTION OF DRAWINGS

FIG. 14A shows the aging phenotype PD1, LAG3 and activated phenotype CD25, FIG. 14B shows the memory phenotype.

Figure 1:
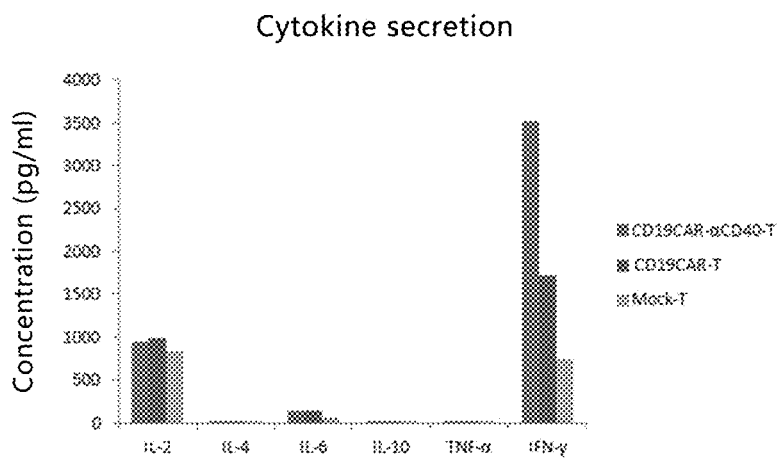
FIG. 1: Comparison of CD19CAR-secretion, changes of secretions of cytokines IL-2, IL-4, IL-6, IL-10, TNF-α and IFN-γ upon the stimulation of CD19 antigen.

In addition, the ordinates "count" in the Figures are "number of cells".

DETAILED DESCRIPTION

It should be understood that, within the scope of the present disclosure, the above technical features of the present disclosure and the technical features specifically described in the following (e.g., Examples) can be combined with each other, thereby forming preferred technical solution(s).

Some terms involved in the present disclosure will be explained below.

In the present disclosure, the term "expression cassette" refers to the complete elements required to express a gene, including an operably linked promoter and gene coding sequence.

The term "coding sequence" is defined herein as a part of a nucleic acid sequence that directly determines the amino acid sequence of its protein product (e.g., CAR, single chain antibody, hinge region, and transmembrane region). The boundaries of a coding sequence are usually determined by a ribosome binding site closely adjacent to the upstream of open reading frame at mRNA 5'end (for prokaryotic cells) and a transcriptional termination sequence closely adjacent to the downstream of the open reading frame at mRNA 3'end. The coding sequence can include, but is not limited to, DNA, cDNA and recombinant nucleic acid sequences.

The term "Fc" refers to the crystallizable fragment of an antibody, which means a peptide fragment located at the terminal of the "Y" handle structure of the antibody, comprising peptide segments of antibody heavy chain constant regions CH2 and CH3, which is the part of an antibody that interacts with effector molecule or cell.

The term "co-stimulating molecule" refers to a molecule that exists on the surface of an antigen-presenting cell, which is capable of binding to co-stimulating molecular receptors on Th cells to generate synergistic stimulation signals. The proliferation of lymphocyte not only requires binding of the antigen, but also the receiving of the co-stimulating molecule signal. The transmission of co-stimulation signal to T cell is mainly by the binding of co-stimulating molecules CD80 and CD86 expressed on the surface of an antigen-presenting cell to CD28 molecule on the surface of T cells. The receiving of co-stimulation signal by B cells can be mediated by common pathogen components such as LPS, or by complement component, or by CD40L on activated antigen-specific Th cell surface.

The term "linker" or hinge is a polypeptide fragment that links different proteins or polypeptides, and the purpose of which is to keep the independent spatial conformation of the linked protein or polypeptide to maintain the function or activity of the protein or polypeptide. Exemplary linkers include those containing G and/or S, and, for example, Furin 2A peptide.

The term "specific binding" refers to the reaction between an antibody or antigen binding fragment and an antigen which it recognizes. In certain embodiments, an antibody specifically binding to a certain antigen (or an antibody that is specific to a certain antigen) means that the antibody binds to the antigen with an affinity (Kd) of less than about $10^{-5}$M, such as less than about $10^{-6}$M, $10^{-7}$M, $10^{-8}$M, $10^{-9}$M or $10^{-19}$M or less. "Specific recognition" or "targeting" has a similar meaning.

The term "a pharmaceutically acceptable excipient" refers to a carrier and/or an excipient that are pharmacologically and/or physiologically compatible with a subject and active ingredient(s), which is well known in the art (see, for example, Remington's Pharmaceutical Sciences, Gennaro A R Ed., 19th edition, Pennsylvania: Mack Publishing Company, 1995), including but not limited to, pH adjusting agent, surfactant, adjuvant, ion strength enhancer. For example, the pH adjusting agent includes, but is not limited to, phosphate buffer; the surfactant includes, but is not limited to, cationic, anionic or non-ionic surfactant, such as Tween-80; the ion strength enhancer includes, but is not limited to, sodium chloride.

The term "an effective amount" refers to a dosage amount that can treat, prevent, reduce and/or alleviate the disease or condition of the present invention in a subject.

The term "disease and/or condition" refers to a physical state of the subject, wherein the physical state is related to the diseases and/or conditions of the disclosure.

The term "subject" or "patient" may refer to a patient or other animals, particularly a mammal, such as a human, a dog, a monkey, a cow, a horse and the like, that receives the pharmaceutical composition of the invention for treating, preventing, reducing and/or alleviating the diseases or conditions of the present invention.

"Chimeric antigen receptor" (CAR) is an artificially modified receptor which can anchor the specific molecules (such as antibodies) recognizing tumor cell surface antigens to immune cells (such as T cells), so that the immune cells can recognize tumor antigens or virus antigens and kill tumor cells or virus-infected cells. CARs generally in turn include an optional signal peptide, a polypeptide (such as a single chain antibody) that binds to a tumor cell membrane antigen, a hinge region, a transmembrane region, and an intracellular signal region. In general, the polypeptide that binds to a tumor cell membrane antigen can bind membrane antigens widely expressed by tumor cells with moderate affinity. The polypeptide that binds to a tumor cell membrane antigen may be a natural polypeptide or a synthetic polypeptide; preferably, the synthetic polypeptide is a single chain antibody or a Fab fragment.

The term "single chain antibody" (scFv) refers to an antibody fragment formed by linking the amino acid sequences of antibody light chain variable region ($V_L$ region) and heavy chain variable region ($V_H$ region) with hinge, which has antigen-binding ability. In certain embodiments, a single chain antibody of interest (scFv) is derived from the antibodies of interest. Antibodies of interest may be human antibodies, including human mouse chimeric antibodies and humanized antibodies. Antibodies may be secretory antibodies or membrane-anchored antibodies; preferably membrane-anchored antibodies.

The term "operably linked" or "in operably linkage" refers to DNA regulatory sequences (e.g., enhancers, promoters, etc.) linked to the coding sequence of the protein of interest in a manner that allows the coding sequence to be expressed.

1. Mutant Fc Segment

Studies have shown that the IgG4 Fc segments of PD-1 inhibitory antibodies and CD40 agonistic antibodies are easily recognized and phagocytized by monocytes/macrophages. In the present disclosure, the IgG4 Fc segments are modified by base mutation to make the antibodies expressed by T cells themselves can function well without causing ADCC effect.

In particular, the exemplary IgG4 Fc segment herein has the sequence shown in amino acid residues 269-497 of SEQ ID NO: 1, wherein, compared with the wild-type IgG4 Fc segment (SEQ ID NO: 25), the IgG4 Fc segment herein has a mutation from L to E at position 17, and a mutation from N to Q at position 79.

The present disclosure also includes Fc segments of other types of antibodies or immunoglobulins, with the mutation of the amino acid residue at position corresponding to position 17 of IgG4 Fc (SEQ ID NO: 25) to E and the mutation of the amino acid residue at position corresponding to position 79 to Q. The types of antibodies or immunoglobulins (Ig) include, but are not limited to, IgM, IgD, IgG, IgA, and IgE, which are well known in the art, wherein the IgG includes IgG1, IgG2, IgG3, and IgG4; IgA includes IgA1 and IgA2. Therefore, in certain embodiments, the present disclosure uses a mutant antibody Fc segment, wherein, the amino acid residue on the Fc segment at the position corresponding to the position 17 of IgG4 Fc segment shown in SEQ ID NO: 25 is E, and the amino acid residue at the position corresponding to position 79 is Q. In certain embodiments, the present disclosure uses mutant Fc segments of membrane-anchored Ig.

In certain embodiments, the present disclosure uses the Fc segment as shown in amino acid residues 269-497 of SEQ ID NO: 1, and its exemplary coding sequence may be as shown in nucleotide residues 805-1491 of SEQ ID NO: 2.

2. Antigen Binding Sequence

As used herein, the term "antigen-binding sequence" includes antibodies or antigen-binding fragments that specifically bind to antigens, such as single-chain antibodies, and also includes ligands of proteins that function in the tumor microenvironment or fragments thereof that bind to the proteins.

The antibodies expressed by CAR-T cells suitable for the present disclosure may be various antibodies used in tumor therapy, including agonistic antibodies and inhibitory antibodies.

The agonistic antibodies that can be used in the present disclosure may be various agonistic antibodies well known in the art, including but not limited to antibodies against one or more of the following antigens: CD28, CD137, CD134, CD40, CD40L, ICOS, HVEM, CD2, CD27, CD30, GITR, LIGHT, DR3, SLAM, CD226, CD80 and CD86. In certain embodiments, the agonistic antibody used in the present disclosure is an antibody against CD40. Preferably, the CD40 antibody is a single chain antibody. The amino acid sequence of the light chain variable region ($V_L$ region) of an exemplary CD40 single chain antibody is as shown in amino acid residues 21-146 of SEQ ID NO: 1, an exemplary coding sequence thereof is as shown in nucleotide residues 60-438 of SEQ ID NO: 2; the amino acid sequence of the heavy chain variable region of an exemplary CD40 single-chain antibody is as shown in amino acid residues 161-268 of SEQ ID NO: 1, an exemplary coding sequence thereof may be as shown in nucleotide residues 481-804 of SEQ ID NO: 2. The light chain variable region and the heavy chain variable region may be connected by a hinge region containing GS. An exemplary hinge region sequence may be as shown in amino acid residues 147-160 of SEQ ID NO: 1. In certain embodiments, the amino acid sequence of the CD40 single-chain antibody suitable herein is as shown in amino acid residues 21-268 of SEQ ID NO: 1, and its exemplary coding sequence may be as shown in nucleotide residues 60-804 of SEQ ID NO: 2.

Inhibitory antibodies useful in the present disclosure include, but are not limited to, immune checkpoint inhibitory antibodies known in the art, such as antibodies against one or more of the following antigens: PD-1, CTLA4, PDL1, PDL2, PDL3, TIM3, LAG3, CD47, BTLA, TIGIT, CD160, LAIR1, B7-H1, B7-1, VSIR and CD244. In certain embodiments, the inhibitory antibody used in the present disclosure is an antibody against PD-1 or CD47. In certain embodiments, the PD-1 antibody is a single chain antibody. The amino acid sequence of the light chain variable region ($V_L$ region) of an exemplary PD-1 single chain antibody is as shown in amino acid residues 21-131 of SEQ ID NO: 3, an exemplary coding sequence thereof is as shown in nucleotide residues 60-393 of SEQ ID NO: 4; the amino acid sequence of the heavy chain variable region of an exemplary PD-1 single-chain antibody is as shown in amino acid residues 147-266 of SEQ ID NO: 3, an exemplary coding sequence thereof may be as shown in nucleotide residues 439-798 of SEQ ID NO: 4. The light chain variable region and the heavy chain variable region may be connected by a hinge region containing GS. An exemplary hinge region sequence may be as shown in amino acid residues 132-146 of SEQ ID NO: 3. In certain embodiments, the amino acid sequence of the PD-1 single-chain antibody suitable herein is as shown in amino acid residues 21-266 of SEQ ID NO: 3, and its exemplary coding sequence may be as shown in nucleotide residues 60-798 of SEQ ID NO: 4.

In certain embodiments, the antigen-binding sequence used herein is a ligand for proteins that function in the tumor microenvironment (e.g., related to the growth, migration and phagocytosis escaping of tumor cells, etc.), especially a ligand of proteins expressed on the surface of cancer cells, such as CD47. In certain embodiments, the amino acid sequence of the CD47 ligand is as shown in amino acid residues 21-138 of SEQ ID NO: 5, and its exemplary coding sequence may be as shown in nucleotide residues 60-414 of SEQ ID NO: 6.

3. Antibodies Expressed by CAR-T Cells

In the present disclosure, antibodies expressed by CAR-T cells usually contain the antigen-binding sequence described herein and the mutant Fc segment. The two can be directly connected, or can be connected by suitable linkers.

In certain embodiments, the antibodies of the disclosure contain optional signal peptides, agonistic or inhibitory antibodies, and mutant Fc segments described herein. For example, the antibody of the disclosure may contain an optional signal peptide, an antibody against an antigen selected from the following antigens, and the mutant Fc segments described herein: CD28, CD137, CD134, CD40, CD40L, ICOS, HVEM, CD2, CD27, CD30, GITR, LIGHT, DR3, SLAM, CD226, CD80 and CD86. Alternatively, the antibody of the present disclosure may contain an optional signal peptide, an antibody against an antigen selected from the following antigens, and the mutant Fc segments described herein: PD-1, CTLA4, PDL1, PDL2, PDL3, TIM3, LAG3, CD47, BTLA, TIGIT, CD160, LAIR1, B7-H1, B7-1, VSIR and CD244. Preferably, the antigen-binding sequence is a single-chain antibody formed by a light chain variable region and a heavy chain variable region of an antibody against the antigen, or the ligand of a protein expressed on the surface of a cancer cell.

In certain embodiments, the antibody further includes a signal peptide sequence. The signal peptide is a short peptide chain (5-30 amino acids in length) that guides the transfer of newly synthesized proteins to the secretory pathway, which often refers to the amino acid sequence at the N-terminus (sometimes not necessarily the N-terminus) of the newly synthesized polypeptide chains and used to guide the transmembrane transfer (location) of proteins, by directing proteins to subcellular organelles having different membrane structures. The signal peptide may be a secretory signal peptide or a membrane-bound signal peptide.

Any suitable signal peptide sequence can be used in the present disclosure. In certain embodiments, the signal peptide may be a CD8 signal peptide, a CD28 signal peptide, a CD4 signal peptide, or a light chain signal peptide. In certain embodiments, the signal peptide in the antibody of the present disclosure is the light chain signal peptide, and its exemplary amino acid sequence may be as shown in amino acid residues 1-20 of SEQ ID NO: 1, and an exemplary coding sequence may be as shown in nucleotide residues 1-60 of SEQ ID NO: 2. In certain embodiments, the signal peptide in the antibody of the present disclosure is the CD8 signal peptide, its exemplary amino acid sequence may be as shown in amino acid residues 1-21 of SEQ ID NO: 7, its exemplary coding sequence may be as shown in nucleotide residues 1-63 of SEQ ID NO: 8; or, its exemplary amino acid sequence may be as shown in amino acid residues 1-22 of SEQ ID NO: 9, its exemplary coding sequence may be as shown in nucleotide residues 1-66 of SEQ ID NO: 10.

In certain embodiments, the antibody of the disclosure is the CD40 antibody, which contains an optional signal peptide, a CD40 single chain antibody, and the mutant Fc segment described herein; preferably, the signal peptide is a light chain signal peptide; preferably, the amino acid sequence of the light chain variable region ($V_L$ region) of the CD40 single chain antibody is as shown in amino acid residues 21-146 of SEQ ID NO: 1, an exemplary coding sequence thereof is as shown in nucleotide residues 60-438 of SEQ ID NO: 2; preferably, the amino acid sequence of the heavy chain variable region ($V_H$ region) of the CD40 single-chain antibody is as shown in amino acid residues 161-268 of SEQ ID NO:1, an exemplary coding sequence thereof may be as shown in nucleotide residues 481-804 of SEQ ID NO: 2. In certain embodiments, the amino acid sequence of the CD40 single-chain antibody is as shown in amino acid residues 21-268 of SEQ ID NO: 1, and its exemplary coding sequence may be as shown in nucleotide residues 60-804 of SEQ ID NO: 2. In certain embodiments, the amino acid sequence of the mutant Fc segment is as shown in amino acid residues 269-497 of SEQ ID NO: 1, and its exemplary coding sequence may be as shown in nucleotide residues 805-1491 of SEQ ID NO: 2. In certain embodiments, the amino acid sequence of the CD40 antibody of the present disclosure is as shown in amino acid residues 21-497 of SEQ ID NO: 1, or as shown in SEQ ID NO: 1, and its exemplary coding sequence is as shown in nucleotide residues 60-1491 of SEQ ID NO: 2, or is as shown in SEQ ID NO: 2.

In certain embodiments, the antibody of the disclosure is the PD-1 antibody, which contains an optional signal peptide, a PD-1 single chain antibody, and the mutant Fc segment described herein; preferably, the signal peptide is a light chain signal peptide; preferably, the amino acid sequence of the light chain variable region (VL region) of the PD-1 single chain antibody is as shown in amino acid residues 21-131 of SEQ ID NO: 3, an exemplary coding sequence thereof is as shown in nucleotide residues 60-393 of SEQ ID NO: 4; preferably, the amino acid sequence of the heavy chain variable region ($V_H$ region) of the PD-1 single-chain antibody is as shown in amino acid residues 147-266 of SEQ ID NO: 3, an exemplary coding sequence thereof may be as shown in nucleotide residues 439-798 of SEQ ID NO: 4. In certain embodiments, the amino acid sequence of the PD-1 single-chain antibody is as shown in amino acid residues 21-266 of SEQ ID NO: 3, and its exemplary coding sequence may be as shown in nucleotide residues 60-798 of SEQ ID NO: 4. In certain embodiments, the amino acid sequence of the mutant Fc segment is as shown in amino acid residues 267-495 of SEQ ID NO: 3, and its exemplary coding sequence may be as shown in nucleotide residues 799-1485 of SEQ ID NO: 2. In certain embodiments, the amino acid sequence of the PD-1 antibody of the present disclosure is as shown in amino acid residues 21-495 of SEQ ID NO: 3, or as shown in SEQ ID NO: 3, and its exemplary coding sequence is as shown in nucleotide residues 60-1485 of SEQ ID NO: 4, or is as shown in SEQ ID NO: 4.

In certain embodiments, the antibody of the disclosure is a CD47 antibody, which contains an optional signal peptide, the ligand sequence of CD47, and the mutant Fc segment described herein; preferably, the signal peptide is the light chain signal peptide; preferably, the amino acid sequence of the ligand is as shown in amino acid residues 21-138 of SEQ ID NO: 5, and its exemplary coding sequence is as shown in the nucleotide residues 60-414 of SEQ ID NO: 6. In certain embodiments, the amino acid sequence of the mutant Fc segment is as shown in amino acid residues 139-367 of SEQ ID NO: 5, and its exemplary coding sequence may be as shown in nucleotide residues 415-1101 of SEQ ID NO: 6. In certain embodiments, the amino acid sequence of the CD47 antibody of the present disclosure is as shown in amino acid residues 21-367 of SEQ ID NO: 5, or as shown in SEQ ID NO: 5, and its exemplary coding sequence is as shown in nucleotide residues 60-1104 of SEQ ID NO: 6, or is as shown in SEQ ID NO: 6.

4. Chimeric Antigen Receptor (CAR)

The present invention relates to any chimeric antigen receptor that can be expressed in T cells, including but not limited to those recognize, target, or specifically bind to one or more of the following antigens: CD19, CD20, CEA, GD2 (also known as B4GALNT1, β1,4-acetyl-aminogalactosyl-transferase 1), FR (Flavin reductase), PSMA (prostate specific membrane antigen), PMEL (premelanosome protein), CA9 (carbonic anhydrase IX), CD171/L1-CAM, IL-13Rα2, MART-1 (also known as mucin-A), ERBB2, NY-ESO-1 (also known as CTAG1B, cancer/testis antigen 1B), MAGE (melanoma-associated antigen E1) family proteins, BAGE (B melanoma antigen family) family proteins, GAGE (growth hormone releasing factor) family proteins, AFP (α-fetoprotein), MUC1 (mucin 1, cell surface related), CD22, CD23, CD30, CD33, CD44v7/8, CD70, VEGFR1, VEGFR2, IL-11Rα, EGP-2, EGP-40, FBP, GD3 (also known as ST8SIA1, ST8α-N-acetyl-ceramide α-2,8-sialic acid convertase 1), PSCA (prostate stem cell antigen), FSA (also known as KIAA1109), PSA (also known as KLK3, kallikrein-related peptidase 3), HMGA2, fetal acetylcholine receptor, LeY (also known as FUT3), EpCAM, MSLN (mesothelin), IGFR1, EGFR, EGFRvIII, ERBB3, ERBB4, CA125 (also known as MUC16, mucin 16, cell surface related), CA15-3, CA19-9, CA72-4, CA242, CA50, CYFRA21-1, SCC (also known as SERPINB3), AFU (also known as FUCA1), EBV-VCA, POA (also known as VDR, vitamin D (1,25-dihydrovitamin D3) receptor), β2-MG (β-2-microglobulin) and PROGRP (GRP gastrin releasing peptide).

The chimeric antigen receptor of the present invention usually contains an optional signal peptide sequence, antigen recognition region, hinge region, transmembrane region, intracellular co-stimulatory signal domain and intracellular signal domain.

The signal peptides suitable for the chimeric antigen receptor herein may be as described above, and may be secretory signal peptides or membrane-bound signal peptides, including but not limited to CD8 signal peptide, CD28 signal peptide, CD4 signal peptide and a light chain signal peptide. In certain embodiments, the signal peptide in the chimeric antigen receptor of the present disclosure is a light chain signal peptide, and its exemplary amino acid sequence may be as shown in amino acid residues 1-20 of SEQ ID NO: 11, and an exemplary coding sequence may be as shown in nucleotide residues 1-60 of SEQ ID NO: 12. In certain embodiments, the signal peptide in the antibody of the present disclosure is the CD8 signal peptide, its exemplary amino acid sequence may be as shown in amino acid residues 1-21 of SEQ ID NO: 7, its exemplary coding sequence may be as shown in nucleotide residues 1-63 of SEQ ID NO: 8; or, its exemplary amino acid sequence may be as shown in amino acid residues 1-22 of SEQ ID NO: 9, its exemplary coding sequence may be as shown in nucleotide residues 1-66 of SEQ ID NO: 10.

The antigen recognition region may be a single chain antibody (scFv). The single chain antibody may be a scFv commonly used in the art that recognizes a target antigen, including but not limited to the scFv formed by the light chain variable region and heavy chain variable region of an antibody that recognizes, targets, or specifically binds to one or more of the aforementioned antigens. In certain embodiments, the amino acid sequence of the present disclosure that recognizes the target antigen is a single chain antibody that recognizes, targets, or specifically binds to CD19, mesothelin, EGFR, or mucin. In certain embodiments, the antigen recognition region of the disclosure consists of amino acid sequences that target the ErbB receptor family.

For example, the amino acid sequence of the light chain variable region of an exemplary single-chain antibody that recognizes CD19 may be as shown in amino acid residues 22-128 of SEQ ID NO: 7, and its exemplary coding sequence may be as shown in nucleotide residues 64-384 of SEQ ID NO: 8. For example, the amino acid sequence of the heavy chain variable region of an exemplary single-chain antibody that recognizes CD19 may be as shown in amino acid residues 144-263 of SEQ ID NO: 7, and its exemplary coding sequence may be as shown in nucleotide residues 430-789 of SEQ ID NO: 8. In certain embodiments, the amino acid sequence of an exemplary single-chain antibody that recognizes CD19 is as shown in amino acid residues 22-263 of SEQ ID NO: 7, and its exemplary coding sequence may be as shown in nucleotide residues 64-789 of SEQ ID NO: 8.

An exemplary scFv that recognizes mesothelin antigen may be a single chain antibody well known in the art against mesothelin antigen. Preferably, the amino acid sequences of the light chain variable region and the heavy chain variable region of the single-chain antibody are derived from an antibody against the amino acid sequence of the membrane-proximal end of mesothelin. Preferably, the anti-mesothelin single chain antibody described herein is a single chain antibody against Region I or III of mesothelin. Preferably, the amino acid sequences of the light chain variable region and the heavy chain variable region of the single-chain antibody are derived from an antibody against the amino acid sequence of Region I or III of mesothelin. In some embodiments, the amino acid sequence of mesothelin Region I is as shown in SEQ ID NO: 21; the amino acid sequence of mesothelin Region III is as shown in SEQ ID NO: 22. The amino acid sequence of an exemplary anti-mesothelin Region I single-chain antibody is as shown in SEQ ID NO: 23. The amino acid sequence of the light chain variable region of an exemplary single chain antibody against mesothelin Region III is as shown in amino acid residues 23-146 of SEQ ID NO: 9, an exemplary coding sequence thereof is as shown in nucleotide residues 67-438 of SEQ ID NO: 10; the amino acid sequence of the heavy chain variable region of an exemplary single chain antibody against mesothelin Region III is as shown in amino acid residues 162-272 of SEQ ID NO: 9, an exemplary coding sequence thereof may be as shown in nucleotide residues 484-816 of SEQ ID NO: 10. In certain embodiments, the amino acid sequence of the scFv that recognizes mesothelin antigen is as shown in amino acid residues 23-272 of SEQ ID NO: 9, and its exemplary coding sequence may be as shown in nucleotide residues 67-816 of SEQ ID NO: 10. Herein, unless otherwise specified, mesothelin refers to the mesothelin fragment anchored on the membrane.

In the present disclosure, an exemplary antigen recognition region targeting the ErbB receptor family contains a fusion protein of the natural TIE and Herin. Herein, TIE is a chimeric polypeptide consisting of 7 amino acids at the N-terminus of human transcription growth factor α (TGFα) and 48 amino acids at the C-terminus of epidermal growth factor (EGF). Preferably, the amino acid sequence of the TIE is as shown in amino acid residues 23-77 of SEQ ID NO: 13, and its exemplary coding sequence may be as shown in nucleotide residues 67-231 of SEQ ID NO: 14. Herein, Herin is the 79 amino acids encoded by intron 8 in Herstatin. Preferably, the amino acid sequence of Herin is as shown in amino acid residues 93-171 of SEQ ID NO: 13. In the present disclosure, the codons encoding amino acids of Herin are optimized. Therefore, the preferred nucleotide sequence of Herin of the present disclosure is as shown in the nucleotide residues 277-513 of SEQ ID NO: 14. Generally, TIE and Herin can be connected by a rigid linker sequence. An example of a rigid linker sequence is two or more repeats of EAAAK, also referred to herein as the EAAAK linker. In certain embodiments, an exemplary rigid linker sequence is as shown in amino acid residues 78-92 of SEQ ID NO: 13, and its exemplary coding sequence may be as shown in nucleotide residues 232-276 of SEQ ID NO: 14. In certain embodiments, the antigen recognition region described herein is as shown in amino acid residues 23-171 of SEQ ID NO: 13, and its exemplary coding sequence may be as shown in nucleotide residues 67-513 of SEQ ID NO: 14.

In the present disclosure, an exemplary antigen recognizing region that recognizes mucin (Muc1) antigen may be a scFv of mucin, and the single chain antibody may be a single chain antibody well known in the art against Muc1 antigen. In certain embodiments, the amino acid sequences of the light chain variable region and the heavy chain variable region of the single chain antibody are derived from an antibody against the amino acid sequence of the membrane-proximal end of Muc1. In certain embodiments, the amino acid sequence of the membrane-proximal end of Muc1 is as shown in SEQ ID NO: 24. The amino acid sequence of the light chain variable region of an exemplary anti-Muc1 single-chain antibody may be as shown in amino acid residues 23-133 of SEQ ID NO: 15, and its exemplary coding sequence may be as shown in nucleotide residues 67-399 of SEQ ID NO: 16. The amino acid sequence of the heavy chain variable region of an exemplary anti-Muc1 single-chain antibody may be as shown in amino acid residues 149-269 of SEQ ID NO: 15, and its exemplary coding sequence may be as shown in nucleotide residues 445-809 of SEQ ID NO: 16. In certain embodiments, the amino acid sequence of an exemplary single-chain antibody that recognizes mucin antigen is as shown in amino acid residues 23-269 of SEQ ID NO: 15, and its exemplary coding sequence may be as shown in nucleotide residues 67-807 of SEQ ID NO: 16.

Herein, the antigen recognition region that recognizes EGFR may be a single chain antibody formed by the light chain variable region and the heavy chain variable region of an antibody specific for EGFR, and the single chain antibody may be a single chain antibody well known in the art against EGFR. The amino acid sequence of the light chain variable region of an exemplary single-chain antibody that recognizes EGFR may be as shown in amino acid residues 23-129 of SEQ ID NO: 17, and its exemplary coding sequence may be as shown in nucleotide residues 67-387 of SEQ ID NO: 18. The amino acid sequence of the heavy chain variable region of an exemplary single-chain antibody that recognizes EGFR may be as shown in amino acid residues 145-263 of SEQ ID NO: 17, and its exemplary coding sequence may be as shown in nucleotide residues 433-789 of SEQ ID NO: 18. In certain embodiments, the amino acid sequence of an exemplary single-chain antibody that recognizes EGFR is as shown in amino acid residues 23-263 of SEQ ID NO: 17, and its exemplary coding sequence may be as shown in nucleotide residues 67-789 of SEQ ID NO: 18.

In this article, the hinge region refers to the region between the CH1 and CH2 functional regions of the immunoglobulin heavy chain. The hinge region is rich in proline, does not form an alpha helix, and is prone to stretching and distortion to a certain degree, which facilitates the complementary binding between the antigen binding site of the antibody and the epitope. The hinge region suitable herein may be selected from any one or more of the group consisting of an extracellular hinge region of CD8, an IgG1 Fc CH2CH3 hinge region, a IgD hinge region, a extracellular hinge region of CD28, a IgG4 Fc CH2CH3 hinge region and a extracellular hinge region of CD4. The hinge region is preferably a hinge region having 50 or more amino acid residues in length, more preferably 80 or more amino acid residues in length. In certain embodiments, the CD8α hinge region or IgG4 Fc CH2CH3 hinge region is used herein. In certain embodiments, the amino acid sequence of the CD8α hinge region is as shown in amino acid residues 264-308 of SEQ ID NO: 7, and its exemplary coding sequence is shown in nucleotide residues 790-924 of SEQ ID NO: 8; in other embodiments, the amino acid sequence of CD8α hinge region is as shown in amino acid residues 264-318 of SEQ ID NO: 17, and its exemplary coding sequence is as shown in nucleotide residues 790-954 of SEQ ID NO: 18. The amino acid sequence of an exemplary IgG4 CH2CH3 hinge region is as shown in amino acid residues 273-500 of SEQ ID NO: 9, and its exemplary coding sequence may be as shown in nucleotide residues 817-1500 of SEQ ID NO: 10.

The transmembrane region may be one of the CD28 transmembrane region, the CD8 transmembrane region, the CD3ζ transmembrane region, the CD134 transmembrane region, the CD137 transmembrane region, the ICOS transmembrane region, and the DAP10 transmembrane region. In certain embodiments, the transmembrane region is the CD8 transmembrane region, and its exemplary amino acid sequence is as shown in amino acid residues 309-332 of SEQ ID NO:7, and its exemplary coding sequence is as shown in nucleotide residues 925-996 of SEQ ID NO: 8. In certain embodiments, the amino acid sequence of the CD8 transmembrane region is as shown in amino acid residues 319-344 of SEQ ID NO: 17, and its exemplary coding sequence may be as shown in nucleotide residues 955-1032 of SEQ ID NO: 18. In certain embodiments, the transmembrane region is the CD28 transmembrane region, and its amino acid sequence is as shown in amino acid residues 501-528 of SEQ ID NO: 9, and its coding sequence is as shown in nucleotide residues 1501-1584 of SEQ ID NO: 10.

The intracellular co-stimulatory signal domain includes the intracellular domain of the co-stimulatory signal molecule, which can be selected from the group consisting of a intracellular domains of CD28, a CD134/OX40, CD137/4-1BB, a lymphocyte-specific protein tyrosine kinase (LCK), a inducible T cell co-stimulatory factor (ICOS) and a DNAX activating protein 10 (DAP10). In certain embodiments, the intracellular domain of the co-stimulatory signaling molecule is the intracellular domain of CD137/4-1BB; preferably, the amino acid sequence of the CD137/4-1BB is as shown in the amino acid residues 333-374 of SEQ ID NO: 7, and its exemplary coding sequence is as shown in the nucleotide residues 997-1122 of SEQ ID NO: 8. In certain embodiments, the intracellular co-stimulatory signal domain is the CD28 intracellular region, and its exemplary amino acid sequence is as shown in amino acid residues 529-569 of SEQ ID NO: 9, and its exemplary coding sequence is as shown in nucleotide residues 1585-1707 of SEQ ID NO: 10.

The intracellular signal domain is preferably an immunoreceptor tyrosine activation motif, which may be the CD3ζ intracellular signal domain or FcεRIγ intracellular signal domain; preferably is the CD3ζ intracellular signal domain, preferably the amino acid sequence of the CD3ζ intracellular signal domain is as shown in the amino acid residues 375-486 of SEQ ID NO: 7, its exemplary coding sequence may be as shown in the nucleotide residues 1123-1458 of SEQ ID NO: 8.

In certain embodiments, the chimeric antigen receptor herein contains, in the order from the N-terminus to the C-terminus, an optional signal peptide sequence, antigen recognition region, CD8a hinge region or IgG4 CH2CH3 hinge region, CD8 transmembrane region or CD28 transmembrane region, 4-1BB or CD28 intracellular domain and CD3ζ intracellular signal domain. Preferably, the chimeric antigen receptor of the present disclosure is: a chimeric antigen receptor targeting CD19, with the amino acid sequence thereof is as shown in amino acid residues 22-486 of SEQ ID NO:7, or as shown in SEQ ID NO:7, and the exemplary coding sequence thereof is as shown in nucleotide residues 64-1458 of SEQ ID NO:8, or as shown in SEQ ID NO: 8; a chimeric antigen receptor targeting mesothelin, with the amino acid sequence thereof is as shown in amino acid residues 23-681 of SEQ ID NO: 9, or as shown in SEQ ID NO: 9, the exemplary coding sequence thereof is as shown in nucleotide residues 67-2043 of SEQ ID NO: 10, or as shown in SEQ ID NO: 10, or the amino acid sequence thereof is as shown in amino acid residues 21-679 of SEQ ID NO: 11, or as shown in SEQ ID NO: 11, the exemplary coding sequence thereof is as shown in nucleotide residues 61-2037 of SEQ ID NO: 12, or as shown in SEQ ID NO: 12; an antigen recognition region targeting ErbB family, with the amino acid sequence thereof is as shown in amino acid residues 23-580 of SEQ ID NO: 13, or as shown in SEQ ID NO:13, and the exemplary coding sequence thereof is as shown in nucleotide residues 67-1740 of SEQ ID NO:14, or as shown in SEQ ID NO: 14; a chimeric antigen receptor targeting mucin, with the amino acid sequence thereof is as shown in amino acid residues 23-678 of SEQ ID NO: 15, or as shown in SEQ ID NO:15, and the exemplary coding sequence thereof is as shown in nucleotide residues 67-2034 of SEQ ID NO: 16, or as shown in SEQ ID NO: 16; or a chimeric antigen receptor targeting EGFR, with the amino acid sequence thereof is as shown in amino acid residues 23-497 of SEQ ID NO: 17, or as shown in SEQ ID NO: 17, and the exemplary coding sequence thereof is as shown in nucleotide residues 67-1491 of SEQ ID NO: 18, or as shown in SEQ ID NO: 18.

The above elements forming the chimeric antigen receptor herein, such as the signal peptide, the light chain variable region and heavy chain variable region of the single chain antibody against Muc1, the hinge region, the transmembrane region, the intracellular co-stimulatory signal domain and the intracellular signal domains, etc., can be directly connected to each other, or can be connected by linker sequences. The linker sequence may be a linker sequence known in the art suitable for antibodies, for example, a linker sequence containing G and S. The linker may be 3-25 amino acid residues in length, for example, 3-15, 5-15, 10-20 amino acid residues. In certain embodiments, the linker sequence is a polyglycine linker sequence. The number of glycine in the linker sequence is not particularly limited, but is usually 2-20, such as 2-15, 2-10, 2-8. In addition to glycine and serine, the linker can also contain other known amino acid residues, such as alanine (A), leucine (L), threonine (T), glutamic acid (E), phenylalanine (F), arginine (R), glutamine (Q), etc.

5. Nucleic Acid Sequence, Nucleic Acid Construct and Vector and Preparation Method Thereof The invention also includes a nucleic acid sequence, selected from the group consisting of the coding sequences of the antibodies described herein or complementary sequences thereof. The nucleic acid sequence may be in the form of DNA or RNA. DNA can be single-stranded or double-stranded.

More specifically, the present disclosure includes the coding sequence of an antibody containing an optional signal peptide, the antigen binding sequence described herein, and the mutant Fc segment, or a complementary sequence thereof. Exemplary coding sequences include but are not limited to the coding sequence as shown in SEQ ID NO: 2 or its nucleotide residues 60-1491; the coding sequence as shown in SEQ ID NO: 4 or its nucleotide residues 60-1485; and the coding sequence as shown in SEQ ID NO: 6 or its nucleotide residues 60-1104.

The disclosure also includes the coding sequences of chimeric antigen receptors described herein, or complementary sequences thereof. The coding sequence of an exemplary chimeric antigen receptor includes the coding sequence that codes the chimeric antigen receptor containing, in the order from the N-terminus to the C-terminus, an optional signal peptide sequence, antigen recognition region, CD8α hinge region or IgG4 CH2CH3 hinge region, CD8 transmembrane region or CD28 transmembrane region, the intracellular domain of 4-1BB or CD28 and the intracellular signal domain of CD3ζ. Exemplary coding sequences include the coding sequence as shown in SEQ ID NO: 8 or its nucleotide residues 64-1458, the coding sequence as shown in SEQ ID NO: 10 or its nucleotide residues 67-2043, the coding sequence as shown in SEQ ID NO: 12 or its nucleotide residues 67-2037, the coding sequence as shown in SEQ ID NO: 14 or its nucleotide residues 67-1740, the coding sequence as shown in SEQ ID NO: 16 or its nucleotide residues 67-2034, and the coding sequence as shown in SEQ ID NO: 18 or its nucleotide residues 67-1491.

The present disclosure also includes nucleic acid constructs containing the coding sequence of the antibody or chimeric antigen receptor of the present disclosure, or a complementary sequence thereof.

In certain embodiments, the nucleic acid construct is an expression cassette that contains operably linked: a promoter sequence, the coding sequence of an antibody or chimeric antigen receptor or complementary sequence thereof, and optionally a polyA tailing signal sequence. The promoter sequence is usually operably linked to the coding sequence described herein. The promoter can be any nucleotide sequence having transcriptional activity in the selected host cell, including mutant, truncated, and hybrid promoters, which can be obtained from a gene encoding an extracellular or intracellular polypeptide that is homologous or heterologous to the host cell. The expression cassette usually contains a transcription terminator sequence, which is recognized by the host cell to terminate transcription. The terminator sequence is operably linked to the 3'end of the coding sequence described herein. Any terminator that is functional in the selected host cell may be used in the present disclosure.

In certain embodiments, the nucleic acid construct is a vector. Different vectors include but are not limited to plasmids, phagemids, phage derivatives, animal viruses and cosmids. The vector may be an expression vector, preferably a eukaryotic expression vector. The expression vector can be provided to the cell as a viral vector. Viruses that can be used as vectors include, but are not limited to retroviruses, adenoviruses, adeno-associated viruses, herpes viruses, and lentiviruses. The vector may also be an integration vector for integrating the coding sequence or its complementary sequence into the host cell.

Generally, suitable vectors contain a replication origin that functions in at least one organism, promoter sequences, convenient restriction enzyme sites, and one or more selectable markers. For example, in certain embodiments, the present disclosure uses a retroviral vector that contains a replication initiation site, 3'LTR, 5'LTR, the coding sequence of the antibody or chimeric antigen receptor described herein, and optional selectable markers.

Here, suitable promoters include, but are not limited to, the immediate early cytomegalovirus (CMV) promoter sequence. Such promoter sequence is a strong constitutive promoter sequence capable of driving high-level expression of any polynucleotide sequence operably linked thereto. Another example of a suitable promoter is elongation growth factor-1α (EF-1α). However, other constitutive promoter sequences can also be used, including but not limited to simian virus 40 (SV40) early promoter, mouse breast cancer virus (MMTV), human immunodeficiency virus (HIV) long terminal repeat (LTR) promoter, MoMuLV promoter, avian leukemia virus promoter, EB virus immediate early promoter, Ruth's sarcoma virus promoter, and human gene promoters, such as but not limited to actin promoter, myosin promoter, heme promoter and creatine kinase promoter. Furthermore, inducible promoters may also be considered. The use of an inducible promoter provides a molecular switch that can turn on the expression of a polynucleotide sequence operably linked to the inducible promoter when desired, and turn off the expression when expression is undesirable. Examples of inducible promoters include, but are not limited to, metallothionein promoter, glucocorticoid promoter, progesterone promoter, and tetracycline promoter.

In some embodiments, various promoter sequences published in CN201510021408.1 can be used herein, including but not limited to: CCEF promoter as shown in SEQ ID NO: 5 of the application, comprising mCMV enhancer, hCMV enhancer, and EF1a promoter; TCEF promoter as shown in SEQ ID NO: 7, comprising CD3e enhancer, mCMV enhancer, hCMV enhancer and EF1α promoter; CCEFI promoter as shown in SEQ ID NO: 8, comprising mCMV enhancer, hCMV enhancer and intron-containing EF1α promoter; TEFI promoter as shown in SEQ ID NO: 3, comprising CD3e enhancer and intron-containing EF1α promoter; and TCEFI promoter as shown in SEQ ID NO: 3, comprising CD3e enhancer, mCMV enhancer, hCMV enhancer and intron-containing EF1a promoter. The entire contents of this application are incorporated herein by reference.

Selectable markers include either or both of selectable marker genes and reporter genes, which facilitate identification and selection of the expressing cells from a population of cells infected with viral vectors. Useful selectable marker genes include, for example, antibiotic resistance genes, such as neo and the like. Suitable reporter genes may include genes encoding luciferase, β-galactosidase, chloramphenicol acetyltransferase, secreted alkaline phosphatase, or green fluorescent protein genes.

In certain embodiments, the coding sequence of the chimeric antigen receptor and the coding sequence of the antibody described herein can be cloned separately into vectors (also called integration vectors), especially transposition vectors, for integrating the nucleic acid sequences of interest into the genome of the host cell. In certain embodiments, the transposition vector is a eukaryotic expression vector containing a transposition element selected from the group consisting of piggybac, sleeping beauty, frog prince, Tn5, or Ty. Such transposition vectors contain the 5' inverted terminal repeat (5'LTR) of the corresponding transposon and the 3' inverted terminal repeat (3'LTR) of the corresponding transposon. The transposase may be a transposase from a piggybac, sleeping beauty, frog prince, Tn5 or Ty transposition system. If a transposase from a different transposition system is used, the sequences of 5'LTR and 3'LTR in the vector are also changed accordingly into sequences suitable for the transposition system, which can be easily determined by those skilled in the art. In certain embodiments, the expression cassette of the CAR or antibody of the present disclosure is located between 5'LTR and 3'LTR, the expression cassette including the corresponding promoter sequence, the coding sequence of the CAR or antibody, and a polyA tailed signal sequence.

In certain embodiments, the transposase is a transposase from the piggybac transposition system. Therefore, in these embodiments, the 5' inverted terminal repeat sequence and the 3' inverted terminal repeat sequence of the transposon are the 5' inverted terminal repeat sequence and the 3' inverted terminal repeat sequence of the piggybac transposon, respectively. In certain embodiments, the transposon 5' inverted terminal repeat sequence is shown in SEQ ID NO: 1 of CN201510638974.7 (the contents of which are incorporated herein by reference). In certain embodiments, the 3' inverted terminal repeat sequence of the transposon is shown in SEQ ID NO: 4 of CN 201510638974.7. In certain embodiments, the piggybac transposase is a transposase containing c-myc nuclear localization signal coding sequence. In certain embodiments, the coding sequence of piggybac transposase is shown in SEQ ID NO: 5 of CN201510638974.7.

The promoter of the transposase coding sequence may be various promoters known in the art for controlling the expression of the transposase coding sequence. In certain embodiments, the CMV promoter is used to control the expression of the transposase coding sequence. The sequence of the CMV promoter may be as shown in SEQ ID NO: 6 of CN 201510638974.7.

In certain embodiments, the vector herein containing the coding sequence of the chimeric antigen receptor is the pNB328 vector disclosed in CN201510638974.7. The coding sequence of the chimeric antigen receptor of the present disclosure can be prepared and cloned into a suitable vector by conventional methods in the art In certain embodiments, the vector used to integrate the gene of interest into the genome of the host cell does not contain a transposase coding sequence. For example, such vectors can be obtained by removing the transposase coding sequence from the pNB328 vector. Generally, such vectors can be used to integrate the expression cassette of the antibody of the present disclosure into the genome of the host cell.

The nucleic acid sequences described herein can be obtained by methods well known in the art, such as PCR amplification. For example, sequences of interest can be amplified by use of primers designed based on the nucleotide sequences disclosed herein, and commercially available cDNA libraries or cDNA libraries prepared according to conventional methods known to those skilled in the art as templates. When the sequence is long, two or more PCR amplifications may be necessary, and then the amplified fragments from amplifications are spliced together in the correct order.

It should be understood that it is often necessary to add appropriate restriction site(s) during the gene cloning process, which will inevitably introduce one or more irrelevant residues at the end(s) of the expressed amino acid sequence (s), while not affect the activity of the obtained sequence. In order to construct the fusion protein, promote the expression of the recombinant protein, obtain the recombinant proteins automatically secreted by the host cells, or facilitate the purification of the recombinant proteins, it is often necessary to add amino acid(s) to the N-terminus, C-terminus, or within other suitable regions of the recombinant protein, and the added amino acid(s) include but are not limited to suitable linker peptides, signal peptides, leader peptides, terminally extended amino acid(s), etc. Therefore, the N-terminus or C-terminus of the CAR herein may further contains one or more polypeptide fragments as protein labels. Any suitable label can be used for this disclosure. For example, the labels may be FLAG, HA, HA1, c-Myc, Poly-His, Poly-Arg, Strep-TagII, AU1, EE, T7, 4A6, c, B, gE, and Ty1. These labels can be used to purify proteins.

6. Host Cells and Preparation Thereof

The present disclosure also provides a host cell containing the nucleic acid construct described herein, or expressing the antibody and/or chimeric antigen receptor described herein.

The host cell of the present disclosure may be various cells well known in the art suitable for expressing antibodies, such as 293 or CHO cells. Such host cells may contain expression vectors that express the antibodies described herein.

In certain embodiments, the host cell of the present disclosure is a cell for simultaneously expressing the antibody and the chimeric antigen receptor described herein, which contains the coding sequence or expression cassette of the antibody and the chimeric antigen receptor described herein; preferably, two expression cassettes are integrated into the genome of the cell, i.e., the expression cassette of the antibody and the expression cassette of the chimeric antigen receptor, as described herein. Preferably, such cells are T cells. T cells of interest include but are not limited to peripheral blood T lymphocytes, cytotoxic T lymphocytes (CTL), helper T cells, inhibitory/regulatory T cells, γδ T cells, and cytokine-induced killer cells (CIK), tumor infiltration lymphocytes (TIL), or T cells of a mixed cell population.

Preferably, the T cell is transfected with a vector for integration of an expression cassette of the chimeric antigen receptor into its genome and containing a transposase coding sequence, and a vector for integration of an expression cassette of the antibody as described herein into its genome and not containing a transposase coding sequence. More preferably, the T cells are transfected with a vector containing an expression cassette of the chimeric antigen receptor constructed based on the pNB328 vector and a vector containing an expression cassette of the antibody described herein constructed based on the pS328 vector (comprising no transposase coding sequence compared to pNB328). In certain embodiments, the vector for integration of an expression cassette of the chimeric antigen receptor into the T cell genome and containing a transposase coding sequence comprises sequentially a 5'LTR, a promoter, the coding sequence of the CD8 signal peptide or a light chain signal peptide, the coding sequence of the antigen recognition region, the coding sequence of the CD8α hinge region or the IgG4 CH2CH3 hinge region, the coding sequence of the CD8 or CD28 transmembrane region, the coding sequence of the 4-1BB or CD28 intracellular domain, the coding sequence of the CD3 intracellular signal domain, a polyA tailing signal sequence, a 3'LTR and the coding sequence of a transposase and its promoter; the vector for integration of an expression cassette of the antibody as described herein into the T cell genome and not containing a transposase coding sequence comprises sequentially between the 5'LTR and the 3'LTR a promoter, the coding sequence of the light chain signal peptide or the CD8 signal peptide, the coding sequence of the antibody, and a polyA tailing signal sequence. Preferably, the antigen recognition region is an antigen recognition region targeting CD19, mesothelin, mucin, EGFR or ErbB family, preferably their amino acids and coding sequences are as described above. Preferably, the antibody is an anti-PD-1 antibody, an anti-CD47 antibody or an anti-CD40 antibody; preferably, their amino acid sequences and coding sequences are as described above.

Conventional transfection methods can be used to transfer the vectors of the present disclosure into cells of interest, including but not limited to: viral transduction, microinjection, particle bombardment, gene gun transformation, and electroporation. In certain embodiments, the vectors described herein are transfected into cells of interest by electroporation. Preferably, during transfection, the mass ratio of the vector containing the coding sequence of the chimeric antigen receptor to the vector containing the coding sequence of the antibody is 1-7:1-7, such as 1-5:1-5, preferably 1-3:1-3, more preferably 1-2:1-2, more preferably 1-2:1.

7. Compositions and Kits

The disclosure also provides a composition comprising the vector described herein, preferably the vector expressing the chimeric antigen receptor described herein and the vector expressing the antibody described herein. The composition is used at least to provide a vector for transfection.

In the composition of the present disclosure, the mass ratio of the vector expressing the chimeric antigen receptor described herein to the vector expressing the antibody described herein may be 1-7:1-7, such as 1-5:1-5, preferably 1-3:1-3, more preferably 1-2:1-2, more preferably 1-2:1. The composition may also contain suitable reagents, including but not limited to reagents for transfection.

The present disclosure also provides a kit containing a vector expressing the chimeric antigen receptor described herein and a vector expressing the antibody described herein, or a composition described herein. The kit may also be equipped with reagents and/or instruments for transferring the vector into cells.

The composition herein may be a pharmaceutical composition containing the T cells described herein or the T cells and the antibodies described herein expressed by the T cells. The pharmaceutical composition may contain a suitable pharmaceutically acceptable carrier or adjuvant. Suitable carriers or adjuvants include but are not limited to buffers and osmotic pressure regulators and the like. The pharmaceutical composition contains a therapeutically or prophylactically effective amount of T cells. The therapeutically or prophylactically effective amount of T cells can be determined according to factors such as the patient's condition.

8. Method and Use

The disclosure also provides the use of the antibodies, their coding sequences or complementary sequences thereof, nucleic acid constructs, and host cells, as described herein, in the preparation of a medicament for treatment or prevention of malignant tumors. The tumor includes, but is not limited to, tumors associated with the antigen to which the antibody specifically binds to. The disclosure also includes the antibodies, their coding sequences or complementary sequences thereof, nucleic acid constructs, and host cells, as described herein, for treatment or prevention of malignant tumors.

The present disclosure also provides the use of the T cells described herein or the T cells and the antibodies expressed by the cells or pharmaceutical compositions thereof in the preparation of a medicament for treatment or prevention of malignant tumors. The present disclosure also includes the T cells described herein or the T cells and the antibodies expressed by the cells or pharmaceutical compositions thereof for treatment or prevention of malignant tumors.

The present disclosure also provides a method for treating or preventing malignant tumors, the method comprising administering to a subject in need thereof a therapeutically or prophylactically effective amount of the T cells or pharmaceutical composition thereof described herein.

The malignant tumor (cancer) that can be treated or prevented by the T cell of the present disclosure or the T cell and the antibody expressed by the T cell or a pharmaceutical composition thereof or the method described by the present disclosure may be the malignant tumor that can be treated or prevented by the antibody and/or chimeric antigen receptor expressed by the T cell. For example, when the chimeric antigen receptor is a chimeric antigen receptor targeting CD19, the malignant tumor may be malignant B-cell lymphoma, including acute B-lymphocytic leukemia (B-ALL), chronic B-lymphocytic leukemia (B-CLL), mantle cell lymphoma (MCL), non-Hodgkin lymphoma (NHL) and multiple myeloma (MM). When the chimeric antigen receptor targets mesothelin, the malignant tumor may be a cancer that abnormally expresses mesothelin on the surface of the cancer cell; preferably is adenocarcinoma, mesothelioma, lung cancer, colon cancer, colorectal cancer, breast cancer, ovarian cancer, cervical cancer, gastric cancer, bile duct cancer, gallbladder cancer, esophageal cancer, melanoma, non-small cell lung cancer, renal cell cancer, head and neck squamous cell carcinoma, rectal cancer, Hodgkin lymphoma, pancreatic cancer or prostate cancer; more preferably, the cancer is a cancer in which mesothelin and CA125/MUC16 are simultaneously highly expressed. When the chimeric antigen receptor targets the ErbB family, the malignant tumor may be a cancer that abnormally expresses at least one protein of EGFR family on the surface of the cancer cells, such as liver cancer, adenocarcinoma, lung cancer, colon cancer, colorectal cancer, breast cancer, ovarian cancer, cervical cancer, gastric cancer, bile duct cancer, non-small cell cancer, gallbladder cancer, esophageal cancer, melanoma, pancreatic cancer, urothelial cancer, head and neck cancer or prostate cancer. When the chimeric antigen receptor targets mucin, the malignant tumor may be a cancer that abnormally expresses mucin antigen on the surface of the cancer cells, such as liver cancer, adenocarcinoma, lung cancer, colon cancer, colorectal cancer, breast cancer, ovarian cancer, cervical cancer, gastric cancer, bile duct cancer, non-small cell cancer, gallbladder cancer, esophageal cancer, melanoma, pancreatic cancer, urothelial cancer, head and neck cancer or prostate cancer. When the chimeric antigen receptor targets EGFR, the malignant tumor may be a cancer that abnormally expresses EGFR on the surface of the cancer cells, such as glioblastoma, renal cancer, adenocarcinoma, lung cancer, colon cancer, colorectal cancer, breast cancer, ovarian cancer, cervical cancer, gastric cancer, bile duct cancer, gallbladder cancer, esophageal cancer, pancreatic cancer or prostate cancer. When the antibody is a CD40 antibody, a suitable malignant tumor is a malignant tumor mediated by CD40, including but not limited to non-small cell carcinoma, melanoma, urothelial carcinoma, high frequency microsatellite instability (MSI-H) and head and neck cancer; when the antibody is a PD-1 antibody, a suitable malignant tumor is a malignant tumor mediated by PD-1, including but not limited to melanoma, colon cancer, prostate cancer, non-small cell lung cancer and renal cell carcinoma and other solid tumors. When the antibody is a CD47 antibody, a suitable malignant tumor includes but is not limited to any tumor that expresses CD47 on the surface of the cancer cells.

The embodiments of the present disclosure will be illustrated by way of specific examples below. Those skilled in the art will understand that these examples are merely exemplary and should not be considered as limiting the scope of the present disclosure. The experimental methods without specifying the specific technology or conditions in the following examples generally used the conventional technology or conditions, such as those described in J. Sambrook et al., Molecular Cloning: A Laboratory Manual (3rd ed.), translated by Huang Peitang et al., *Science Press*, or followed the manufacturer's recommendation.

The used reagents or instruments without specifying the manufacturer are all conventional products that are commercially available.

Example 1: Construction of Recombinant Plasmid

Foreign genes (antibody or CAR) shown in Table 1 below were synthesized by Shanghai Generay Biotech Co., Ltd, with multiple-cloning restriction sites (BglII-XbaI-EcoRI-BamHI) introduced upstream and restriction sites (SalI-NheI-HindIII-SpeI) introduced downstream of the genes. The genes were inserted into pNB328 vectors or pS328 vectors (for the structure and sequence of pNB328, please refer to CN201510638974.7, the entire contents of which are incorporated herein by reference; compared to pNB328, p5328 lacks the coding sequence of the transposase; the chimeric antigen receptor genes were inserted into pNB328 vectors, and the antibody sequences were loaded into pS328 vectors) that were double digested by EcoR1+SalI to construct the recombinant plasmids.

TABLE 1

| Foreign Gene Name | Foreign Gene Structure | Sequence No. | Recombinant Plasmid Name |
|---|---|---|---|
| mutant CD40 antibody | light chain signal peptide-CD40 scFv-mutant IgG4Fc | 2 | pS328-αCD40 |
| mutant PD-1 antibody | light chain signal peptide-PD-1 scFv-mutant IgG4Fc | 4 | pS328-m279v or pS328-antiPD1 |
| mutant CD47 antibody | light chain signal peptide-CD47 ligand-IgG4Fc | 6 | pS328-αCD47 |
| CD19CAR | CD8 signal peptide-anti-CD19 scFv-CD8α hinge region-CD8 transmembrane region-4-1BB intracellular domain-CD3ζ | 8 | pNB328-CD19CAR |
| mesoCAR | CD8 signal peptide-anti-meso scFv-mIgG4 Fc CH2CH3 hinge region-CD8 transmembrane region-CD28 intracellular domain-CD3ζ | 10 | pNB328-mesoCAR |
| Meso3CAR | light chain signal peptide-anti-meso scFv-mIgG4 Fc CH2CH3 hinge region-CD8 transmembrane region-CD28 intracellular domain-CD3ζ | 12 | pNB328-meso3CAR |
| ErbBCAR | CD8 signal peptide-T1E-EK linker-Herin-mIgG4 Fc CH2CH3 hinge region-CD28 transmembrane region-CD28 intracellular domain-CD3ζ | 14 | pNB328-EHCAR-EK-28TIZ |
| Muc1CAR | CD8 signal peptide-anti-Muc1 scFv-mIgG4 Fc CH2CH3 hinge region-CD28 transmembrane region-CD28 intracellular domain-CD3ζ | 16 | pNB328-Muc1CAR |
| EGFR-CAR | CD8 signal peptide-anti-EGFR scFv-mIgG4 Fc CH2CH3 hinge region-CD28 transmembrane region-CD28 intracellular domain-CD3ζ | 18 | pNB328-EGFR-CAR |
| CD19CAR-2A-αCD40 | CD19CAR-2A-mutant CD40 antibody | 19* | pNB328-CD19CAR-2A-αCD40 |
| αCD40-IRES-CD19CAR | mutant CD40 antibody-IRES-CD19CAR | 20* | pNB328-αCD40-IRES-CD19CAR |
| mesoCAR-2A-αCD40 | mesoCAR-2A-mutant CD40 antibody | 19* | pNB328-mesoCAR-2A-αCD40 |
| αCD40-IRES-mesoCAR | mutant CD40 antibody-IRES-mesoCAR | 20* | pNB328-αCD40-IRES-mesoCAR |
| CD19CAR-2A-m279v | CD19CAR-2A-mutant PD-1 antibody | 19* | pNB328-CD19CAR-2A-m279V |
| m279v-IRES-CD19CAR | mutant PD-1 antibody-IRES-CD19CAR | 20* | pNB328-m279V-IRES-CD19CAR |
| mesoCAR-2A-antiPD1 | mesoCAR-2A-mutant PD-1 antibody | 19* | pNB328-mesoCAR-2A-antiPD1 |
| antiPD1-IRES-mesoCAR | mutant PD-1 antibody-IRES-mesoCAR | 20* | pNB328-antiPD1-IRES-mesoCAR |
| WT CD40 antibody | light chain signal peptide-CD40 scFv-WT IgG4Fc | ** | pS328-αCD40-wt |
| WTPD-1 antibody | light chain signal peptide-PD-1 scFv-WT IgG4Fc | | pS328-m279v-wt |
| WT CD47 antibody | light chain signal peptide-CD47 ligand-WT IgG4Fc | | pS328-αCD47-wt |

*SEQ ID NO: 19 shows the nucleotide sequence of 2A, SEQ ID NO: 20 shows the nucleotide sequence of IRES; the sequence of the rest of the foreign gene sequence is identical with the sequence of the foreign gene having the same name in the Table;
**the sequence of WT IgG4Fc is shown as SEQ ID NO: 25, which is identical with that of the mutant IgG4Fc except for L17E (CTG to GAG) and N79Q (AAC to CAG) mutations in the mutant.

Example 2: Construction of CAR-T Cells

Peripheral blood mononuclear cells (PBMCs) were isolated from patients' blood by Filcoll separation method. PBMCs were adherently cultured for 2-4 h, and the non-adherent suspended cells were the initial T cells, which were collected in a 15 ml centrifuge tube and centrifuged at 1200 rmp for 3 min, then the supernatant was discarded and saline was added. This step was repeated.

$5 \times 10^6$ cells were added in a 1.5 ml centrifuge tube, and centrifuged at 1200 rmp for 3 min. The supernatant was discarded, a total of 100 ul of the electroporation reagent of the Electroporation Kit (Lonza) was added, and then different recombinant plasmids were added according to Table 2 below. The cells were resuspended and mixed separately; the mixture was transferred to an electroporation cup, the cup was put into the electroporation instrument, the required program was selected, and electrical pulse was conducted; the micro pipette in the kit was used to transfer the electroporated cell suspension to a six-well plate supplemented with the medium (AIM-V medium containing 2% FBS), the cells were mixed well and cultured in a 37° C., 5% $CO_2$ incubator; after six hours, stimulating factor IL-2, anti-CD28 antibody and corresponding antigen (CD19, mesothelin, EGFR or mucin) or anti-CD3 antibody was added, and the cells were culture at 37° C., 5% $CO_2$ for 3 to 4 days to obtain corresponding T cells.

When two kinds of recombinant plasmids were transferred, 4 ug of each recombinant plasmid was used; when one kind of recombinant plasmid was transferred, 6 ug is used.

TABLE 2

| Recombinant Plasmid | Name of Recombinant Cell |
| --- | --- |
| pNB328 empty vector | Mock T cells or NT T cells |
| pNB328-CD19CAR + pS328-αCD40 | CD19CAR-αCD40 T cells |
| pNB328-CD19CAR-2A-αCD40 | CD19CAR-2A-αCD40 T cells |
| pNB328-αCD40-IRES-CD19CAR | αCD40-IRES-CD19CAR T cells |
| pNB328-CD19CAR | CD19CAR T cells |
| pNB328-CD19CAR + pS328-αCD40-wt | CD19CAR-αCD40-wt T cells |
| pNB328-mesoCAR + pS328-αCD40 | mesoCAR-αCD40 T cells |
| pNB328-mesoCAR-2A-αCD40 | mesoCAR-2A-αCD40 T cells |
| pNB328-αCD40-IRES-mesoCAR | αCD40-IRES-mesoCAR T cells |
| pNB328-mesoCAR | mesoCAR T cells |
| pNB328-mesoCAR + pS328-αCD40-wt | mesoCAR-αCD40-wt T cells |
| pNB328-EHCAR-EK-28TIZ + pS328-αCD40 | EHCAR-EK-28TIZ-αCD40 T cells |
| pNB328-EHCAR-EK-28TIZ | EHCAR-EK-28TIZ T cells |
| pNB328-Muc1CAR + pS328-αCD40 | Muc1CAR-αCD40 T cells |
| pNB328-Muc1CAR | Muc1CAR T cells |
| pS328-CD19CAR + pNB328-m279V | pS328-CD19CAR + pNB328-m279V T cells |
| pNB328-CD19CAR + pS328-m279V | CD19CAR-antiPD1 T cells |
| pNB328-CD19CAR-2A-m279V | pNB328-CD19CAR-2A-m279v T cells |
| pNB328-m279V-IRES-CD19CAR | pNB328-m279V-IRES-CD19CAR T cells |
| pNB328-CD19CAR + pS328-m279V-wt | CD19CAR-antiPD1-wt T cells |
| pNB328-mesoCAR + pS328-antiPD1 | mesoCAR-antiPD1 T cells |
| pNB328-mesoCAR-2A-antiPD1 | mesoCAR-2A-antiPD1 T cells |
| pNB328-antiPD1-IRES-mesoCAR | antiPD1-IRES-mesoCAR T cells |
| pNB328-meso3CAR | meso3CAR T cells |
| pNB328-EHCAR-EK-28TIZ + pS328-antiPD1 | EHCAR-EK-28TIZ-antiPD1 T cells |
| pS328-Muc1CAR + pNB328-m279V | pS328-Muc1CAR + pNB328-antiPD1 T cells |
| pNB328-Muc1CAR + pS328-m279V | Muc1CAR-antiPD1 T cells |
| pNB328-Muc1CAR-2A-m279V | Muc1CAR-2A-antiPD1 T cells |
| pNB328-m279V-IRES-Muc1CAR | antiPD1-IRES-Muc1CAR T cells |
| pNB328-Muc1CAR + pS328-m279V-wt | pNB328-Muc1CAR + pS328-antiPD1-wt T cells |
| pNB328-EGFR-CAR + pS328-αCD47 | αCD47-EGFR-CAR T cells |
| pNB328-EGFR-CAR | EGFR-CAR T cells |
| pNB328-EGFR-CAR + pS328-wt-αCD47 | wt-αCD47-EGFR-CAR T cells |
| pNB328-meso3CAR + pS328-αCD47 | αCD47-Meso3CAR T cells |
| pNB328-meso3CAR + pS328-αCD47-wt | wt-αCD47-Meso3CAR T cells | assayed on the machine, with a control only being added with the secondary antibody. The results are shown in Table 3.

TABLE 3

| T cell type | Positive Rate (%) |
| --- | --- |
| C19CAR-αCD40 T cells | 80.52 |
| CD19CAR-2A-αCD40 T cells | 1.21 |
| αCD40-IRES-CD19CAR T cells | 48.68 |
| mesoCAR-αCD40 T cells | 88.48 |
| mesoCAR-2A-αCD40 T cells | 23.02 |
| αCD40-IRES-mesoCAR T cells | 53.84 |
| EHCAR-EK-28TIZ-αCD40 T cells | 56.02 |
| EHCAR-EK-28TIZ T cells | 53.53 |

Example 3: Positive Rate and Antibody Secretion of CAR-T Cells

1. Detection of Positive Rate of CAR T Cells by Flow Cytometry

CAR-T cells prepared in Example 2 were collected and divided into two groups each with $1 \times 10^6$ cells, washed twice with normal saline, and resuspended with 100 ul normal saline. One group was added with 1 ug of biotin-conjugated antigen (CD19, mesothelin, EGFR or mucin), the other was not. The two groups were incubated at 4° C. for 30 minutes. The cells were washed twice with normal saline, resuspended with 100 ul of normal saline again, added with 1 ul of streptomycin-PE antibody, and incubated at 4° C. for 30 minutes. The cells was washed twice with normal saline and TABLE 3-continued

| T cell type | Positive Rate (%) |
| --- | --- |
| Muc1CAR T cells | 65.52 |
| Muc1CAR-αCD40 T cells | 71.48 |
| CD19CAR T cells | 50.24 |
| CD19CAR-antiPD1 T cells | 58.64 |
| mesoCAR-antiPD1 T cells | 86.42 |
| mesoCAR-2A-antiPD1 T cells | 68.01 |
| antiPD1-IRES-mesoCAR T cells | 46.97 |
| EHCAR-EK-28TIZ-antiPD1 T cells | 61.36 |
| pS328-Muc1CAR + pNB328-antiPD1 T cells | 45.63 |
| Muc1CAR-antiPD1 T cells | 91.17 |
| Muc1CAR-2A-antiPD1 T cells | 10.38 |
| antiPD1-IRES-Muc1CAR T cells | 35.33 |
| αCD47-EGFR-CAR T cells | 67.17 |
| αCD47-Meso3CAR T cells | 70.57 |

2. Detection of Expression Level of the Antibody by CAR-T Cells Prepared in Example 2 Using ELISA ① Dilute the corresponding antigen (CD40, PD1 or CD47) to 0.5 ug/ml with the coating solution (5 ul+1 ml coating solution), coat the ELISA plate with 100 ul/well overnight at 4° C.
② Wash 5 times with PBST, 3 minutes each time, dry the plate with absorbent paper by patting, 200 ul/well.
③ Add 100 ul of blocking solution to each well, and incubate at 37° C. for 1 hour.
④ Wash 5 times with PBST, 3 minutes each time, dry the plate with absorbent paper by patting, 200 ul/well.
⑤ Add samples and standards, 100 ul/well, including replicates and control, and incubate at 37° C. for 1 hour.
⑥ Wash 5 times with PBST, 3 minutes each time, dry the plate with absorbent paper by patting, 200 ul/well.
⑦ Dilute IgG F4 HRP with blocking solution at 1:30,000, 100 ul/well, and incubate at 37° C. for 45 minutes.
⑧ Wash 5 times with PBST, 3 minutes each time, dry the plate with absorbent paper by patting, 200 ul/well.
⑨ Add chromogenic solution TMB, 100 ul/well, incubate in dark at 37° C. for 10-15 min.
⑩ Add terminal solution to stop the reaction, 50 ul/well.

The OD values at 450 nm were measured by microplate reader, standard curves were generated, and concentrations of the CD40 antibody were calculated.

The results are shown in Table 4.

TABLE 4

| Type of T cell | Type of Antibody | Secreted Amount (ng/ml) |
| --- | --- | --- |
| CD19CAR-αCD40 T cell | mutant CD40 antibody | 1437.1315 |
| CD19CAR-2A-αCD40 T cell | mutant CD40 antibody | 719.9956 |
| αCD40-IRES-CD19CAR T cell | mutant CD40 antibody | 543.3876 |
| mesoCAR-αCD40 T cell | mutant CD40 antibody | 1341.136 |
| mesoCAR-2A-αCD40 T cell | mutant CD40 antibody | 652.5344 |
| αCD40-IRES-mesoCAR T cell | mutant CD40 antibody | 525.2928 |
| EHCAR-EK-28TIZ-αCD40 T cell | mutant CD40 antibody | 238 |
| EHCAR-EK-28TIZ T cell | mutant CD40 antibody | 0.64 |
| Muc1CAR T cell | mutant CD40 antibody | 0.13 |
| Muc1CAR-αCD40 T cell | mutant CD40 antibody | 152 |
| pS328-CD19CAR + pNB328-m279v T cell | mutant PD-1 antibody | 840.9641 |
| CD19CAR-antiPD1 T cell | mutant PD-1 antibody | 1230.3335 |
| pNB328-CD19CAR-2A-m279v T cell | mutant PD-1 antibody | 100.00167 |
| pNB328-m279V-IRES-CD19CAR T cell | mutant PD-1 antibody | 410.75748 |
| mesoCAR-antiPD1 T cell | mutant PD-1 antibody | 1220.63764 |
| mesoCAR-2A-antiPD1 T cell | mutant PD-1 antibody | 675.58424 |
| antiPD1-IRES-mesoCAR T cell | mutant PD-1 antibody | 783.21583 |
| EHCAR-EK-28TIZ-antiPD1 T cell | mutant PD-1 antibody | 268 |
| pS328-Muc1CAR + pNB328-antiPD1 T cell | mutant PD-1 antibody | 45.93 |
| Muc1CAR-antiPD1 T cell | mutant PD-1 antibody | 91.17 |
| Muc1CAR-2A-antiPD1 T cell | mutant PD-1 antibody | 10.38 |
| antiPD1-IRES-Muc1CAR T cell | mutant PD-1 antibody | 35.33 |
| αCD47-EGFR-CAR T cell | mutant CD47 antibody | 1112.325 |
| αCD47-Meso3CAR T cell | mutant CD47 antibody | 986.549 |

Example 4: Tests of Different Plasmid Ratios

CAR-T cells were prepared according to the method of Example 2, using the plasmid combinations constructed in Example 1 and mass ratios according to Table 5 (1 ug+7 ug, 2 ug+6 ug, 3 ug+5 ug, 4 ug+4 ug, 5 ug+3 ug, 6 ug+2 ug, 7 ug+1 ug). The method described in Example 3 was used to detect the positive rates and the antibody secretions of CAR T cells based on the different mass ratios (the method is the same as Example 3).

TABLE 5

| | |
| --- | --- |
| pNB328-CD19CAR | pS328-αCD40 |
| pNB328-mesoCAR | pS328-αCD40 |
| pNB328-EHCAR-EK-28TIZ | pS328-αCD40 |
| pNB328-Muc1CAR | pS328-αCD40 |
| pNB328-CD19CAR | pS328-m279V |
| pNB328-mesoCAR | pS328-antiPD1 |
| pNB328-EHCAR-EK-28TIZ | pS328-antiPD1 |
| pNB328-Muc1CAR | pS328-m279V |
| pNB328-EGFR-CAR | pS328-αCD47 |
| pNB328-meso3CAR | pS328-αCD47 |

Exemplary results are shown in Tables 6 and 7 below.

TABLE 6

| Different mass ratios (pNB328-CD19CAR:pS328-m279V) | Expression of PD1 antibody (ng/ml) | Positive rate of CAR-T cells (%) |
| --- | --- | --- |
| 4:4 | 1320.93 | 80.89 |
| 3:5 | 1130.73 | 72.07 |
| 2:6 | 1030.02 | 57.72 |
| 1:7 | 420.93 | 13.01 |

TABLE 7

| Different mass ratios (pNB328-Muc1CAR:pS328-m279V) | Expression of PD1 antibody (ng/ml) | Positive rate of CAR-T cells (%) |
| --- | --- | --- |
| 1:1 | 2200.01 | 92.55 |
| 3:5 | 1860.00 | 79.54 |
| 1:3 | 1260.77 | 54.63 |
| 1:7 | 310.88 | 20.82 |

The results show that, based on the positive rate and antibody secretion results, EHCAR-EK-28TIZ-αCD40 T cells prepared by 5 ug pNB328-EHCAR-EK-28TIZ and 3 ug pS328-αCD40 have the best effect (positive rate greater than 60%, antibody secretion greater than 230 ng/ml); in other plasmid combinations, 4 ug+4 ug has better effect than other mass ratios.

Example 5: Comparison of Cytokine Release Between CD19CAR and CD19CAR-αCD40 T Cells Under Specific Stimulation of CD19 Antigen 96-well plates were coated overnight with 2 ug/ml CD19 antigen at 4° C., washed 3 times with PBS, added with $1\times10^5$ CD19CAR and CD19CAR-αCD40 T cells prepared according to Example 2 and control Mock T cells. Supernatants were collected after 24 hours of culture. BD's CBA Human Th1/Th2 Cytokine Kit II was used to detect the cytokine secretion of these three T cells upon stimulation by CD19 antigen. The particular steps are as follows:

(1) Mix human IL-2, IL-4, IL-6, IL-10, TNF-α, IFN-γ capture magnetic beads by vortex, add 50 ul of mixed beads to each tube;
(2) Add 50 ul of human Th1/Th2 cytokine standard (diluted to 5000 pg/ml, 2500 pg/ml, 1250 pg/ml, 625 pg/ml, 312.5 pg/ml, 156 pg/ml, 80 pg/ml, 40 pg/ml, 20 pg/ml, or 0 pg/ml) and 50 ul of the sample to be tested (diluted by 2-fold with the diluents);
(3) Add 50 ul of human Th1/Th2-II-PE detection antibody to each tube;
(4) Incubate at room temperature in the dark for 3 h;
(5) Add 1 ml of washing buffer to each tube, centrifuge at 200 for 5 min, and discard the supernatant;
(6) Add 300 ul of washing buffer to each tube to resuspend the cells, and transfer the cells to a flow cytometry tube to detect the fluorescence value by a flow cytometer.

The results are shown in FIG. 1.

Example 6: Proliferation Detection of CD19CAR and CD19CAR-αCD40 T Cell $3\times10^5$ cells of Mock T cells and the CD19CAR T cells and CD19CAR-αCD40 T cells that have been cultured for 8 days according to Example 2 were cultured in 12-well plates with the culture volume of 1 ml.

2. 100 μL of cell-containing culture medium from each group was added to different wells of a 96-well white opaque plate, with culture medium without cells as a blank control. Each well was added with 100 μL CellTiter-Glo reagent, mixed on a shaker for 2 min, and incubated at room temperature for 10 min, and then detected by a microplate reader for fluorescence value of Luc. The used CellTiter-Glo Luminescent Cell Viability Assay kit was purchased from Promega.

3. The same detections for the cells from 12-well plates were made according to the above steps on the 9th, 10th, 11th, 12th, and 13th days of culture. Cell proliferation curves were drawn based on the detected fluorescence values.

Figure 2:
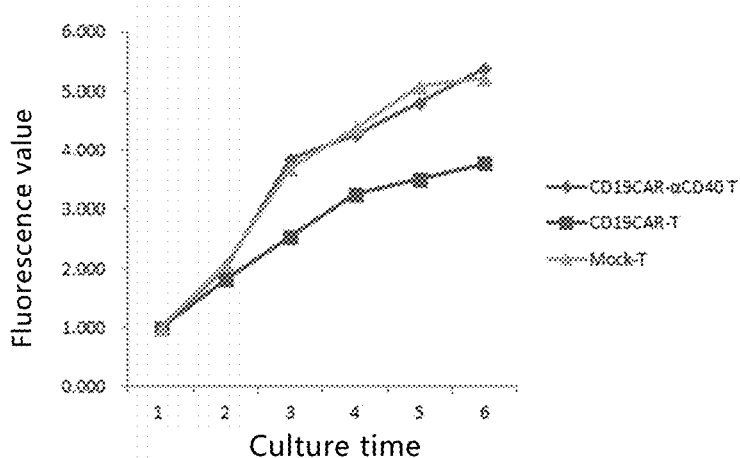
FIG. 2: Proliferation detection of CD19CAR T cells and CD19CAR-αCD40 T cells.

The results show that CD19CAR-αCD40 T cells have a better proliferation than CD19CAR T cells. The results are shown in FIG. 2.

Example 7: Functional Assay of CD19CAR T Cells and CD19CAR-αCD40 T Cells In Vivo Twelve of 4-6 weeks old NSG completely immunodeficient mice, with an average weight of 22-27 g, were provided by Beijing Biocytogen Biotech Co., Ltd., and raised by a SPF animal laboratory.

Human B-cell lymphoma Raji-luc cells in logarithmic growth phase cultured in vitro were centrifuged, collected and resuspended in PBS solution. The cells were centrifuged at 3000 g for 2 minutes at room temperature, the supernatant was discarded and the cells were resuspended in PBS solution, centrifuged and collected, and the concentration of the cell suspension was adjusted to $5\times10^7$ cells/ml. The Raji-luc cells were inoculated subcutaneously in the dorsum of the right rib of the mouse at 0.1 ml/mouse. About 10 days after the inoculation, the size of the tumor was observed by an in vivo imager, and the NSG immunodeficient mice were randomly divided into 5 groups: PBS group, Mock T group, CD19CAR T group, CD19CAR-αCD40-wt T, and CD19CAR-αCD40T group. Each group was injected through the tail vein with corresponding T cells (from Example 2) at $1\times10^7$ cells/100 ul, and PBS group was injected with 100 ul of PBS. The living conditions of mice were observed every day and the change of the tumor in each mouse was observed by in vivo imager every 7-8 days.

Figure 3:
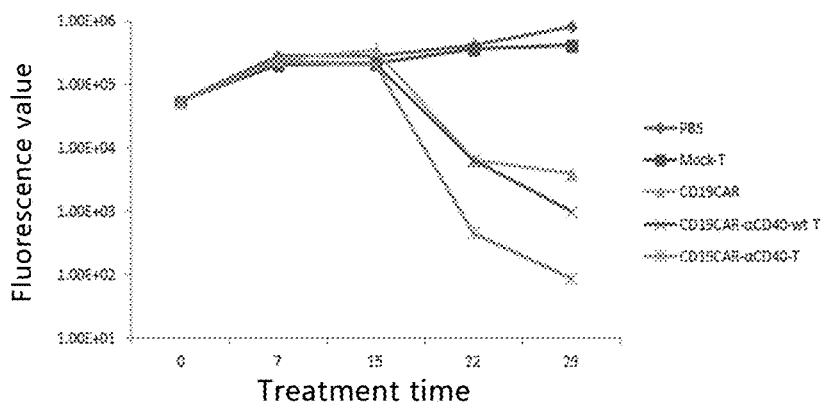
FIG. 3: The therapeutic effects of CD19CAR T cells, CD19CAR-αCD40-wt T, and CD19CAR-αCD40 T cells on the Raji-luc mouse xenograft model.

The results are shown in FIG. 3.

Example 8: Comparison of the Killing Effect by MesoCAR T and MesoCAR-αCD40 T Cells Real-time label-free cell analysis system was used to detect the killing effect of mesoCAR T cells and mesoCAR-αCD40 T cells prepared in Example 2 on tumor cells in vitro.

Figure 4:
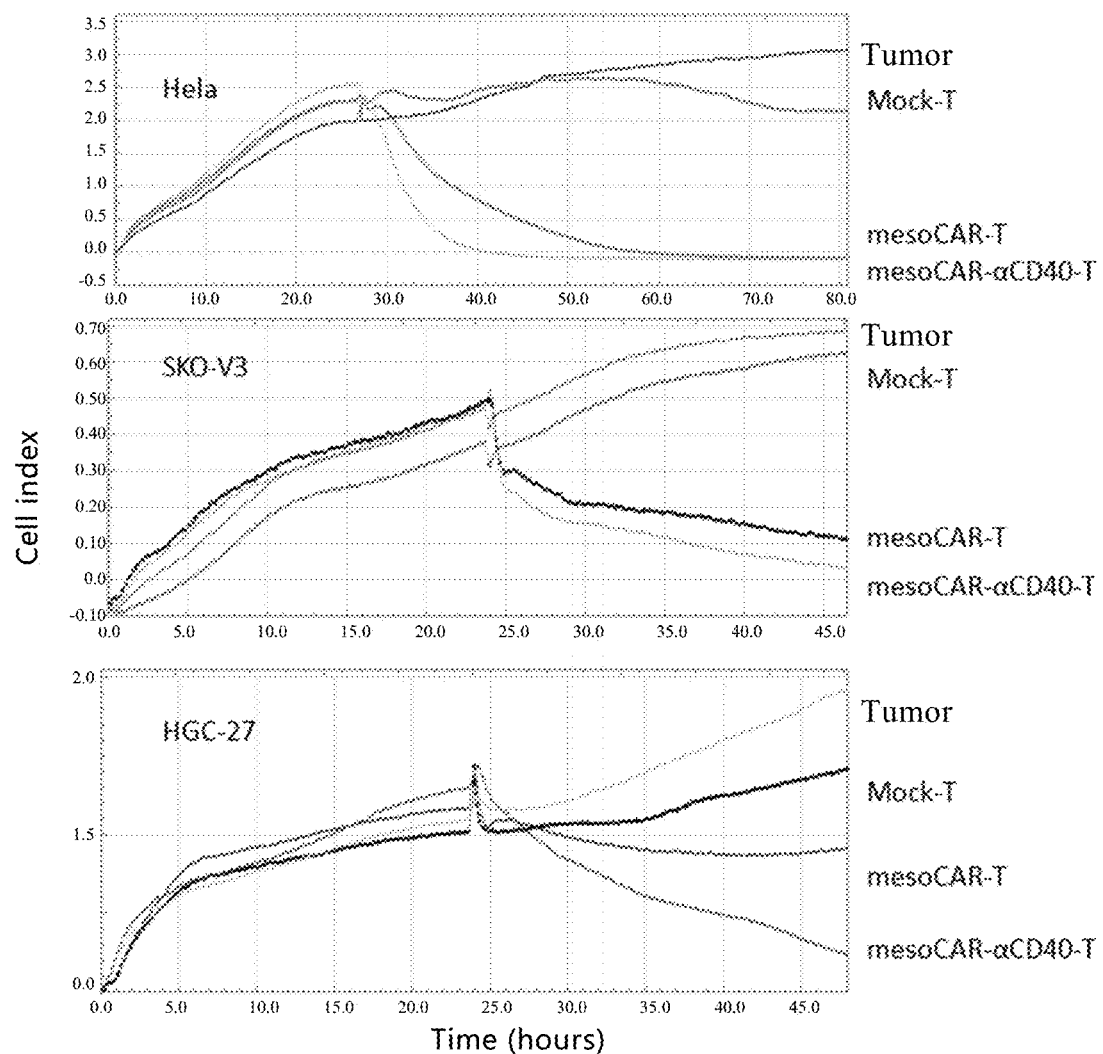
FIG. 4: The killing of mesoCAR-αCD40 T cells on cervical cancer cells Hela, ovarian cancer cells SK-OV-3 and gastric cancer cells HGC-27.

Specifically, target cells and effector cells that match MHC class I were selected, and Real-time label-free cell analysis system (RTCA, ACEA) was used to detect the killing effect of the above two CAR-T cells in vitro. The steps are as follows:

(1) Zero adjustment: Add 50 μl DMEM or 1640 culture medium to each well, put it into the instrument, select step 1, and adjust zero;
(2) Target cell plating: Plate cervical cancer cell Hela, ovarian cancer cell SK-OV-3, gastric cancer cell HGC-27 (American Type Culture Collection ATCC) at $10^4$ cells/50 μl per well on a plate containing detection electrodes, let rest for a few minutes to stabilize the cells, then put them into the instrument, start step 2 to culture the cells;
(3) Adding effector cells: After 24 h culture of target cells, pause step 2 and add effector cells at 50 μl per well, with the effect target ratio of 4:1 and Mock T cells as the control, start step 3 to continue co-cultivation for 24 h, then generate the cell proliferation curve;

The results are shown in FIG. 4. The killing effect of the mesoCAR-αCD40 T cells that self-express CD40 antibodies are substantially the same with that of the mesoCAR T cells alone. The expression of antibody does not affect the CAR-T function.

Example 9: Comparison of Cytokine Release Between MesoCAR and MesoCAR-αCD40 T Cells Under Specific Stimulation of Mesothelin Antigen 96-well plates were coated overnight with 2 ug/ml mesothelin antigen at 4° C., washed 3 times with PBS, added with $1\times10^5$ meso3CAR T cells and mesoCAR-αCD40 T cells prepared according to Example 2 and control Mock T cells. Supernatants were collected after 24 hours of culture. BD's CBA Human Th1/Th2 Cytokine Kit II was used to detect the cytokine secretion of these three T cells upon stimulation by mesothelin antigen. The particular steps are as follows:

(1) Mix human IL-2, IL-4, IL-6, IL-10, TNF, IFN-γ capture magnetic beads by vortex, add 50 ul of mixed beads to each tube;
(2) Add 50 ul of human Th1/Th2 cytokine standard (diluted to 5000 pg/ml, 2500 pg/ml, 1250 pg/ml, 625 pg/ml, 312.5 pg/ml, 156 pg/ml, 80 pg/ml, 40 pg/ml, 20 pg/ml, or 0 pg/ml) and 50 ul of the sample to be tested (diluted by 2-fold with the diluents);
(3) Add 50 ul of human Th1/Th2-II-PE detection antibody to each tube;
(4) Incubate at room temperature in the dark for 3 h;
(5) Add 1 ml of washing buffer to each tube, centrifuge at 200 for 5 min, and discard the supernatant;
(6) Add 300 ul of washing buffer to each tube to resuspend the cells, and transfer the cells to a flow cytometry tube to detect the fluorescence value by a flow cytometer.

Figure 5:
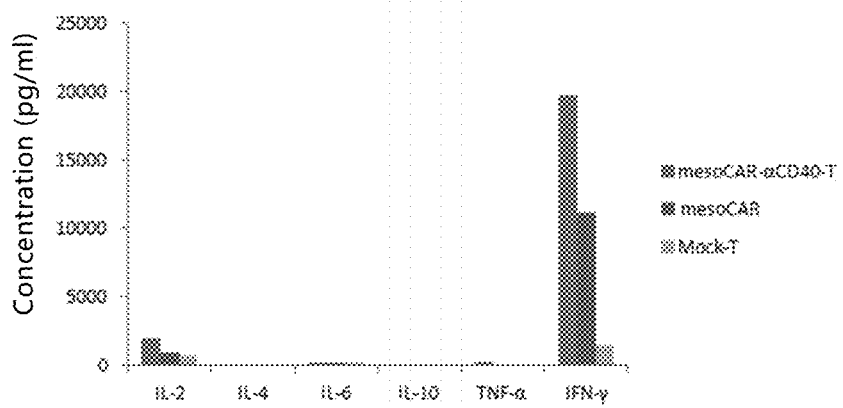
FIG. 5: Changes of secretions of cytokines IL-2, IL-4, IL-6, IL-10, TNF-α and IFN-γ of mesoCAR-αCD40 upon the stimulation of CD19 antigen.

The results are shown in FIG. 5. There is no significant difference in the amount of cytokine secretion between mesoCAR-αCD40 T cells that self-express CD40 antibody and mesoCAR T cells alone.

Example 10: Proliferation Detection of MesoCAR and MesoCAR-αCD40 T Cell $3 \times 10^5$ cells of Mock-T cells and the mesoCAR T cells and mesoCAR-αCD40 T cells that have been cultured for 8 days according to Example 2 were cultured in 12-well plates in a culture volume of 1 ml.

2. 100 μL of cell-containing culture medium from each group was added to different wells of a 96-well white opaque plate, with culture medium without cells as a blank control. Each well was added with 100 μL CellTiter-Glo reagent, mixed on a shaker for 2 min, and incubated at room temperature for 10 min, and then detected by a microplate reader for fluorescence value of Luc. The used CellTiter-Glo Luminescent Cell Viability Assay kit was purchased from Promega.

3. The same detections for the cells from 12-well plates were made according to the above steps on the 9th, 10th, 11th, 12th, and 13th days of culture. Cell proliferation curves were drawn based on the detected fluorescence values.

Figure 6:
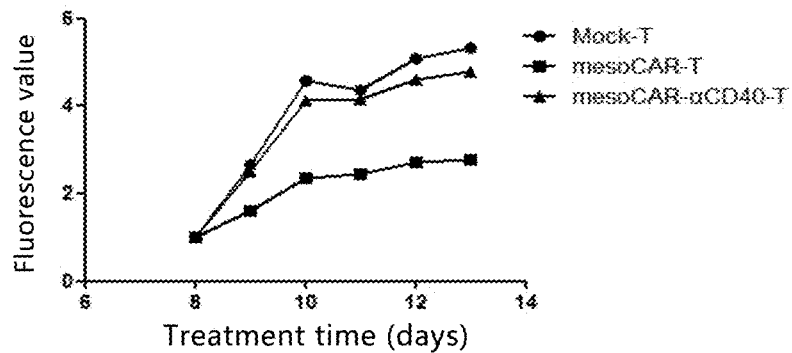
FIG. 6: Proliferation detection of mesoCAR T cells and mesoCAR-αCD40 T cells.

The results are shown in FIG. 6. MesoCAR-αCD40 T cells have better proliferation than mesoCAR T cells.

Example 11: The Therapeutic Effect of MesoCAR and MesoCAR-αCD40 T Cells on Ovarian Cancer Mouse Xenograft Model 1: Twenty of 4-6 weeks old NSG completely immunodeficient mice, with an average weight of 22-27 g, were provided by Beijing Biocytogen Biotech Co., Ltd., and raised by a SPF animal laboratory.

2: Adhered human ovarian cancer cells SK-OV-3-luc in logarithmic growth phase cultured in vitro were digested with 0.25% trypsin, centrifuged, collected and resuspended in PBS solution. The cells were centrifuged at 1000 rmp for 2 minutes at room temperature, the supernatant was discarded and the cells were resuspended in PBS solution, centrifuged and collected, and the concentration of the cell suspension was adjusted to $5 \times 10^7$ cells/ml.

3: The OVCAR-3-luc cells were inoculated subcutaneously in the dorsum of the right rib of the mouse at 0.1 ml/mouse. 7 days after the inoculation, the size of the tumor was observed by an in vivo imager, the tumor size was measured by a vernier caliper, and the NSG immunodeficient mice were randomly divided into 5 groups: PBS group, and Mock T group, mesoCAR T group, mesoCAR-αCD40- wt T, and mesoCAR-αCD40 T group prepared according to Example 2. Each group was injected through the tail vein with corresponding T cells at $1 \times 10^7$ cells/100 ul, and PBS group was injected with 100 ul of PBS.

4: The living conditions of mice were observed every day and the change of the tumor in each mouse was observed by in vivo imager every 4 days.

Figure 7:
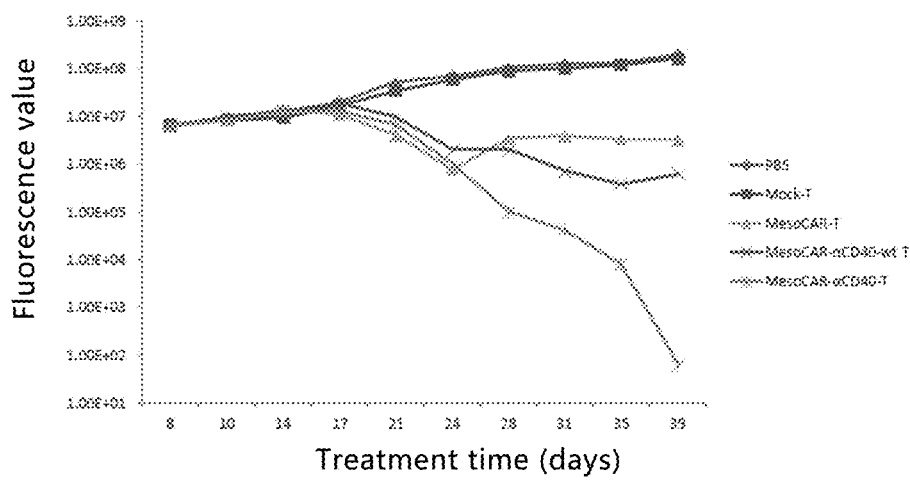
FIG. 7: The therapeutic effects of mesoCAR T cells and mesoCAR-αCD40-T cells on the SK-OV-3 ovarian cancer mouse xenograft model.

The results are shown in FIG. 7.

Example 12: Comparison of the Proliferation Rate of EHCAR-EK-28TIZ and EHCAR-EK-28TIZ-αCD40 T Cells $3 \times 10^5$ cells of Mock-T cells and the EHCAR-EK-28TIZ T cells and EHCAR-EK-28TIZ-αCD40 T cells that have been cultured for 8 days according to Example 2 were cultured in 12-well plates in a culture volume of 1 ml. 80 μL of cell-containing culture medium from each group was added to different wells of a 96-well white opaque plate, with 80 μL, nutrient solution further added to the original 12-well plate. The 96-well plate was added with 80 μL CellTiter-Glo reagent, mixed on a shaker for 2 min, and incubated at room temperature for 10 min, and then detected by a microplate reader for fluorescence value of Luc. The used CellTiter-Glo Luminescent Cell Viability Assay kit was purchased from Promega. The same detections for the cells from 12-well plates were made according to the above steps on the 9th, 10th, 11th, 12th, and 13th days of culture. Cell proliferation curves were drawn based on the detected fluorescence values.

Figure 8:
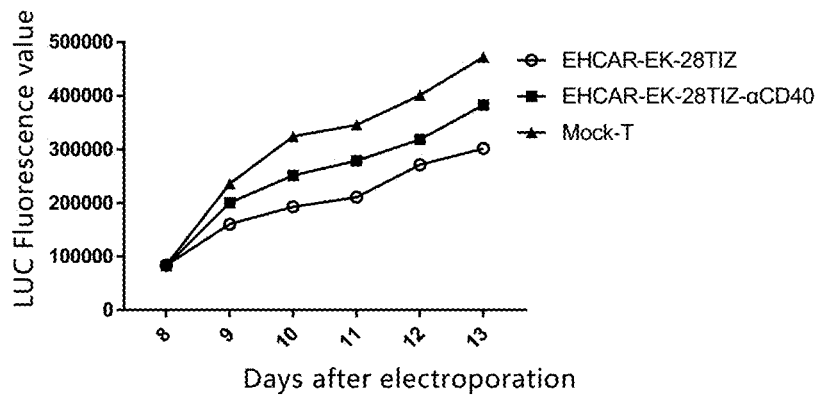
FIG. 8: Comparison of the proliferation rate of EHCAR-EK-28TIZ and EHCAR-EK-28TIZ-αCD40 T cells.

The results are shown in FIG. 8. The proliferation rate of EHCAR-EK-28TIZ-αCD40 T cells is significantly higher than that of EHCAR-EK-28TIZ T cells, indicating that the expression of CD40 antibody can promote the proliferation of CAR-T cells.

Example 13: Cell Phenotype Analysis of EHCAR-EK-28TIZ and EHCAR-EK-28TIZ-αCD40 T Cells The EHCAR-EK-28TIZ and EHCAR-EK-28TIZ-αCD40 T cells obtained in Example 2 were added into six 1.5 ml EP tubes with $1 \times 10^6$ cells/tube, washed twice with PBS, and centrifuged at 1200 rpm for 5 min; and the supernatant was discarded. Two of the tubes were added with the flow cytometry antibodies anti-CD107α-PE and anti-CD69-PE to detect activated T cell phenotype; one of the tubes was added with the flow cytometry antibodies anti-CD45RO-PECy5+ anti-CD197-FITC+ anti-CD62L-PE to detect memory T cell phenotype; one of the tubes was added with the flow cytometry antibody anti-PD1-PE to detect the inhibitory T cell phenotype; and the other 2 tubes were added with the isotype control flow cytometry antibodies IgG1-PE and IgG1-PE+IgG2a-PECy5+IgG2a-PE; 2 μl for each antibody (Jackson ImmunoResearch). The precipitate was flicked to make it mix evenly; the cells were incubated at room temperature in the dark for 30 min, washed with PBS once, and centrifuged at 1200 rpm for 5 min, the supernatant was discarded and 400 μl of normal saline was added, and the cells were transferred to a flow tube, and analyzed on the machine.

Figure 9A:
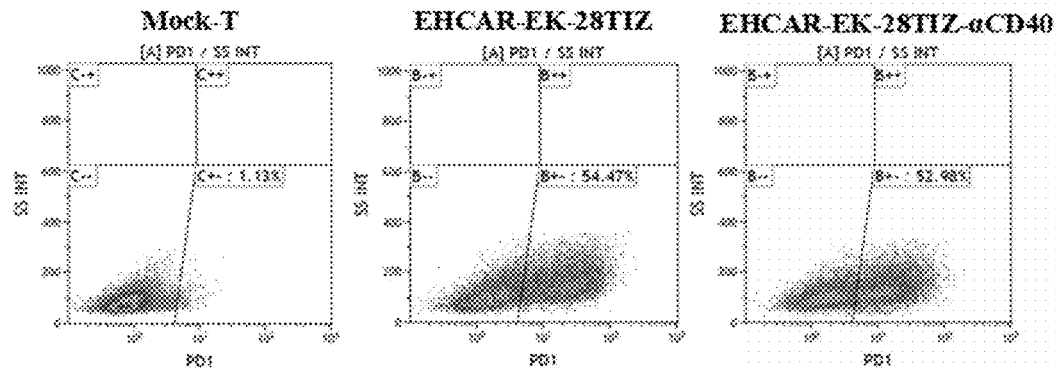
FIG. 9A-9D: Phenotype analysis of EHCAR-EK-28TIZ, and EHCAR-EK-28TIZ-αCD40 T cells; 9A represents the aging phenotype CD40, 9B and 9C represent the activated phenotype CD69 and CD107α respectively, 9D represents the memory phenotype.
Figure 9B:
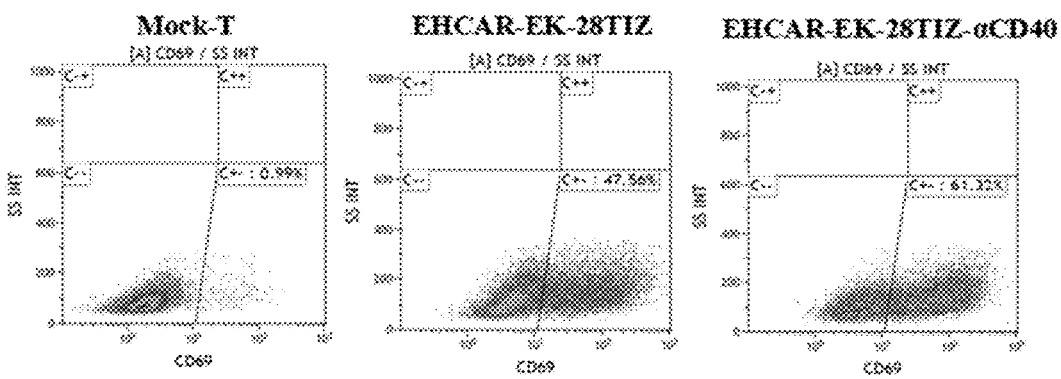
Figure 9C:
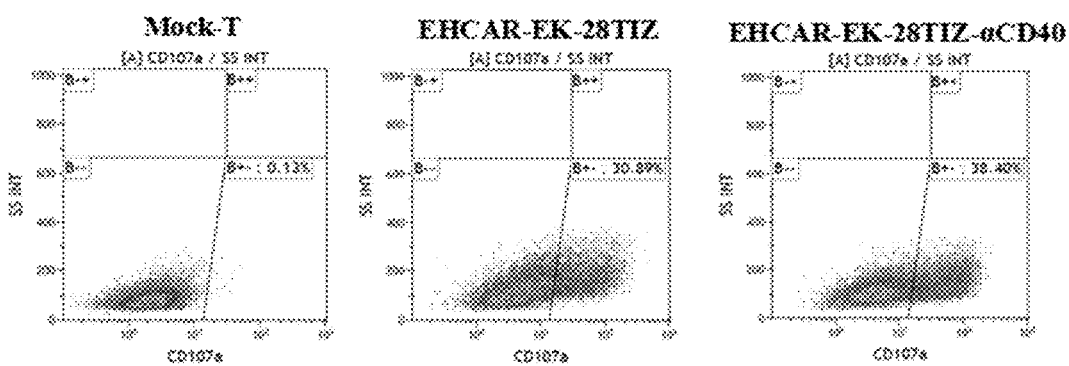
Figure 9D:
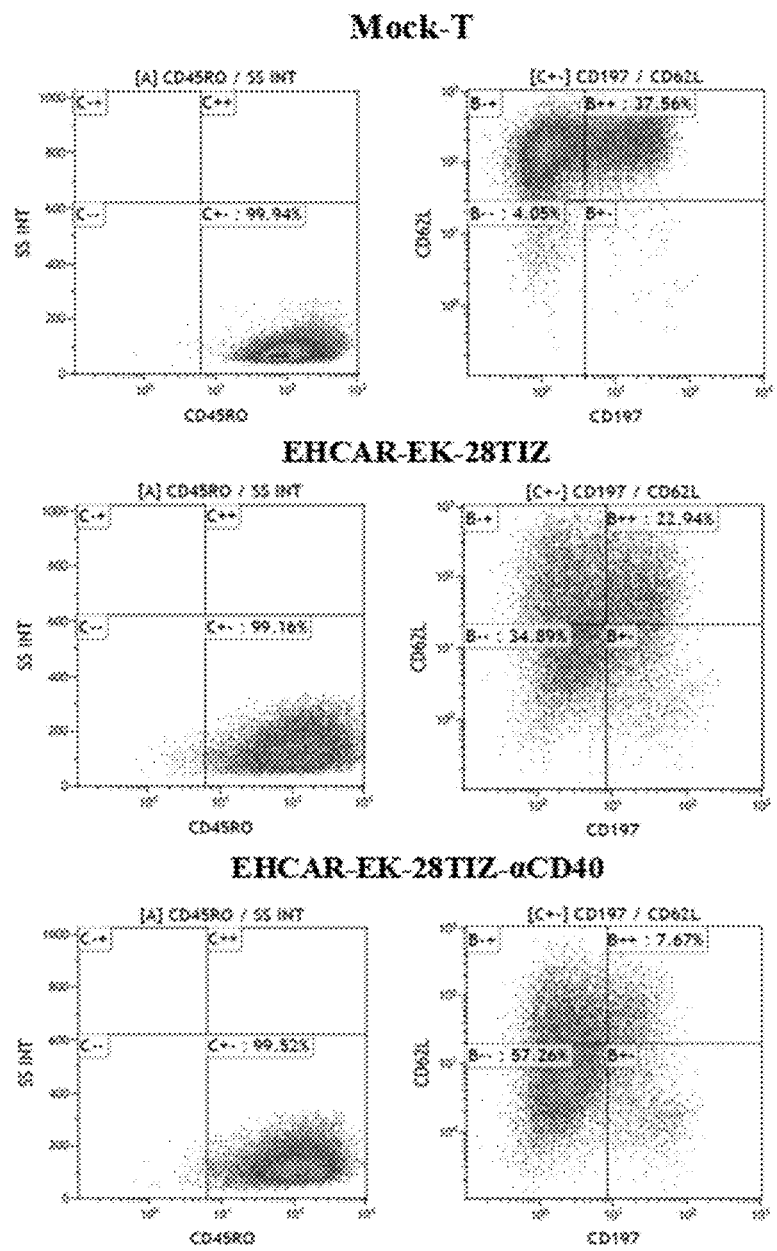

The results show that the expressions of the aging phenotype PD1 of EHCAR-EK-28TIZ and EHCAR-EK-28TIZ-αCD40 T cells by flow cytometry are similar (FIG. 9A); the expressions of the activated phenotypes CD69 and CD107α of EHCAR-EK-28TIZ-αCD40 T cells are higher than those of EHCAR-EK-28TIZ cells (FIGS. 9B and 9C); meanwhile, CD62L (L-selectin) is a marker of central memory T cells, and CD197 is a marker of effector memory T cells, and the proportion of effector T cells in EHCAR-EK-28111-αCD40 T cells is significantly higher than those of EHCAR-EK-28TIZ cells and Mock-T cells (FIG. 9D). These results indicate that the expression of CD40 antibody can promote the activation of CAR-T cells and enhance their immune killing effect.

Figure 10:
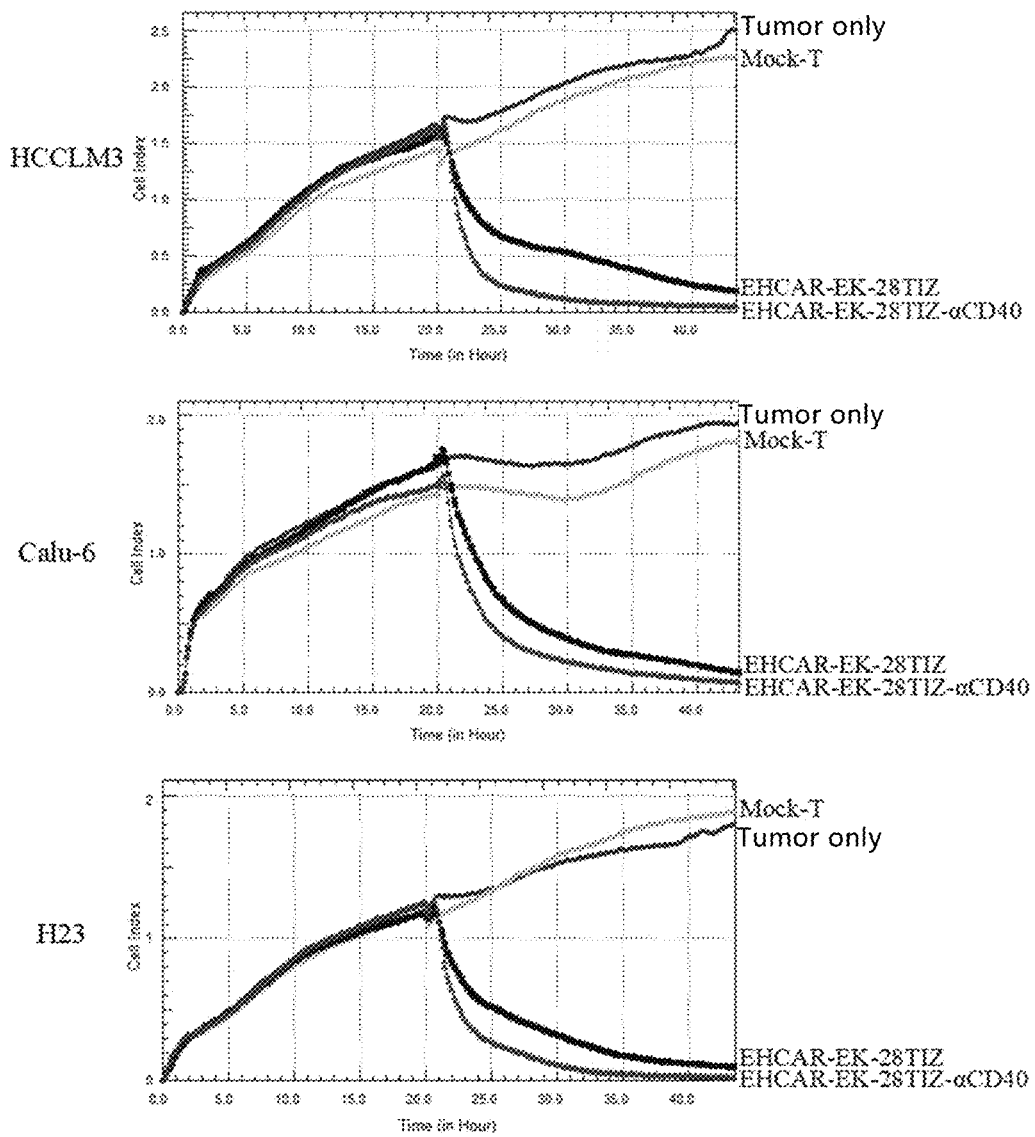
FIG. 10: Comparison of the killing by EHCAR-EK-28TIZ and EHCAR-EK-28TIZ-αCD40 T cells, including human liver cancer cells HCCLM3, human lung degenerative cancer cells Calu-6 and human non-small cell lung cancer H23.

Example 14: Comparison of the Killing Effect of EHCAR-EK-28TIZ and EHCAR-EK-28TIZ-αCD40 T Cells Target cells and effector cells that match MHC class I were selected, and Real-time label-free cell analysis system (RTCA, ACEA) was used to detect the in vitro killing effect of the EHCAR-EK-28TIZ T cells and EHCAR-EK-28TIZ-αCD40 T cells obtained in Example 2. The steps are as follows:

(1) Zero adjustment: Add 50 µl DMEM or 1640 culture medium to each well, put it into the instrument, select step 1, and adjust zero;

(2) Target cell plating: Plate human liver cancer cell HCCLM3, human lung degenerative cancer cell Calu-6 and human non-small cell lung cancer H23 (American Type Culture Collection ATCC) at $10^4$ cells/50 µl per well on a plate containing detection electrodes, let rest for a few minutes to stabilize the cells, then put them into the instrument, start step 2 to culture the cells;

(3) Adding effector cells: After 24 h culture of target cells, pause step 2 and add effector cells at 50 µl per well, with the effect target ratio of 4:1 and Mock T cells transferred with empty pNB328 as the control, start step 3 to continue co-cultivation for 24 h, then generate the cell proliferation curve; The results are shown in FIG. 10. The killing effect of EHCAR-EK-28TIZ-αCD40 T cells that self-express CD40 antibody on a variety of tumor cells is significantly greater than that of EHCAR-EK-28TIZ T cells and control T cells.

Example 15: Comparison of Cytokine Release Between EHCAR-EK-28TIZ T Cells and EHCAR-EK-28TIZ-αCD40 T cells under specific stimulation of EGFR antigen 96-well plates were coated overnight with 5 ug"ml EGFR antigen at 4° C., washed 3 times with PBS, added with $1\times10^5$ (100 ul of volume) EHCAR-EK-28TIZ and EHCAR-EK-28TIZ-αCD40 T cells prepared according to Example 2 and control Mock T cells (transferred with empty pNB328). Supernatants were collected after 24 hours of culture. The cytokine secretion of these three T cells after being stimulated by EGFR antigen was detected.

Figure 11:
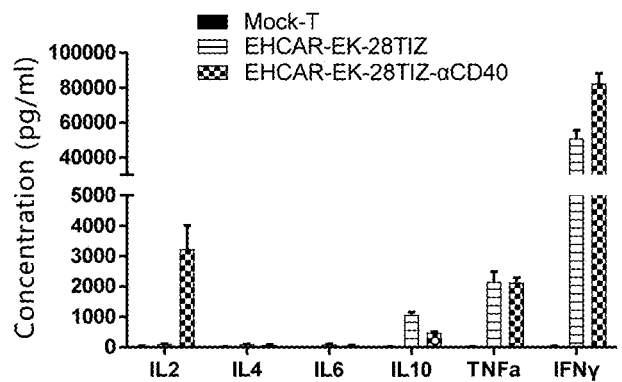
FIG. 11: Changes of secretions of cytokines IL-2, IL-4, IL-6. L-10, TNF-α and IFN-γ of EHCAR-EK-28TIZ and EHCAR-EK-28TIZ-αCD40 T cells upon the stimulation of EGFR antigen.

The results are shown in FIG. 11. The secretions of IL-2 and IFN-γ in EHCAR-EK-28TIZ-αCD40 are significantly higher than those of EHCAR-EK-28TIZ T cells and Mock-T, indicating that self-expressing CD40 agonistic antibodies can promote CAR-T cells to secrete cytokines.

Example 16: Anti-Tumor Effect of EHCAR-EK-28TIZ T Cells, EHCAR-EK-28TIZ-αCD40-Wt Cells and EHCAR-EK-28TIZ-αCD40 T Cells In Vivo Twenty NSG mice of 4-6 weeks were divided into 5 groups on average, with 4 mice of each group inoculated with liver cancer cell line HCCLM3-LUC for $1\times10^7$ per mouse. 10 days after tumor being formed, each group was injected via tail vein with PBS (100 ul PBS), Mock-T cells, EHCAR-EK-28TIZ T cells, EHCAR-EK-28TIZ-αCD40 T cells and EHCAR-EK-28TIZ-αCD40-wt T cells obtained in Example 2 ($1\times10^7$/100 ul of each), respectively. The changes of the tumor fluorescence in mice were observed and recorded.

Figure 12:
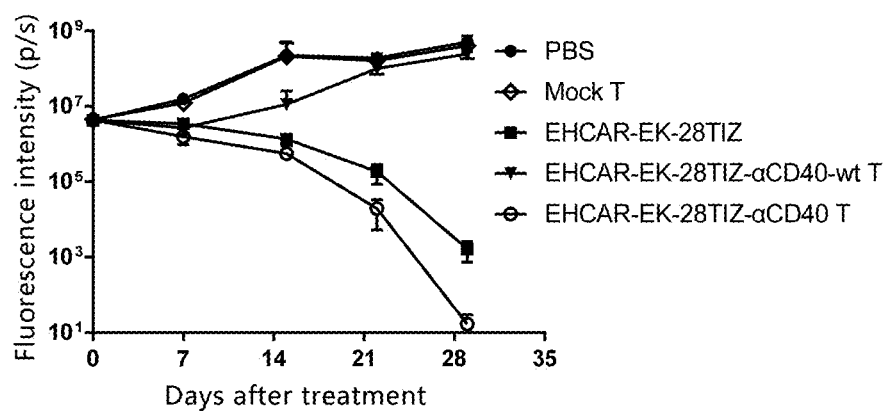
FIG. 12: Changes in fluorescence values of the tumor cells at different days after treating mice with EHCAR-EK-28TIZ T cells, EHCAR-EK-28TIZ-αCD40-wt T cells, EHCAR-EK-28TIZ-αCD40 T cells, Mock-T cells and PBS blank control.

The results show that PBS, Mock-T, EHCAR-EK-28TIZ-αCD40-wt T cells have no therapeutic effect on the tumor model, EHCAR-EK-28TIZ T cells and EHCAR-EK-28TIZ-αCD40 T cells have anti-tumor effects, and EHCAR-EK-28TIZ-αCD40 T cells are significantly better. The details are shown in FIG. 12.

Example 17: Comparison of the Proliferation Rate of Muc1CAR T and Muc1CAR-αCD40 Cells $3\times10^5$ cells of Mock-T cells and the Muc1 CAR T cells and Muc1CAR-αCD40 T cells that have been cultured for 8 days according to Example 2 were cultured in 12-well plates in a culture volume of 1 ml. 80µL, of cell-containing culture medium from each group was added to different wells of a 96-well white opaque plate, with 80µL nutrient solution further added to the original 12-well plate. The 96-well plate was added with 80 µL CellTiter-Glo reagent, mixed on a shaker for 2 min, and incubated at room temperature for 10 min, and then detected by a microplate reader for fluorescence value of Luc. The used CellTiter-Glo Luminescent Cell Viability Assay kit was purchased from Promega. The same detections for the cells from 12-well plates were made according to the above steps on the 9th, 10th, 11th, 12th, and 13th days of culture. Cell proliferation curves were drawn based on the detected fluorescence values.

Figure 13:
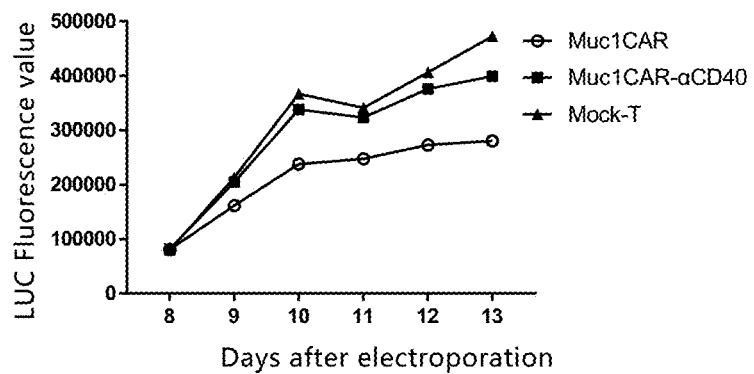
FIG. 13: Comparison of the proliferation rate of Muc1CAR T cells and Muc1CAR-αCD40 T cells.

The results are shown in FIG. 13. The proliferation rate of Muc1CAR-αCD40 T cells is significantly higher than that of Muc1 CAR T cells, indicating that the expression of CD40 antibody can promote the proliferation of CAR-T cells.

Example 18: Cell Phenotype Analysis of Muc1CAR T and Muc1CAR-αCD40 T Cells

The Muc1CAR and Muc1CAR-αCD40 T cells obtained in Example 2 were added into seven 1.5 ml EP tubes with $1\times10^6$ cells/tube, washed twice with PBS, and centrifuged at 1200 rpm for 5 min, and the supernatant was discarded. One of the tubes was added with the flow cytometry antibody anti-CD25-PE to detect activated T cell phenotype; one of the tubes was added with the flow cytometry antibodies anti-CD45RO-PECy5+ anti-CD197-FITC+ anti-CD62L-PE to detect memory T cell phenotype; two of the tubes were added with the flow cytometry antibodies anti-PD1-PE and anti-LAG3-Alexa Fluor 647 to detect the inhibitory T cell phenotype; and the other 3 tubes were added with the isotype control flow cytometry antibodies IgG1-PE, IgG1-PE+ IgG2a-PECy5+IgG2a-PE and IgG1 Alexa Fluor 647; 2 µl for each antibody (Jackson ImmunoResearch). The precipitate was flicked to make it mix evenly, the cells were incubated at room temperature in the dark for 30 min, washed with PBS once, and centrifuged at 1200 rpm for 5 min, the supernatant was discarded and 400 al of normal saline was added, and the cells were transferred to a flow tube, and analyzed on the machine.

Figure 14A:
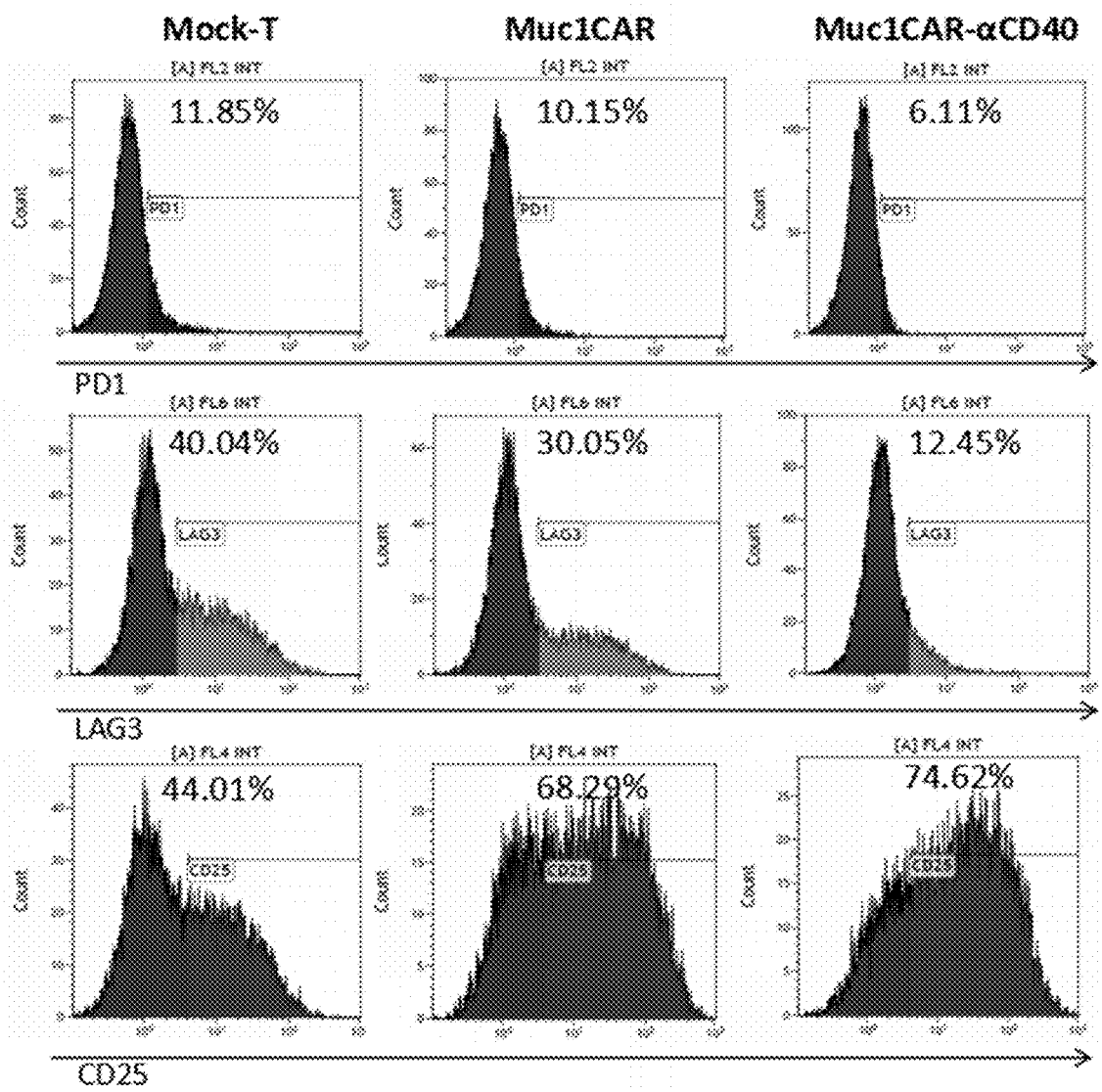
FIGS. 14A-14B: Phenotype analysis of Muc1 CAR T cells and Muc1CAR-αCD40 T cells.
Figure 14B:
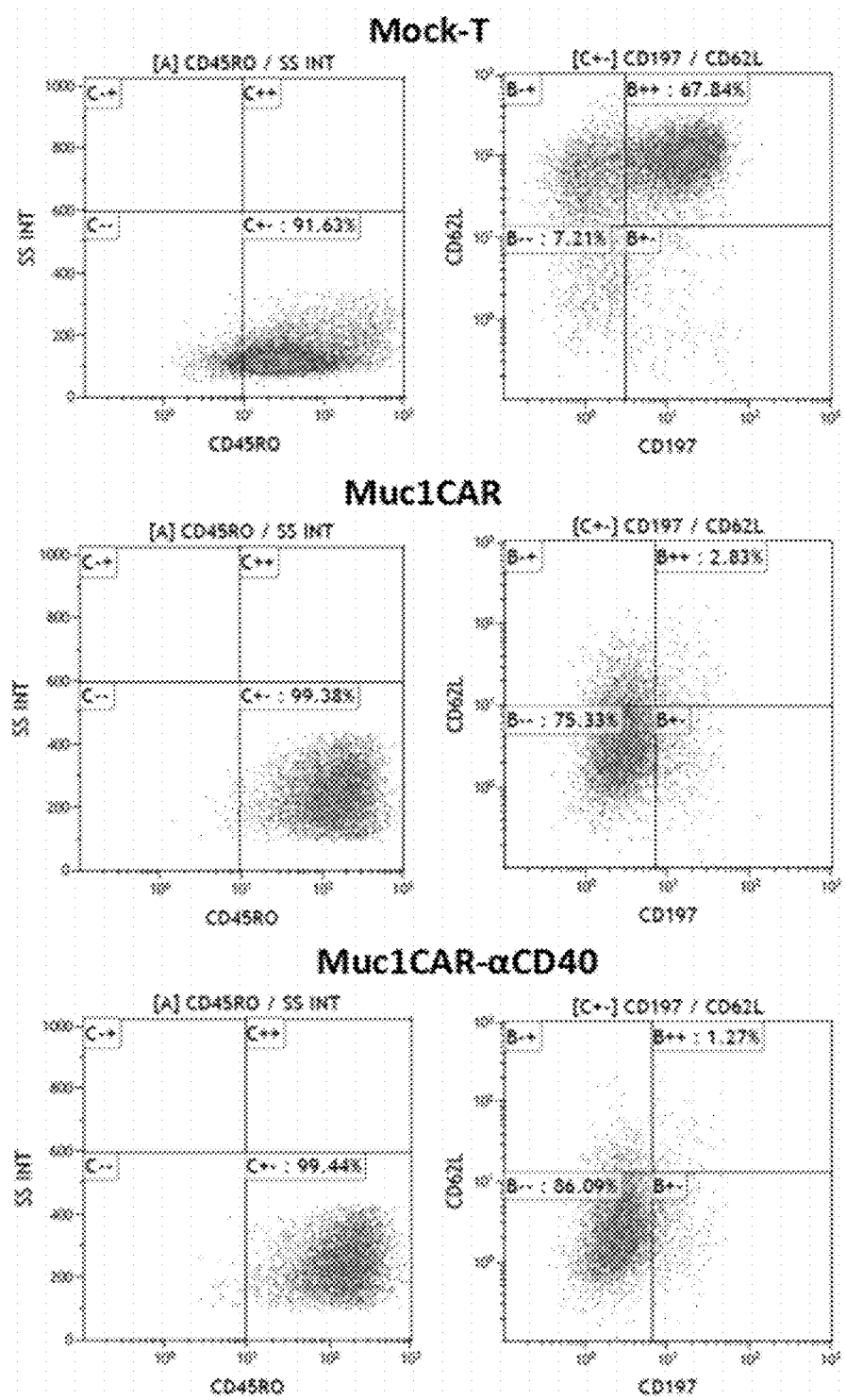

The results showed that the expressions of the aging phenotypes PD1 and LAG3 of Muc1CAR-αCD40 T cells by flow cytometry are lower than that of Muc1CAR T cells, and the expression of the activated phenotype CD25 of Mud CAR-αCD40 T cells is higher than that of Muc1CAR T cells (FIG. 14A); meanwhile, CD62L (L-selectin) is a marker of central memory T cells, and CD197 is a marker of effector memory T cells, and the proportion of effector T cells in Muc1CAR-αCD40 T cells is significantly higher than those of Muc1CAR T cells and Mock-T cells (FIG. 14B). These results indicate that the expression of CD40 antibody can promote the activation of CAR-T cells and enhance their immune killing effect.

Example 19: Comparison of the Killing Effect by Muc1CAR T and Muc1CAR-αCD40 T Cells Target cells and effector cells that match MHC class I were selected, and Real-time label-free cell analysis system (RTCA, ACEA) was used to detect the in vitro killing effect of the Muc1CAR T cells and Muc1CAR-αCD40 T cells obtained in Example 2. The steps are as follows:
(1) Zero adjustment: add 50 μl DMEM or 1640 culture medium to each well, put it into the instrument, select step 1, and adjust zero;
(2) Target cell plating: Plate human liver cancer cell HCCLM3 and human non-small cell lung cancer 1-123 (American Type Culture Collection ATCC) at $10^4$ cells/50 μl per well on a plate containing detection electrodes, let rest for a few minutes to stabilize the cells, then put them into the instrument, start step 2 to culture the cells;
(3) Adding effector cells: After 24 h culture of target cells, pause step 2 and add effector cells at 50 μl per well, with the effect target ratio of 4:1 and Mock T cells transferred with empty pNB328 as the control, start step 3 to continue co-cultivation for 24 h, then generate the cell proliferation curve.

Figure 15:
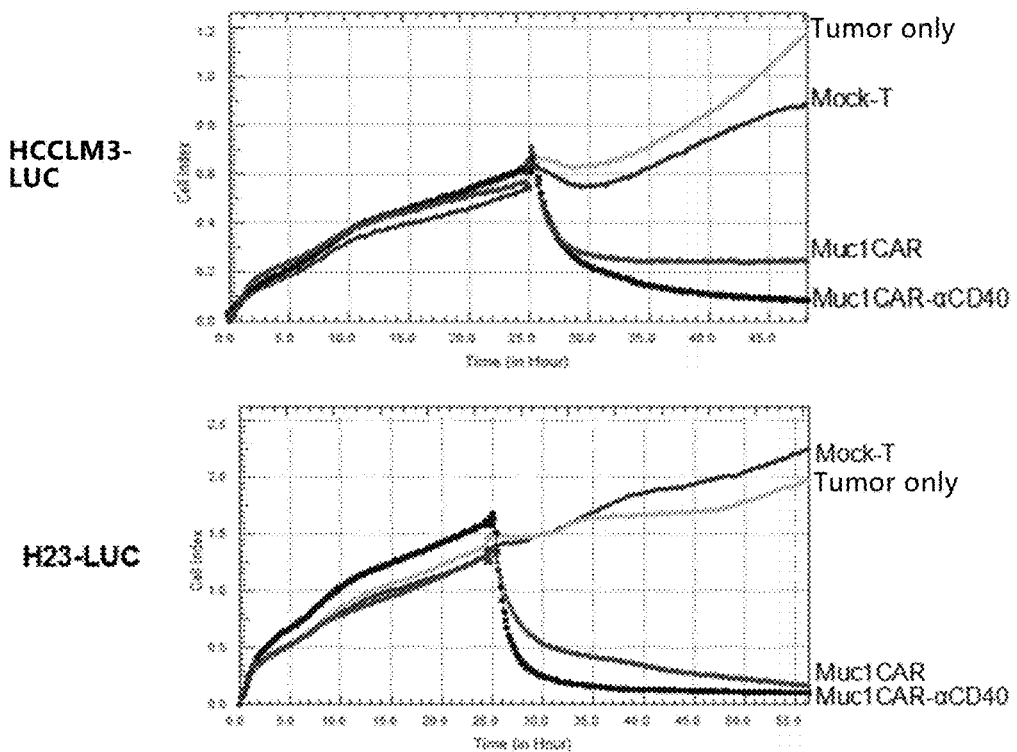
FIG. 15: Comparison of the killing by Muc1CAR T cells and Muc1CAR-αCD40 T cells, including human liver cancer cells HCCLM3 and human non-small cell lung cancer H23.

The results are shown in FIG. 15. The killing effect of Muc1CAR-αCD40 T cells that self-express CD40 antibody on a variety of tumor cells is significantly greater than those of Muc1CAR
T cells and control T cells.

Example 20: Comparison of Cytokine Release Between Muc1CAR T and Muc1CAR-αCD40 T Cells Under Specific Stimulation of Muc1 Antigen 96-well plates were coated overnight with 5 ug/ml Muc1 antigen at 4° C., washed 3 times with PBS, added with $1\times10^5$ (100 ul of volume) Muc1CAR T cells and Muc1CAR-αCD40 T cells prepared according to Example 2 and control Mock T cells (transferred with empty pNB328). Supernatants were collected after 24 hours of culture. The cytokine secretion of these three T cells after being stimulated by Muc1 antigen was detected.

Figure 16:
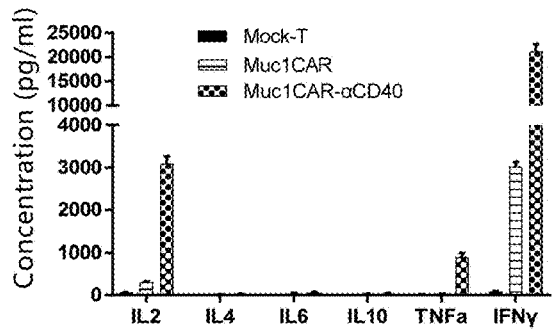
FIG. 16: Changes of secretions of cytokines IL-2, IL-4, IL-6, IL-10, TNF-α and IFN-γ of Muc1CAR T cells and Muc1CAR-αCD40 T cells upon the stimulation of Muc1 antigen.

The results are shown in FIG. 16. The secretions of IL-2, TNFα and IFN-γ by Muc1CAR-αCD40 T cells are significantly higher than those by Muc1 CAR T cells and Mock-T, indicating that self-expressing CD40 agonistic antibodies can promote the secretion of cytokines by CAR-cells.

Example 21: Anti-Tumor Effect of Muc1 CAR-T, Muc1CAR-αCD40-Wt T Cells and Muc1CAR-αCD40 T Cells In Vivo Twenty NSG mice of 4-6 weeks were divided into 5 groups on average, with 4 mice of each group inoculated with liver cancer cell line HCCLM3-LUC for $1\times10^7$ per mouse. 10 days after tumor being formed, each group was injected via tail vein with PBS (100 ul PBS), Mock T cells, Muc1CAR-T cells, Muc1CAR-αCD40 T cells and Muc1CAR-αCD40-wt T cells obtained in Example 2 ($1\times10^7$/100 ul of each), respectively. The changes of the tumor fluorescence in mice were observed and recorded.

Figure 17:
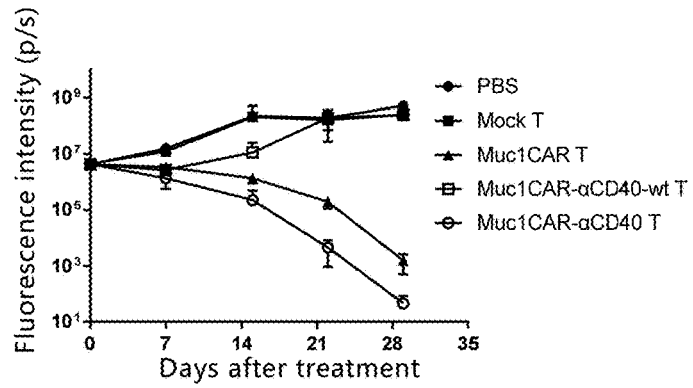
FIG. 17: Changes in fluorescence values of the tumor cells at different days after treating mice with Muc1CAR T cells, Muc1CAR-αCD40-wt T cells, Muc1CAR-αCD40 T cells, Mock-cells and PBS blank control.

The results show that PBS, Mock-T, Muc1CAR-αCD40-wt T cells have no therapeutic effect on the tumor models, and Muc1CAR-T and Muc1CAR-αCD40 T cells have anti-tumor effects, with Muc1CAR-αCD40 T cells having significantly better effects. The details are shown in FIG. 17.

Figure 18:
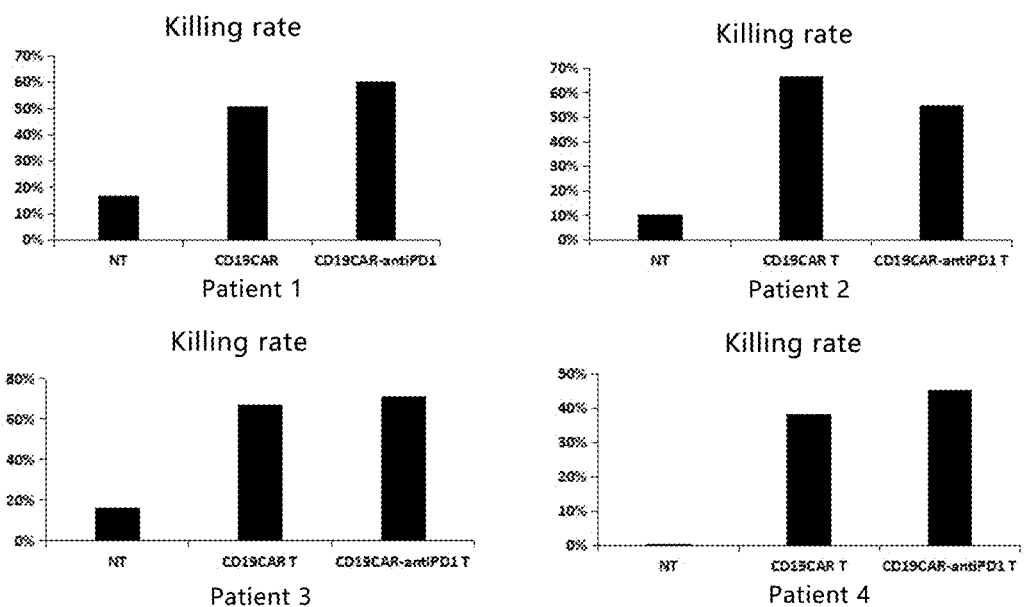
FIG. 18: Detection of the killing effect of CD19CAR-anti PD1 pluripotent T cells.

Example 22: Killing Assay of Mock T Cells, CD19CAR T Cells, and CD19CAR-antiPD1 T Cells on the Cultured Tumor Cells In Vitro Target cells and effector cells that match MHC class I were selected, and DELFIA EuTDA Cytotoxicity Test was used to detect the killing effect of the CAR T cells in vitro. The steps are as follows:
(1) Centrifuge, collect Raji cells, and wash once with PBS;
(2) Centrifuge, collect cell pellet, resuspend the cells in 1640 medium and count cell number, adjust the cell density to $1\times10^6$/ml;
(3) Add 5 ul of fluorescence-enhancing ligand in 2-4 ml of the above cells, then place the cells in 37° C., 5% $CO_2$ cell incubator for 20 min;
(4) Wash the cells 3-5 times with PBS;
(5) Centrifuge, collect the cell pellet and resuspend the cells in 1640 medium and count cell number, adjust the cell density to $5\times10^4$/ml, and add 100 ul of the cell suspension to a 96-well culture plate.
(6) Count cell numbers for the Mock T cells, CD19CAR T cells and CD19CAR-antiPD1 T cells prepared in Example 2, add 100 ul of the cell suspensions to the above Raji cells according to different effective target ratios 4:1, with a high control group (tumor cells lysed by lysis buffer), a low control group (only tumor cells), a blank control group (only medium);
(7) Place in 37° C., 5% $CO_2$ cell incubator for 20 min and co-culture for 3 h;
(8) Transfer 20 ul culture supernatant to 96-well whiteboard;
(9) Add 200 ul Europium solution;
(10) Shake at room temperature for 15 minutes;
(11) Generate readings by time-resolved fluorescence detection in microplate reader;

The results are shown in FIG. 18. CD19CAR T cells and CD19CAR-antiPD1 T have strong and comparable killing effects on tumor cells.

Example 23: Detection of Differences of Activation Phenotype and Cytokine Secretion Between Mock T Cells, CD19CAR T Cells and CD19CAR-antiPD1 T Cell by Flow Cytometry 1. The suspended Mock T cells, CD19CAR T cells and CD19CAR-antiPD1 T cells prepared in Example 2 were washed twice with PBS, centrifuged at 1200 rpm for 5 min, and added with 2 ul of the isotype control antibody IgG1-PE, the fluorescent flow cytometry antibodies anti-CD69-PE, anti-KLRG1-PE, anti-PD1-PE; isotype control antibody IgG1-PC5, the fluorescent flow cytometry antibody anti-CD107-PC5; isotype control antibody IgG1 FITC, fluorescent flow cytometry antibody anti-CD62L-FITC; isotype control antibody IgG1-PC5, fluorescent flow cytometry antibody anti-CD45RO-PC5; isotype control antibody IgG1-PE, fluorescent flow cytometry antibody anti-CCR7-PE. The precipitate was flicked to make it mix evenly, the cells were incubated at room temperature in the dark for 30 min, and washed with PBS once, 400 μl PBS was added and the cells were transferred to a flow tube, and then assayed on the machine.

Figure 19:
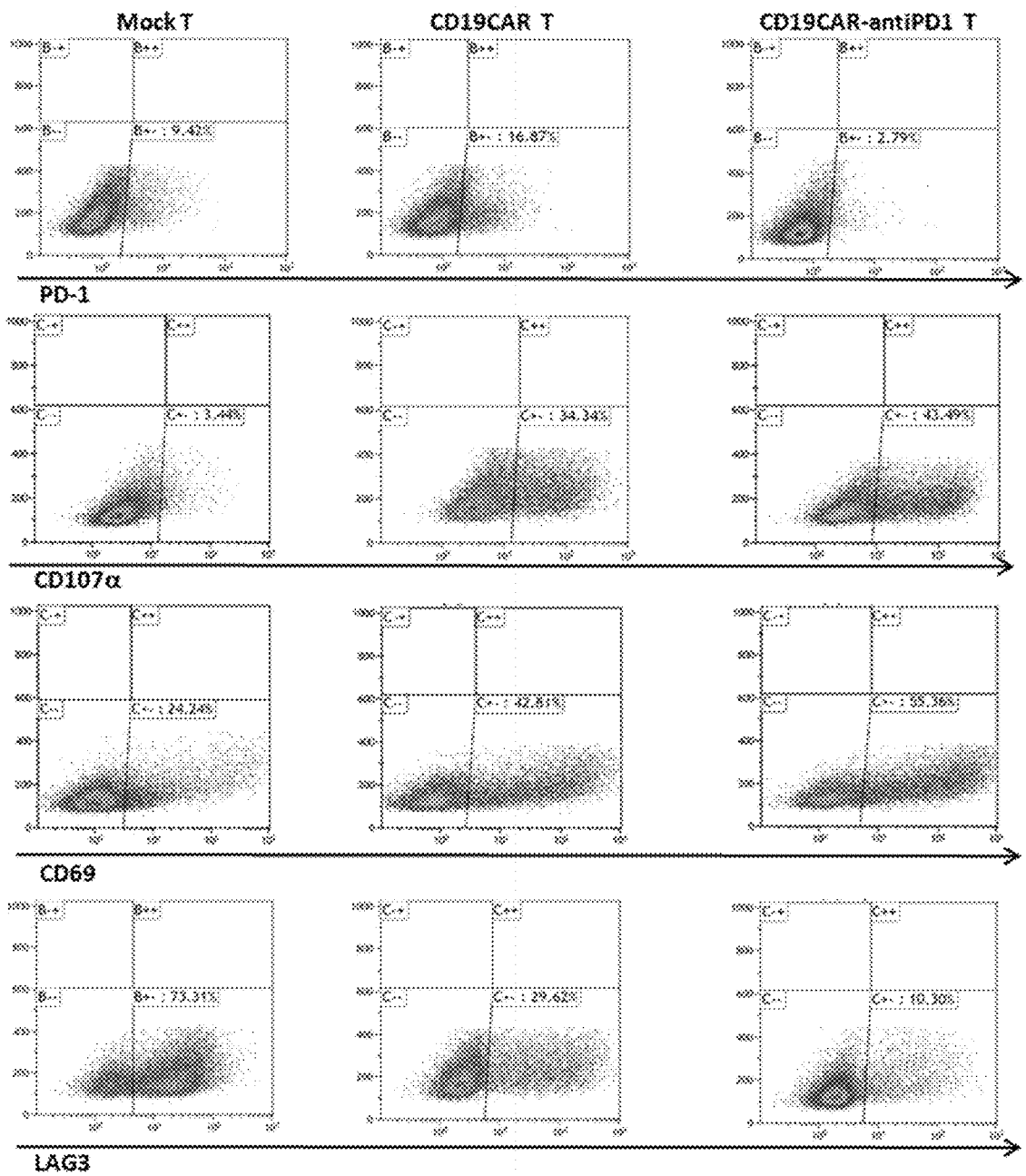
FIG. 19: CD19CAR-anti PD1 pluripotent T cells can enhance the killing activity of T cells in vitro.
Figure 19:
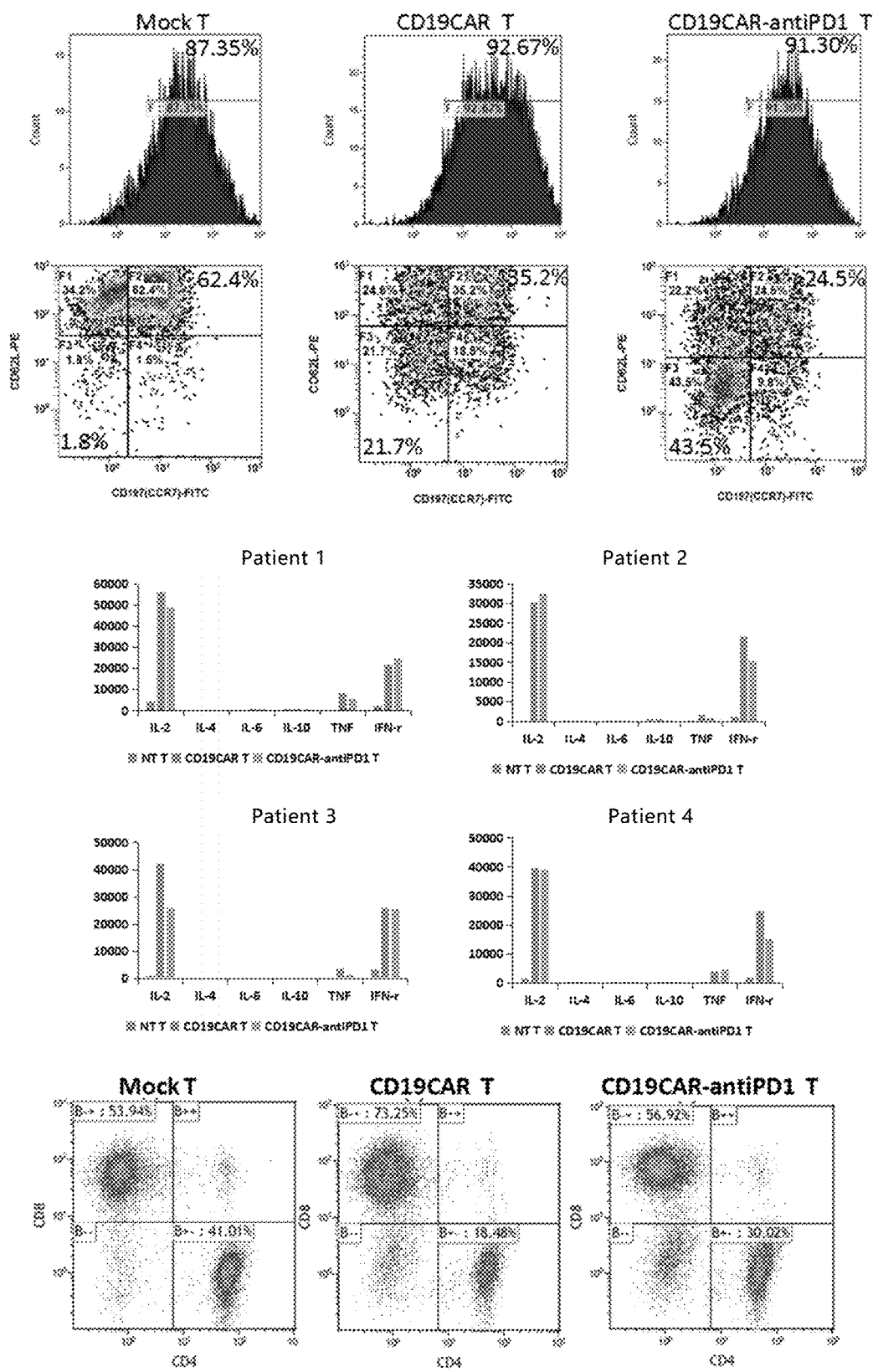

The results are shown in FIG. 19 (panels 1 and 2). The PD-1 single-chain antibody secreted by CD19CAR-antiPD1 T cells can block the PD-1 protein on the surface of T cells well. CD19CAR T cells and CD19CAR-antiPD1 T cells have obvious killing activity in vitro and can also promote the formation of memory T, while activation marker CD69 is significantly higher than Mock T cells and depletion marker LAG3 is significantly lower than Mock T cells.

2. 24-well plates were coated overnight with 5 ug/ml CD19 antigen at 4° C., washed 3 times with PBS, added with $3 \times 10^5$ Mock T cells, CD19CAR T cells and CD19CAR-antiPD1 T cells. Supernatants were collected after 24 hours of culture. BD™CBA Human Th1/Th2 Cytokine Kit II was used to detect the secretion of cytokines of CD19CAR T cells and CD19CAR-antiPD1 T cells after stimulated by CD19 antigen:
  (1) Mix human IL-2, IL-4, IL-6, IL-10, TNF-α, IFN-γ capture magnetic beads by vortex, add 50 ul of mixed beads to each tube;
  (2) Add 50 ul of human Th1/Th2 cytokine standard (diluted to 5000 pg/ml, 2500 pg/ml, 1250 pg/ml, 625 pg/ml, 312.5 pg/ml, 156 pg/ml, 80 pg/ml, 40 pg/ml, 20 pg/ml, or 0 pg/ml) and 50 ul of the sample to be tested (diluted by 2-fold with the diluents);
  (3) Add 50 ul of human Th1/Th2-II-PE detection antibody to each tube;
  (4) Incubate at room temperature in the dark for 3 h;
  (5) Add 1 ml of washing buffer to each tube, centrifuge at 200 for 5 min, and discard the supernatant;
  (6) Add 300 ul of washing buffer to each tube to resuspend the cells, and transfer the cells to a flow cytometry tube to detect the fluorescence value by a flow cytometer.

The results are shown in FIG. 19 (the third panel). The secretions of IL-2, TNF-α and IFN-α of CD19CAR T cells and CD19CAR-antiPD1 T cells are greatly improved as compared to Mock T cells. The secretions of IL-4, IL-6 and IL-10 of the three cells are not substantially different.

3. $1 \times 10^6$ CD19CAR T cells and CD19CAR-antiPD1 T cells were added to 1.5 ml EP tubes respectively, washed twice with PBS, centrifuged at 1200 rpm for 5 min, added with 2 ul of α-CD3CD4CD8 antibody, incubated at room temperature in the dark for 30 min, and washed once with PBS, 400 ul PBS was added, and the cells were transferred to the flow tube, and assayed on the machine.

The results are shown in FIG. 19 (the fourth panel). No big difference is shown in the percentages of $CD3^+CD4^+$ and $CD3^+CD8^+$ cells in CD19CAR T cells, CD19CAR-antiPD1 T cells and Mock T cells.

Example 24: Functional Assay of CD19CAR T Cells, CD19CAR-antiPD1 T Cells and CD19CAR-antiPD1-Wt T Cells In Vivo This example used twelve of 4-6 weeks old NSG completely immunodeficient mice, with an average weight of 22-27 g, provided by Beijing Biocytogen Biotech Co., Ltd., and raised by a SPF animal laboratory.

Human B-cell lymphoma Raji-luc cells in logarithmic growth phase cultured in vitro were centrifuged, collected and resuspended in PBS solution. The cells were centrifuged at 3000 g for 2 minutes at room temperature, the supernatant was discarded and the cells were resuspended in PBS solution, centrifuged and collected, and the concentration of the cell suspension was adjusted to $5 \times 10^7$ cells/ml. The Raji-luc cells were inoculated subcutaneously in the dorsum of the right rib of the mouse at 0.1 ml/mouse. About 10 days after the inoculation, the size of the tumor was observed by an in vivo imager, and the NSG immunodeficient mice were randomly divided into 4 groups: PBS group, Mock T group, CD19CAR T group, CD19CAR-antiPD1 T, and CD19CAR-antiPD1-wt T group (T cells prepared according to Example 2). Each group was injected through the tail vein with corresponding T cells at $1 \times 10^7$ cells/100 ul, and PBS group was injected with 100 ul of PBS. The living conditions of mice were observed every day and the change of the tumor in each mouse was observed by in vivo imager every 7-8 days.

Figure 20:
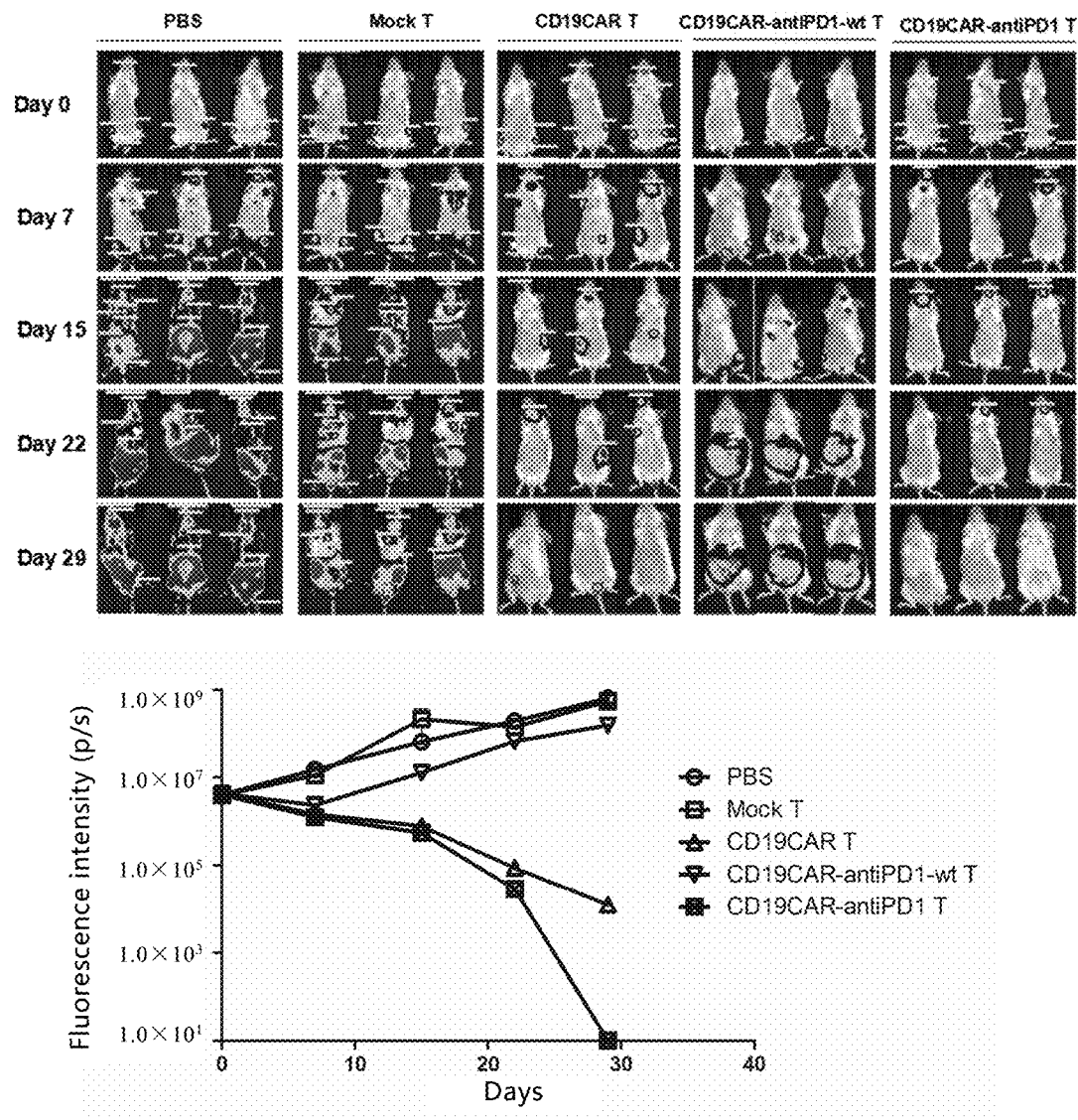
FIG. 20: Detection of the killing effect of CD19CAR-anti PD1 T cell in vivo.

The results are shown in FIG. 20.

Example 25: Comparison of the Killing Effect by Meso3CAR T and MesoCAR-antiPD1 T Cells Real-time label-free cell analysis system was used to detect the killing effect of meso3CAR T cells and meso-CAR-antiPD1 T cells prepared in Example 2 on tumor cells in vitro.

Specifically, target cells and effector cells that match MHC class I were selected, and Real-time label-free cell analysis system (RTCA, ACEA) was used to detect the killing effect of the above two CAR-T cells in vitro. The steps are as follows:
  (1) Zero adjustment: Add 50 μl DMEM or 1640 culture medium to each well, put it into the instrument, select step 1, and adjust zero;
  (2) Target cell plating: Plate cervical cancer cell Hela, ovarian cancer cell SK-OV-3, gastric cancer cell HGC-27 (American Type Culture Collection ATCC) at $10^4$ cells/50 μl per well on a plate containing detection electrodes, let rest for a few minutes to stabilize the cells, then put them into the instrument, start step 2 to culture the cells;
  (3) Adding effector cells: After 24 h culture of target cells, pause step 2 and add effector cells at 50 μl per well, with the effect target ratio of 4:1 and Mock T cells without a transferred plasmid as a control, start step 3 to continue co-cultivation for 24 h, then generate the cell proliferation curve.

Figure 21:
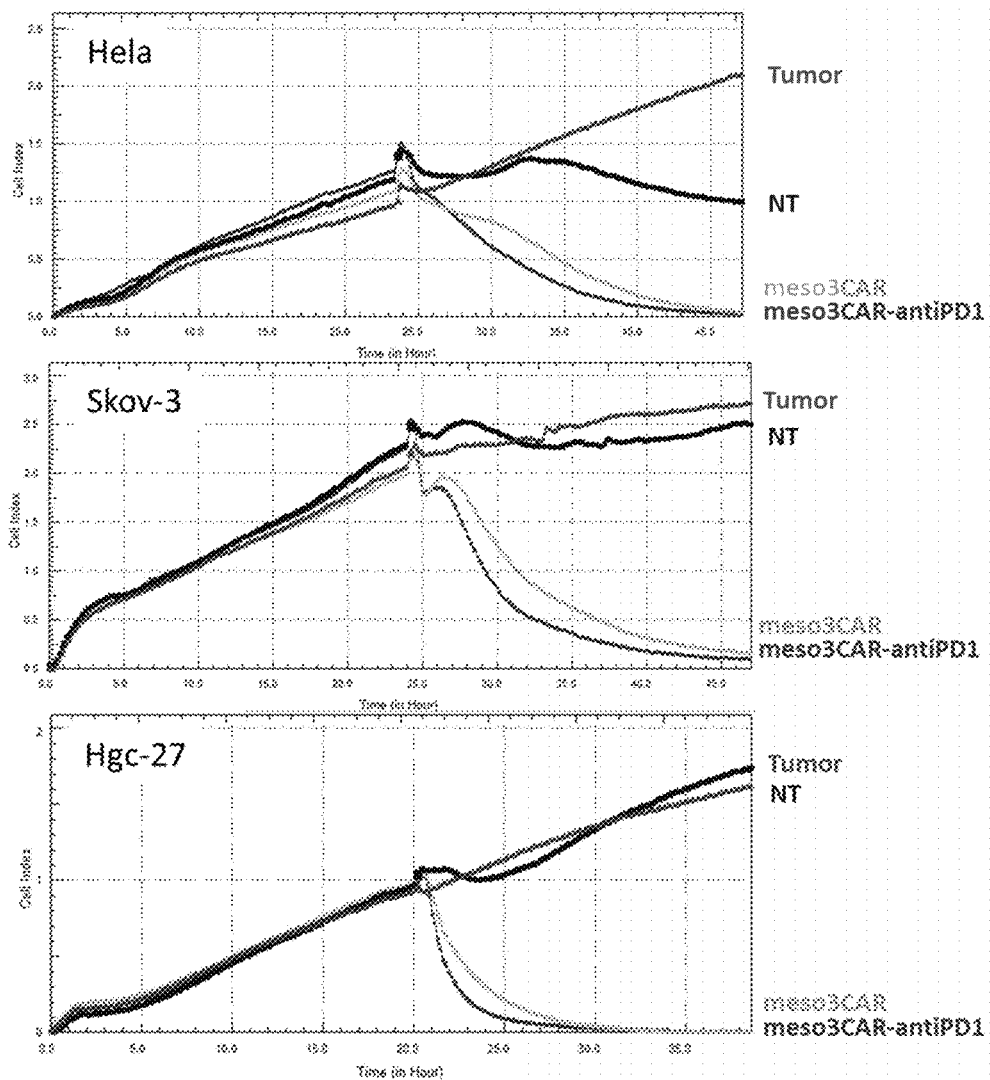
FIG. 21: The killing of mesoCAR-antiPD1 T cells on cervical cancer cells Hela, ovarian cancer cells SK-OV-3 and gastric cancer cells HGC-27.

The results are shown in FIG. 21. The mesoCAR-antiPD1 T cells that self-express PD1 antibodies have substantially the same killing effect with meso3CAR T cells alone. The expression of antibody does not affect the CAR-T function.

Example 26: Comparison of Cytokine Release Between Meso3CAR and MesoCAR-antiPD1 T Cells Under Specific Stimulation of Mesothelin Antigen 96-well plates were coated overnight with 2 ug/ml mesothelin antigen at 4° C., washed 3 times with PBS, added with $1 \times 10^5$ meso3CAR and mesoCAR-antiPD1 T cells prepared according to Example 2 and control Mock T cells. Supernatant was collected after 24 hours of culture. BD™CBA Human Th1/Th2 Cytokine Kit II was used to detect the cytokine secretion of these three T cells upon stimulation by mesothelin antigen. The particular steps are as follows:
  (1) Mix human IL-2, IL-4, IL-6, IL-10, TNF-α, IFN-γ capture magnetic beads by vortex, add 50 ul of mixed beads to each tube;
  (2) Add 50 ul of human Th1/Th2 cytokine standard (diluted to 5000 pg/ml, 2500 pg/ml, 1250 pg/ml, 625 pg/ml, 312.5 pg/ml, 156 pg/ml, 80 pg/ml, 40 pg/ml, 20 pg/ml, or 0 pg/ml) and 50 ul of the sample to be tested (diluted by 2-fold with the diluents);
(3) Add 50 ul of human Th1/Th2-II-PE detection antibody to each tube;
(4) Incubate at room temperature in the dark for 3 h;
(5) Add 1 ml of washing buffer to each tube, centrifuge at 200 for 5 min, and discard the supernatant;
(6) Add 300 ul of washing buffer to each tube to resuspend the cells, and transfer the cells to a flow cytometry tube to detect the fluorescence value by a flow cytometer.

Figure 22:
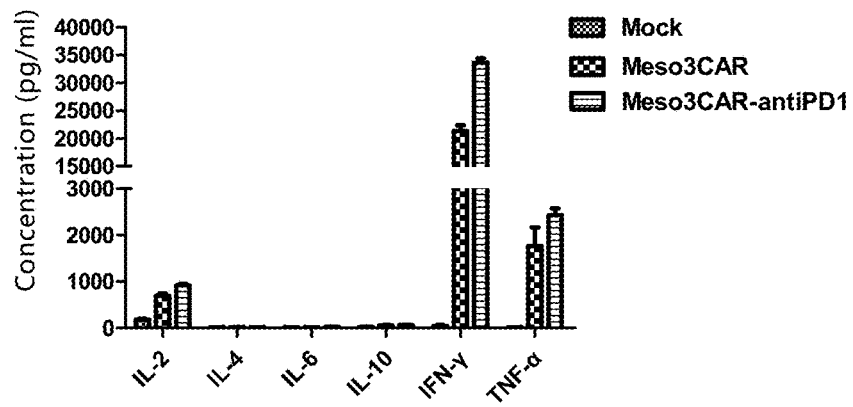
FIG. 22: Changes of secretions of cytokines IL-2, IL-4, IL-6, IL-10, TNF-α and IFN-γ of mesoCAR-antiPD1 upon the stimulation of mesothelin antigen.

The results are shown in FIG. 22. There is no significant difference in the amount of cytokine secretion between mesoCAR-antiPD1 T cells that self-express PD1 antibody and meso3CAR T cells alone.

Example 27: The Therapeutic Effect of Meso3CAR and MesoCAR-antiPD1 T Cells on Ovarian Cancer Mouse Xenograft Model 1. 25 of 4-6 weeks old NSG completely immunodeficient mice, with an average weight of 22-27 g, were provided by Beijing Biocytogen Biotech Co., Ltd., and raised by a SPF animal laboratory.
2. Adhered human ovarian cancer cells SK-OV-3-luc in logarithmic growth phase cultured in vitro were digested with 0.25% trypsin, centrifuged, collected and resuspended in PBS solution. The cells were centrifuged at 1000 rmp for 2 minutes at room temperature, the supernatant was discarded and the cells were resuspended in PBS solution, centrifuged and collected, and the concentration of the cell suspension was adjusted to $5\times10^7$ cells/ml.
3. The SK-OV-3-luc cells were inoculated subcutaneously in the dorsum of the right rib of the mouse at 0.1 ml/mouse. 7 days after the inoculation, the fluorescence intensity was observed by an in vivo imager, and the NSG immunodeficient mice were randomly divided into 5 groups. Each group was injected through the tail vein with corresponding T cells at $1\times10^7$ cells/100 ul, and PBS group was administrated with 100 ul of PBS.
4. The living conditions of mice were observed every day and the change of the tumor in each mouse was observed by in vivo imager every 4 days.

Figure 23:
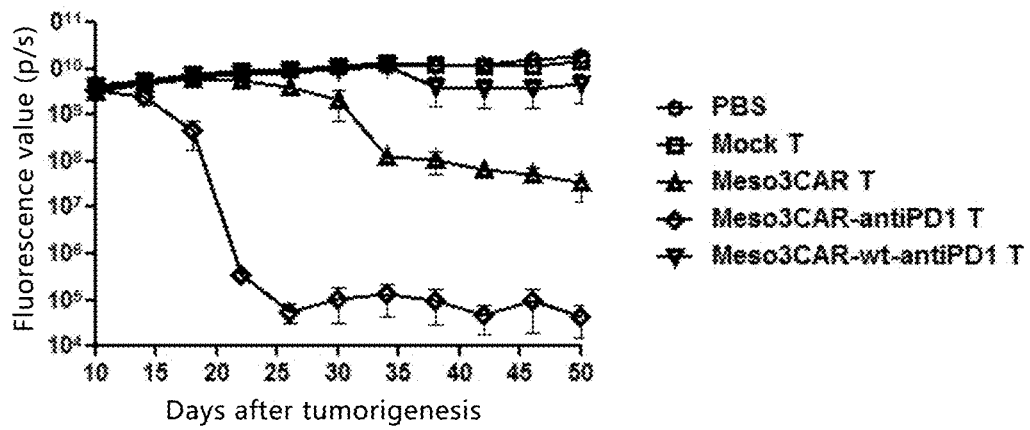
FIG. 23: The therapeutic effects of meso3CAR T cells and mesoCAR-antiPD1 T cells on the SK-OV-3 ovarian cancer xenograft mouse model.

The results are shown in FIG. 23. In the SK-OV-3 ovarian cancer mouse xenograft model, MesoCAR-antiPD1 T cells have a significantly better therapeutic effect than Meso3CAR T cells, while Meso3CAR-wt-antiPD1 T cells have substantially no effect.

Figure 28:
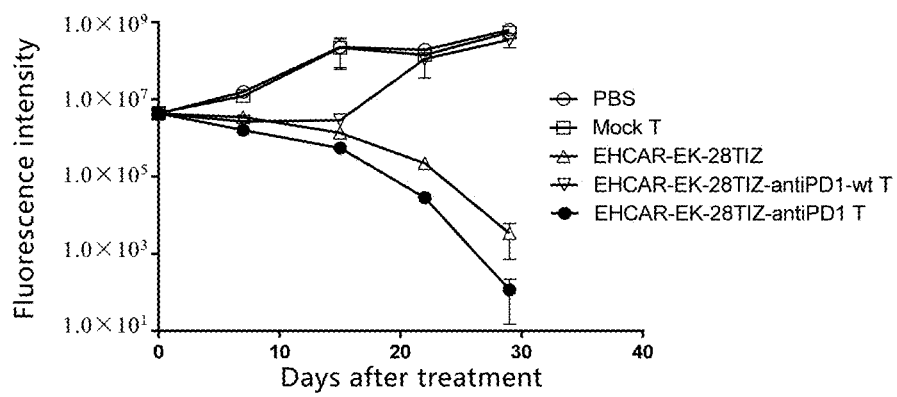
FIG. 28: Changes in fluorescence values of the tumor cells at different days after treating mice with EHCAR-EK-28TIZ T cells, EHCAR-EK-28TIZ-antiPD1-wt T cells, EHCAR-EK-28TIZ-antiPD1 T cells, Mock-T cells and PBS blank control.

FIG. 28: Comparison of the proliferation rate of EHCAR-EK-28112 and EHCAR-EK-28TIZ-antiPD1 T cells $3\times10^5$ cells of Mock-T cells and the EHCAR-EK-28TIZ T cells and EHCAR-EK-28TIZ-antiPD1 T cells that have been cultured for 8 days according to Example 2 were cultured in 12-well plates in a culture volume of 1 ml. 80 μL of cell-containing culture medium from each group was added to different wells of a 96-well white opaque plate, with 80 μL nutrient solution further added to the original 12-well plate. The 96-well plate was added with 80 μL CellTiter-Glo reagent, mixed on a shaker for 2 min, and incubated at room temperature for 10 min, and then detected by a microplate reader for fluorescence value of Luc. The used CellTiter-Glo Luminescent Cell Viability Assay kit was purchased from Promega. The same detections for the cells from 12-well plates were made according to the above steps on the 9th, 10th, 11th, 12th, and 13th days of culture. Cell proliferation curves were drawn based on the detected fluorescence values.

Figure 24:
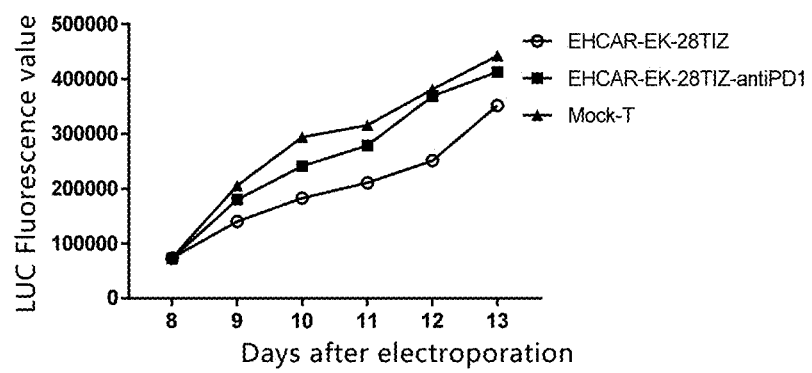
FIG. 24: Comparison of the proliferation rate of EHCAR-EK-28TIZ and EHCAR-EK-28TIZ-antiPD1 T cells.

The results are shown in FIG. 24. The proliferation rate of EHCAR-EK-28TIZ-antiPD1 T cells is significantly higher than that of EHCAR-EK-28TIZ T cells, indicating that the expression of CD40 antibody can promote the proliferation of CAR-T cells.

FIG. 29: Cell phenotype analysis of EHCAR-EK-28TIZ and EHCAR-EK-28TIZ-antiPD1 T cells The EHCAR-EK-28TIZ T cells and EHCAR-EK-28TIZ-antiPD1 T cells obtained in Example 2 were added into six 1.5 ml EP tubes with $1\times10^6$ cells/tube respectively, washed twice with PBS, centrifuged at 1200 rpm for 5 min, and the supernatant was discarded. Two of the tubes were added with the flow cytometry antibodies anti-CD107α-PE and anti-CD69-PE to detect activated T cell phenotype; one of the tubes was added with the flow cytometry antibodies anti-CD45RO-PECy5+ anti-CD197-FITC+ anti-CD62L-PE to detect memory T cell phenotype, one of the tubes was added with the flow cytometry antibody anti-PD1-PE to detect the inhibitory T cell phenotype, and the other 2 tubes were added with the isotype control flow cytometry antibodies IgG1-PE and IgG1-PE+IgG2a-PECy5+IgG2a-PE; 2 μl for each antibody (Jackson ImmunoResearch). The precipitate was flicked to make it mix evenly. After incubation at room temperature in the dark for 30 min, the cells were washed with PBS once, centrifuged at 1200 rpm for 5 min, the supernatant was discarded and 400 μl of normal saline was added, and the cells were transferred to a flow tube, and analyzed on the machine.

Figure 25A:
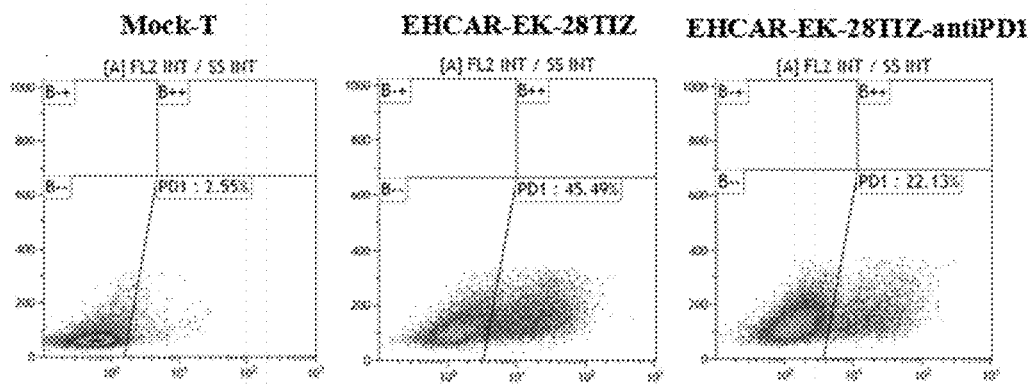
FIG. 25A-25D: Phenotype analysis of EHCAR-EK-28TIZ and EHCAR-EK-28TIZ-antiPD1 T cells; 25A represents the aging phenotype PD1, 25B and 25C represent the activated phenotype CD69 and CD107α respectively. 25D represents the memory phenotype.
Figure 25B:
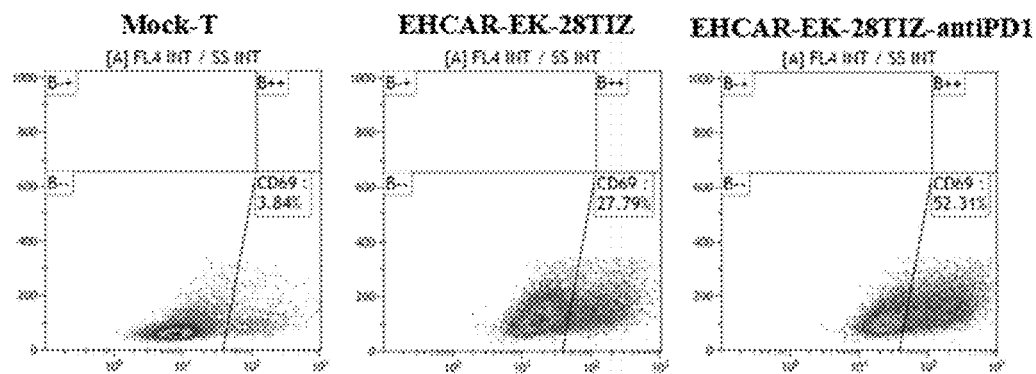
Figure 25C:
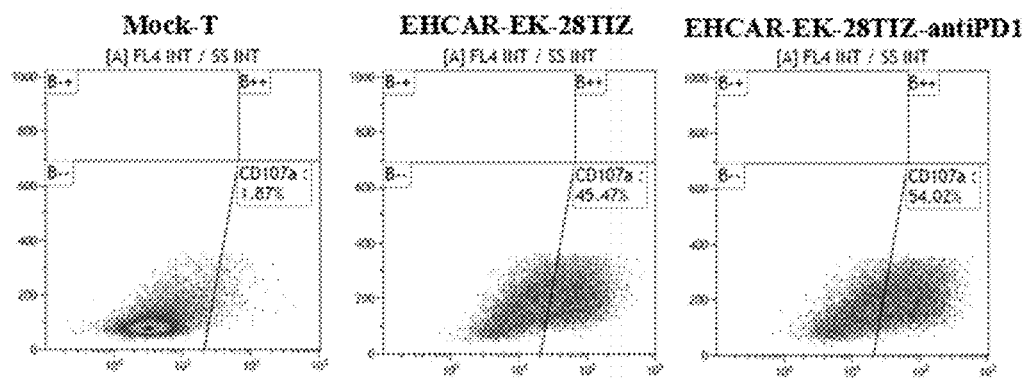
Figure 25D:
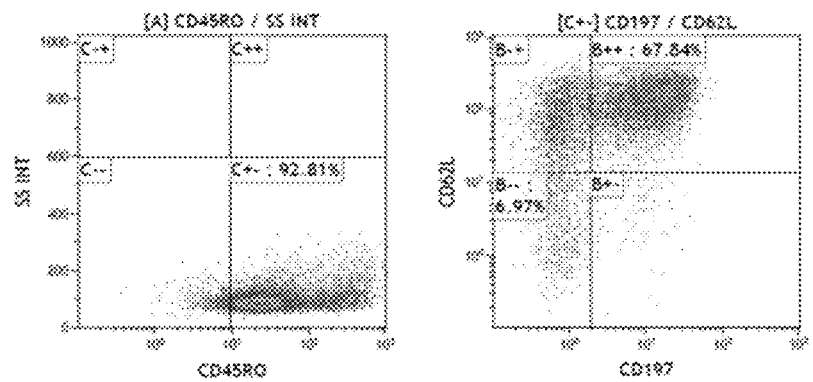
Figure 25D:
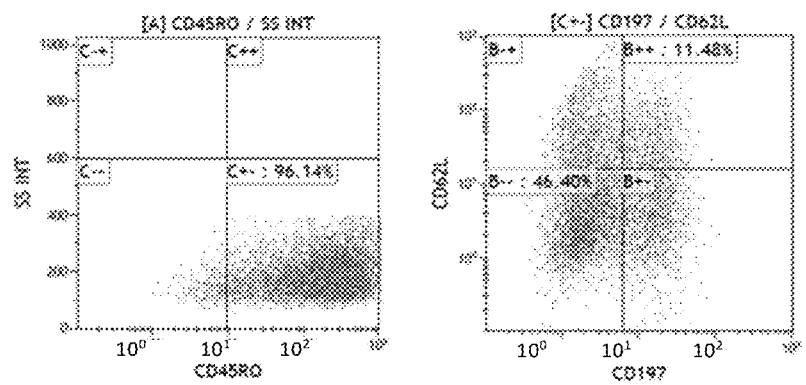
Figure 25D:
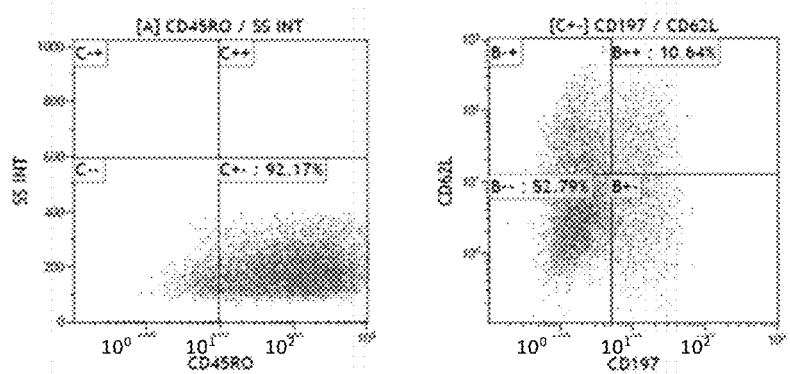

The results show that the expression of the aging phenotype PD1 of EHCAR-EK-28TIZ-antiPD1 T cells by flow cytometry is significantly lower than that of EHCAR-EK-28TIZ (FIG. 25A); the expressions of the activated phenotypes CD69 and CD107α of EHCAR-EK-28TIZ-antiPD1 T cells are higher than those of EHCAR-EK-28TIZ cells (FIGS. 25B and 25C); meanwhile, CD621, (L-selectin) is a marker of central memory T cells, and CD197 is a marker of effector memory T cells, and the proportion of effector T cells in EHCAR-EK-28TIZ-antiPD1 T cells is significantly higher than those of EHCAR-EK-28TIZ cells and Mock-T cells (FIG. 25D). These results indicate that the expression of PD1 antibody can inhibit the depletion of CAR-T cells, promote the activation of CAR-T cells, and enhance their immune killing effect.

Figure 26:
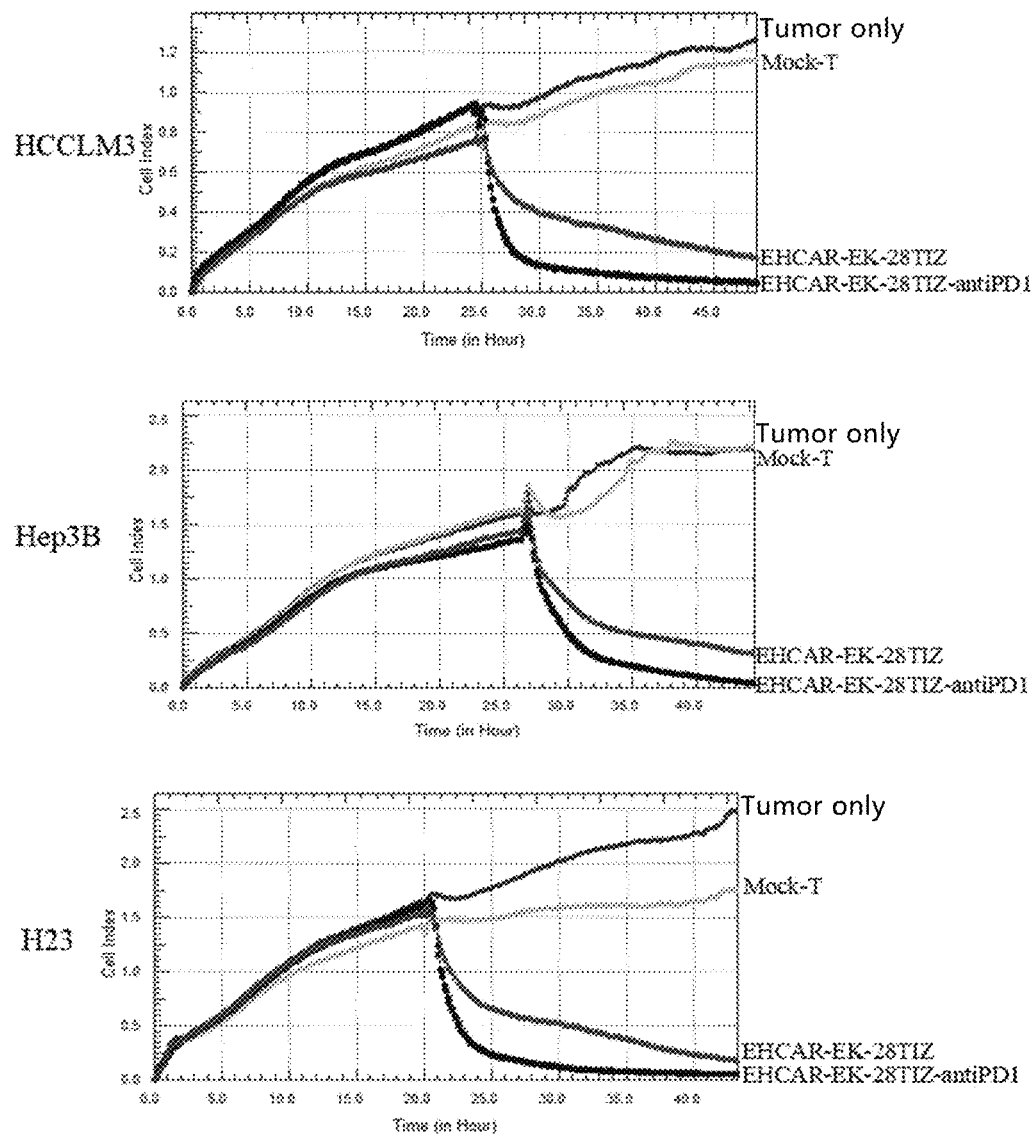
FIG. 26: Comparison of the killing by EHCAR-EK-28TIZ and EHCAR-EK-28TIZ-antiPD1 T cells, including human liver cancer cells HCCLM3, human liver cancer cells Hep3B and human non-small cell lung cancer H23.
Figure 30:
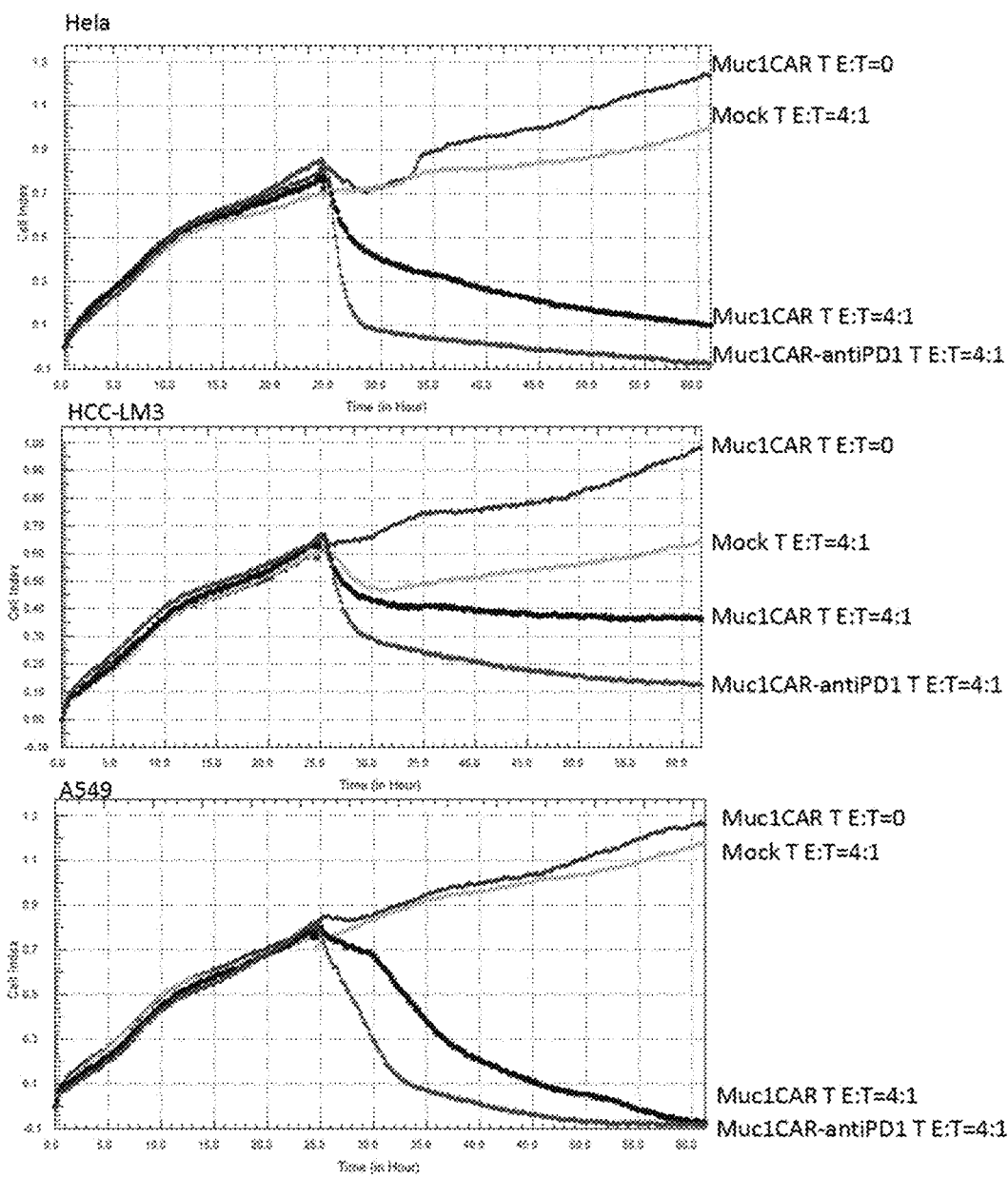
FIG. 30: Detection of the killing effect of Muc1 CAR-anti PD1 pluripotent T cells.

FIG. 30: Comparison of the killing effect of EHCAR-EK-28TIZ and EHCAR-EK-28TIZ-antiPD1 T cells Target cells and effector cells that match MHC class I were selected, and Real-time label-free cell analysis system (RTCA, ACEA) was used to detect the in vitro killing effect of the EHCAR-EK-28TIZ T cells and EHCAR-EK-28TIZ-antiPD1 T cells obtained in Example 2. The steps are as follows:
(1) Zero adjustment: Add 50 μl DMEM or 1640 culture medium to each well, put it into the instrument, select step 1, and adjust zero;
(2) Target cell plating: Plate human liver cancer cell HCCLM3, human liver cancer cell Hep3B and human non-small cell lung cancer H23 (American Type Culture Collection ATCC) at $10^4$ cells/50 μl per well on a plate containing detection electrodes, let rest for a few minutes to stabilize the cells, then put them into the instrument, start step 2 to culture the cells;
(3) Adding effector cells: After 24 h culture of target cells, pause step 2 and add effector cells at 50 μl per well, with the effect target ratio of 4:1 and Mock T cells transferred with empty pNB328 as the control, start step 3 to continue co-cultivation for 24 h, then generate the cell proliferation curve;

The results are shown in FIG. 26. The killing effect of EHCAR-EK-28TIZ-antiPD1 T cells that self-express PD1 antibody on a variety of tumor cells is significantly greater than those of EHCAR-EK-28TIZ T cells and control T cells.

Example 31: Comparison of Cytokine Release Between EHCAR-EK-28TIZ. T Cells and EHCAR-EK-28TIZ-antiPD1 T Cells Under Specific Stimulation of EGFR Antigen 96-well plates were coated overnight with 5 ug/ml EGFR antigen at 4° C., washed 3 times with PBS, added with 1×10$^5$ (100 ul of volume) EHCAR-EK-28TIZ T cells and EHCAR-EK-28TIZ-antiPD1 T cells prepared according to Example 2 and control Mock T cells (transferred with empty pNB328). Supernatant was collected after 24 hours of culture. The cytokine secretion of these three T cells after being stimulated by EGFR antigen was detected.

Figure 27:
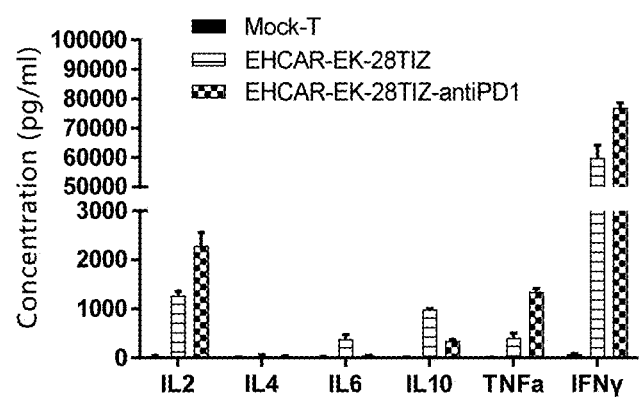
FIG. 27: Changes of secretions of cytokines IL-2, IL-4, IL-6, IL-10, TNF-α and IFN-γ of EHCAR-EK-28TIZ and EHCAR-EK-28TIZ-antiPD1 T cells upon the stimulation of EGFR antigen.

The results are shown in FIG. 27. The secretions of IL-2 and IFNγ from EHCAR-EK-28TIZ-antiPD1 T cells are significantly higher than those from EHCAR-EK-28TIZ T cells and Mock-T, indicating that self-expressing PD1 antibodies can promote the secretion of cytokines by CAR-T cells.

Example 32: Anti-Tumor Effect of EHCAR-EK-28TIZ T Cells, EHCAR-EK-28TIZ-antiPD1-Wt T Cells and EHCAR-EK-28TIZ-antiPD1 T Cells In Vivo Twenty NSG mice of 4-6 weeks were divided into 5 groups on average, with 4 mice of each group inoculated with liver cancer cell line HCCLM3-LUC for 1×10$^7$ per mouse. 10 days after tumor being formed, each group was injected via tail vein with PBS (100 ul PBS), Mock-T cells, EHCAR-EK-28TIZ T cells, EHCAR-EK-28TIZ-antiPD1-wt T cells and EHCAR-EK-28TIZ-antiPD1 T cells (1×10$^7$/100 ul of each), respectively. The changes of the tumor fluorescence in mice were observed and recorded.

The results show that PBS, Mock-T, EHCAR-EK-28TIZ-antiPD1-wt T cells have no therapeutic effect on the tumor model, EHCAR-EK-28TIZ T cells and EHCAR-EK-28TIZ-antiPD1 T cells have good anti-tumor effects, and EHCAR-EK-28TIZ-antiPD1 T cells are significantly better. The details are shown in FIG. 28.

Example 33: Detection of Genomic Expression Level of Muc1CAR in T Cell Genome after PBMCs Cells from Different Patients being Modified by Muc1 CAR Gene and PD-1 Antibody Gene Extract the genomic DNA of the Mock T cells, Muc1 CAR T cells and Muc1CAR-antiPD1 T cells obtained in Example 2 (method by kit) using the experimental procedure based on the attached instructions, determine DNA concentration of Mock T cells, Muc1CAR T cells and Muc1CAR-antiPD1 T cells, and detect the expression level of Muc1CAR genome by real-time fluorescence quantitative PCR method, with the reaction procedure of 50° C., 2 min→95° C., 10 min→95° C., 15 s→60° C., lmin, for 40 cycle. Generate the CT value of the Muc1CAR in genome and the CT value of Actin, and then calculate the absolute copy number content according to the corresponding formula.

It is found that through the PB transposase system, the Muc1CAR genome has been integrated into the T cell genome, as shown in Table 8 below:

TABLE 8

| Donor | Type of T cell | Copy Number (within a single cell) |
|---|---|---|
| Patient 1 | Mock T | 0.00 |
| | Muc1CAR T | 19.04 |
| | Muc1CAR-antiPD1 T | 22.82 |
| Patient 2 | Mock T | 0.00 |
| | Muc1CAR T | 10.14 |
| | Muc1CAR-antiPD1 T | 12.58 |
| Patient 3 | Mock T | 0.00 |
| | Muc1CAR T | 20.46 |
| | Muc1CAR-antiPD1 T | 22.33 |

Example 34: Detection of Differences of Activation Phenotype and Cytokine Secretion Between Mock T Cells, Muc1 CAR T Cells and Muc1CAR-antiPD1 T Cell by Flow Cytometry 1. The suspended Mock T cells, Muc1CAR T cells and Muc1CAR-antiPD1 T cells transferred with pNB328-Muc1CAR and pS328-m279V vector were washed twice with PBS, centrifuged at 1200 rpm for 5 min, and added with 2 ul of the isotype control antibody IgG1-PE, the fluorescent flow cytometry antibodies anti-CD25-PE, anti-LAG3-PE, anti-PD1-PE; isotype control antibody IgG1-PC5, the fluorescent flow cytometry antibody anti-CD107-PC5; isotype control antibody IgG1 FITC, fluorescent flow cytometry antibody anti-CD62L-FITC; isotype control antibody IgG1-PC5, fluorescent flow cytometry antibody anti-CD45RO-PC5; isotype control antibody IgG1-PE, fluorescent flow cytometry antibody anti-CCR7-PE, respectively. The precipitate was flicked to make it mix evenly, the cells were incubated at room temperature in the dark for 30 min, washed with PBS once, added with 400 μl PBS and transferred to a flow tube, then analyzed on the machine.

Figure 29A:
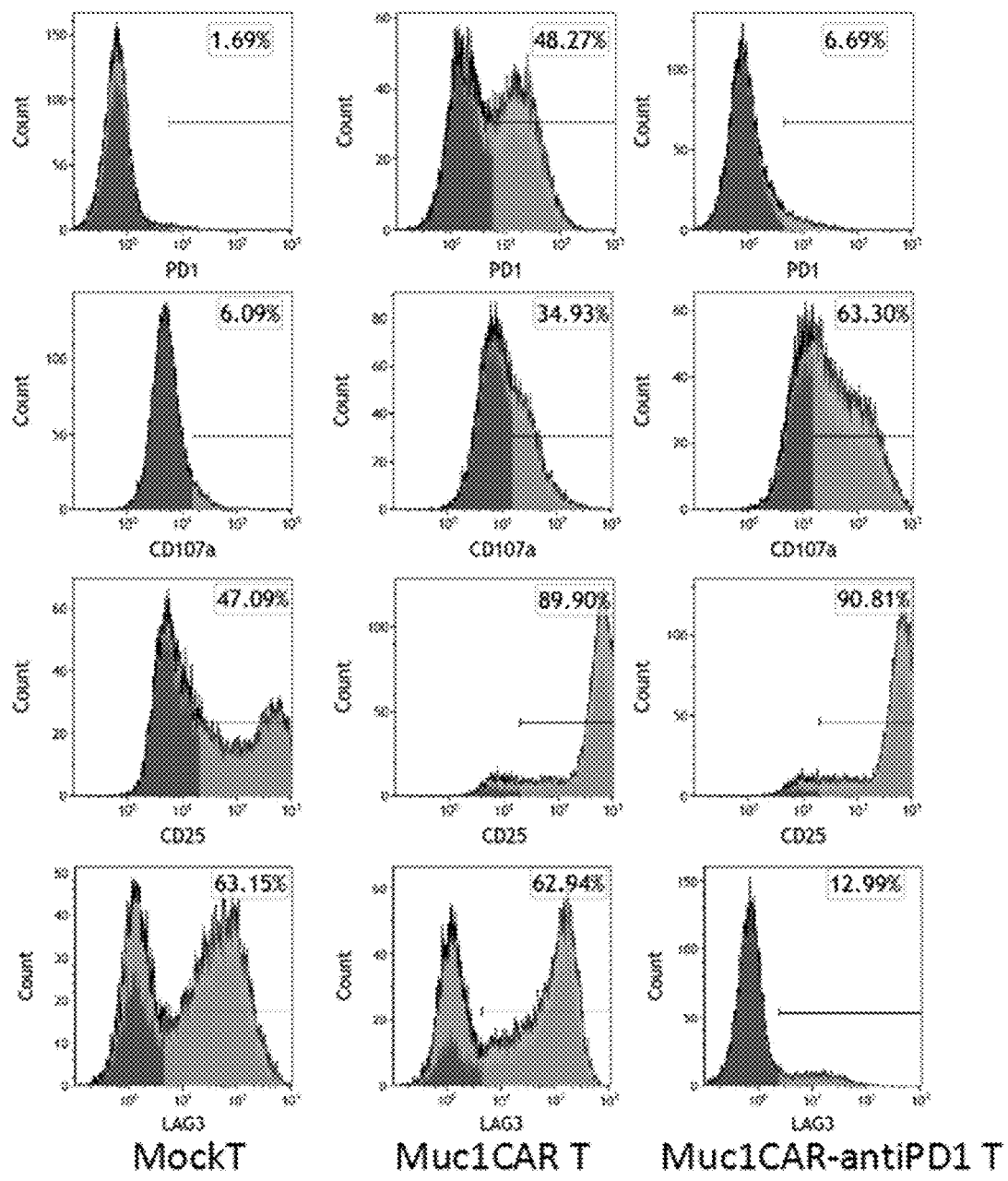
FIG. 29A-29D: Muc1CAR-anti PD1 pluripotent T cells can enhance the killing activity of T cells in vitro. 29A: Flow cytometry detection of marker CD107α that indirectly reflects the T cell killing activity, activation marker CD25 and depletion marker LAG3, 29B: flow cytometry detection of marker proteins CD45RO, CD62L and CCR7 reflecting the T cell memory phenotype. 29C: Flow cytometry detection of the ratio of CD3/CD4/CD8 of T cells. 29D: Detection, through multi-factor detection kit, of the changes in IL-2, IL-4, IL-6, IL-10, TNF-α and IFN-γ cytokines of Muc1CAR-anti PD1 multipotent T cells, Muc1 CAR-T cells and Mock T cells upon stimulation by Muc1 antigen.
Figure 29B:
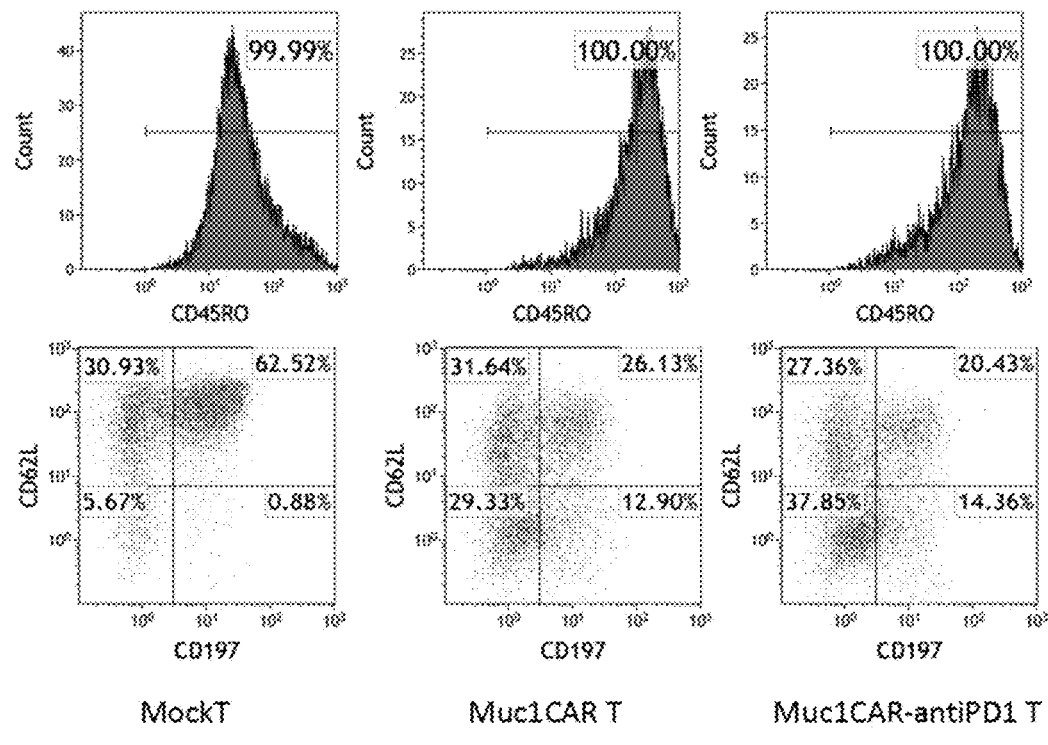
Figure 29C:
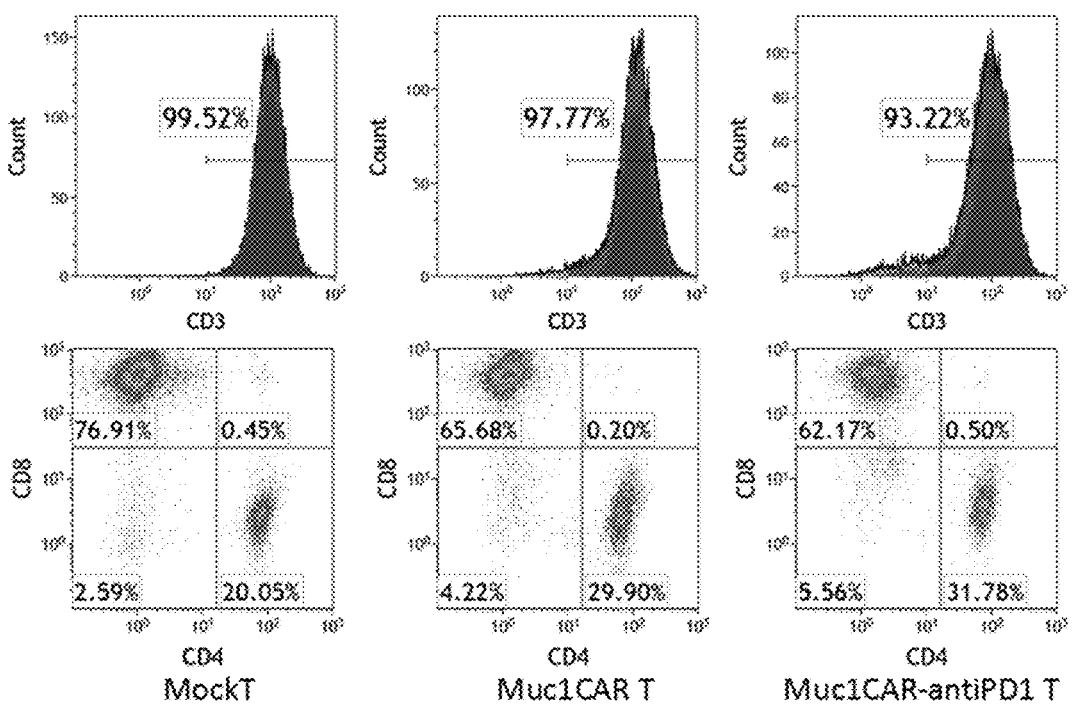

The results show that the PD-1 single-chain antibody secreted by Muc1CAR-antiPD1 T cells can block the PD-1 protein on the surface of T cells well. Muc1CAR T cells and Muc1CAR-antiPD1 T cells have obvious killing activity in vitro and can also promote the formation of memory T, while activation marker CD25 is significantly higher than Mock T cells and depletion marker LAG3 of Muc1CAR-antiPD1 T cells is significantly lower than Mock T cells and Muc1 CAR T cells. The details are shown in FIGS. 29A and 29B.

2. 1×10$^6$ Muc1CAR T cells and Muc1CAR-antiPD1 T cells transferred with pNB328-Muc1CAR and pS328-m279V vector obtained in Example 2 were added to 1.5 ml EP tubes respectively, washed twice with PBS, centrifuged at 1200 rpm for 5 min, added with 2 ul of α-CD3CD4CD8 antibody, incubated at room temperature in the dark for 30 min, washed once with PBS, added with 400 ul PBS and transferred to the flow tube, and assayed on the machine.

It is found that no big difference is shown in the percentages of CD3$^+$CD4$^+$ and CD3+CD8+ cells in Muc1 CAR T cells, Muc1CAR-antiPD1 T cells and Mock T cells, as shown in 29C.

3. 24-well plates were coated overnight with 5 ug/ml Muc1 antigen at 4° C., washed 3 times with PBS, added with 3×10$^5$ of Mock T cells, Muc1 CAR T cells and Muc1CAR-antiPD1 T cells transferred with pNB328-Muc1CAR and pS328-m279V vector prepared according to Example 2. Supernatant was collected after 24 hours of culture.

BD™CBA Human Th1/Th2 Cytokine Kit II was used to detect the secretion of cytokines of Muc1CAR T cells and Muc1CAR-antiPD1 T cells after stimulated by Muc1 antigen:
(1) Mix human IL-2, IL-4, IL-6, IL-10, TNF-α, IFN-γ capture magnetic beads by vortex, add 50 ul of mixed beads to each tube;
(2) Add 50 ul of human Th1/Th2 cytokine standard (diluted to 5000 pg/ml, 2500 pg/ml, 1250 pg/ml, 625 pg/ml, 312.5 pg/ml, 156 pg/ml, 80 pg/ml, 40 pg/ml, 20 pg/ml, or 0 pg/ml) and 50 ul of the sample to be tested (diluted by 2-fold with the diluents);
(3) Add 50 ul of human Th1/Th2-II-PE detection antibody to each tube;
(4) Incubate at room temperature in the dark for 3 h;
(5) Add 1 ml of washing buffer to each tube, centrifuge at 200 g for 5 min, and discard the supernatant;
(6) Add 300 ul of washing buffer to each tube to resuspend the cells, and transfer the cells to a flow cytometry tube to detect the fluorescence value by a flow cytometer.

Figure 29D:
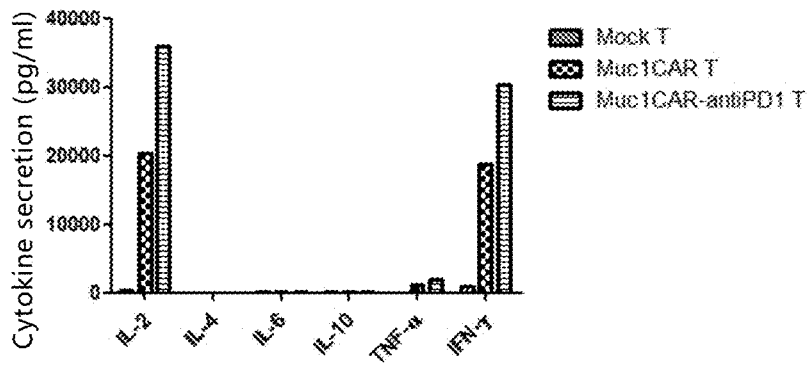

The results show that the IL-2, TNF-α and IFN-γ secretion of Muc1CAR T cells and Muc1CAR-antiPD1 T cells are greatly improved as compared to Mock T cells. The IL-4, IL-6 and IL-10 secretion of the three cells are not substantially different, as shown in FIG. 29D.

Example 35: Killing Assay of Mock T Cells, Muc1 CAR T Cells, and Muc1CAR-antiPD1 T Cells on the Cultured Tumor Cells In Vitro Target cells and effector cells that match MHC class I were selected, and Real-time label-free cell analysis system (RTCA) was used to detect the killing effect of the cells in vitro. The steps are as follows:
(1) Zero adjustment: Add 50 μl DMEM or 1640 culture medium to each well, put it into the instrument, select step 1, and adjust zero;
(2) Target cell plating: Plate cervical cancer cell Hela, liver cancer cell HCC-LM3 and lung cancer cell A549 (American Type Culture Collection ATCC) at $10^4$ cells/50 μl per well on a plate containing detection electrodes, let rest for a few minutes to stabilize the cells, then put them into the instrument, start step 2 to culture the cells;
(3) Adding effector cells: After 24 h culture of target cells, pause step 2 and add effector cells (the Mock T cells, Muc1CAR T cells and Muc1CAR-antiPD1 T cells transferred with pNB328-Muc1CAR and pS328-m279V vector prepared according to Example 2) at 50 μl per well, with the effect target ratio of 4:1 and Mock T cells without a transferred vector as the control, start step 3 to continue co-cultivation for 24 h, then generate the cell proliferation curve.

The results show that Muc1CAR T cells expressing PD-1 antibody are superior to Muc1CAR T cells in killing all three tumor cells. The details are shown in FIG. 30.

Example 36: In Vivo Function Study of Muc1CAR T Cells that Express PD-1 Antibody Step 1: 15 of 4-6 weeks old NSG completely immunodeficient mice, with an average weight of 22-27 g, were provided by Beijing Vitalstar Biotech Co., Ltd., and raised by a SPF animal laboratory.

Step 2: Adhered human cervical cancer cell Hela in logarithmic growth phase cultured in vitro were digested with 0.25% trypsin, centrifuged, collected and resuspended in PBS solution. The cells were centrifuged at 3000 g for 2 minutes at room temperature, the supernatant was discarded and the cells were resuspended in PBS solution, centrifuged and collected, and the concentration of the cell suspension was adjusted to $5 \times 10^7$ cells/ml.

Step 3: The Hela-luc cells were inoculated subcutaneously in the dorsum of the right rib of the mouse at 0.1 ml/mouse. About 10 days after the inoculation, the size of the tumor was observed by an in vivo imager, and the NSG immunodeficient mice were randomly divided into 4 groups (five mice each). Each group was injected through the tail vein with PBS (100 ul), Mock T cells, Muc1CAR T cells, Muc1CAR-antiPD1-wt T cells transferred with pNB328-Muc1CAR and pS328-m279V-wt, and Muc1CAR-antiPD1 T cells transferred with pNB328-Muc1CAR and pS328-m279V, prepared according to Example 2 ($1 \times 10^7$ cells/mouse).

Step 4: The living conditions of mice were observed every day and the change of the tumor in each mouse was observed by in vivo imager every 10 days.

Figure 31:
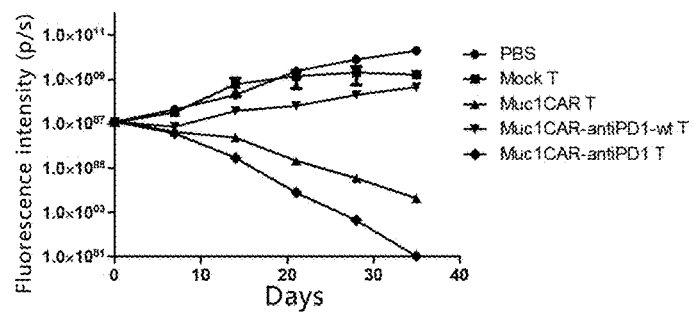
FIG. 31: In vivo function study of Muc1 CAR T cells that expresses PD-1 antibody.

The results are shown in FIG. 31.

Figure 37:
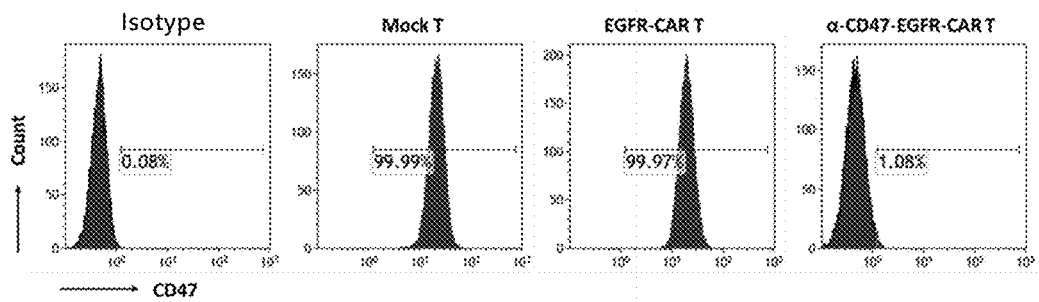
FIG. 37: Flow cytometry detection of CD47 expression in Mock, Meso3CAR and αCD47-Meso3CAR T cells.

FIG. 37: Detection of CD47 expression in Mock T cells, EGFR-CART cells, and αCD47-EGFR-CAR T cells.

The Mock T cells, EGFR-CAR T cells and αCD47-EGFR-CAR T cells prepared according to Example 2 were collected, and the expression of CD47 was detected using the flow cytometry antibody (BD) murine anti-human CD47-FITC by the flow cytometry as in Example 3.

Figure 32:
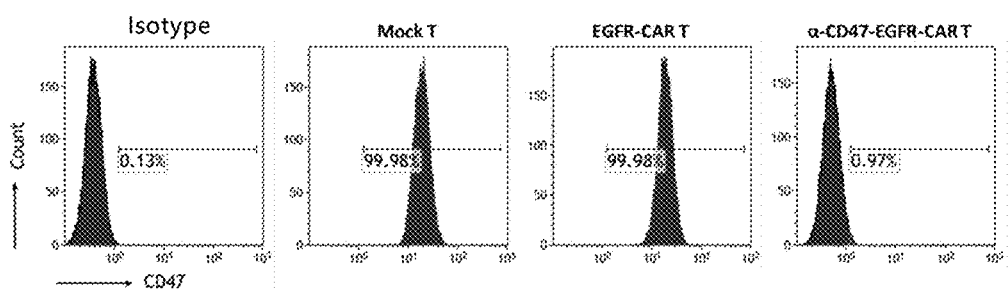
FIG. 32: Flow cytometry detection of CD47 expression in Mock T cells, EGFR-CAR T cells, and αCD47-EGFR-CAR T cells.

The results are shown in FIG. 32. The CD47 antibody secreted by αCD47-EGFR-CAR T cells can block the self-expressed CD47 of the cells.

Example 38: Killing Effect of Mock T Cells, EGFR-CAR T Cells and αCD47-EGFR-CAR T Cells on Tumor Cells Three types of EGFR-positive cells were selected as target cells: lung cancer cell line H23, ovarian cancer cell line SKOV3, and pancreatic cancer cell line ASPC-1. Real-time label-free cell analysis system (RTCA, ACEA) was used to detect the in vitro killing effect of the Mock T cells, EGFR-CAR T cells and αCD47-EGFR-CAR T cells obtained in Example 2. The steps are as follows:
(1) Zero adjustment: Add 50 μl DMEM or 1640 culture medium to each well, put it into the instrument, select step 1, and adjust zero;
(2) Target cell plating: Plate lung cancer cell line H23, ovarian cancer cell line SKOV3, pancreatic cancer cell line ASPC-1 (American Type Culture Collection ATCC) at $10^4$ cells/50 μl per well on a plate containing detection electrodes, let rest for a few minutes to stabilize the cells, then put them into the instrument, start step 2 to culture the cells;
(3) Adding effector cells: After 24 h culture of target cells, pause step 2 and add effector cells at 50 μl per well, with the effect target ratio of 4:1 and Mock T cells transferred with empty pNB328 as the control, start step 3 to continue co-cultivation for 24 h, then generate the cell proliferation curve.

Figure 33:
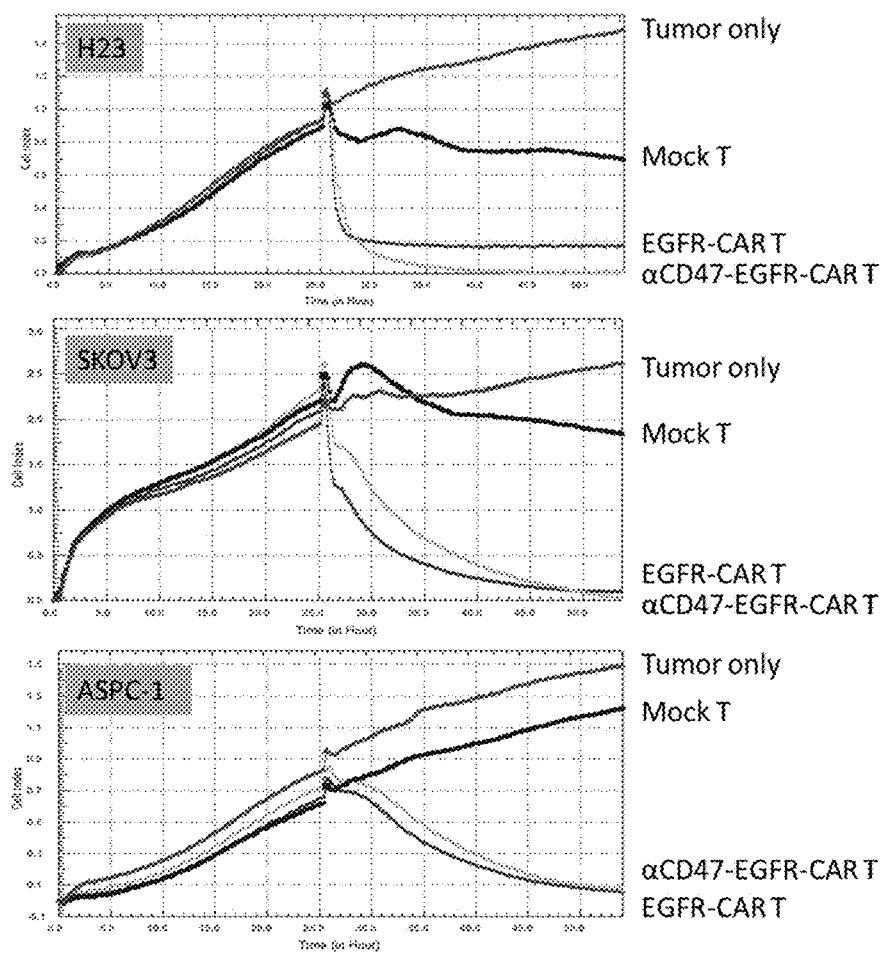
FIG. 33: Killing of different tumor cells by αCD47-EGFR-CAR T cells.

The results are shown in FIG. 33. The in vitro killing effects of EGFR-CAR T cells and αCD47-EGFR-CAR T cells are significantly higher than that of Mock T cells, and the self-expression of CD47 antibody does not affect the killing effect of CAR-T cells.

Example 39: αCD47-EGFR-CAR T Cell Culture Supernatant can Block CD47 on the Surface of Tumor Cells The culture supernatants of αCD47-EGFR-CAR T cells obtained in Example 2 were co-cultured with lung cancer cell line H23, ovarian cancer cell line SKOV3, and pancreatic cancer cell line ASPC-1, respectively. After 24 hours, the tumor cells were collected to detect CD47 expression, compared with those without co-culture with αCD47-EGFR-CAR T cell supernatant.

Flow cytometry is the same as in Example 3.

Figure 34:
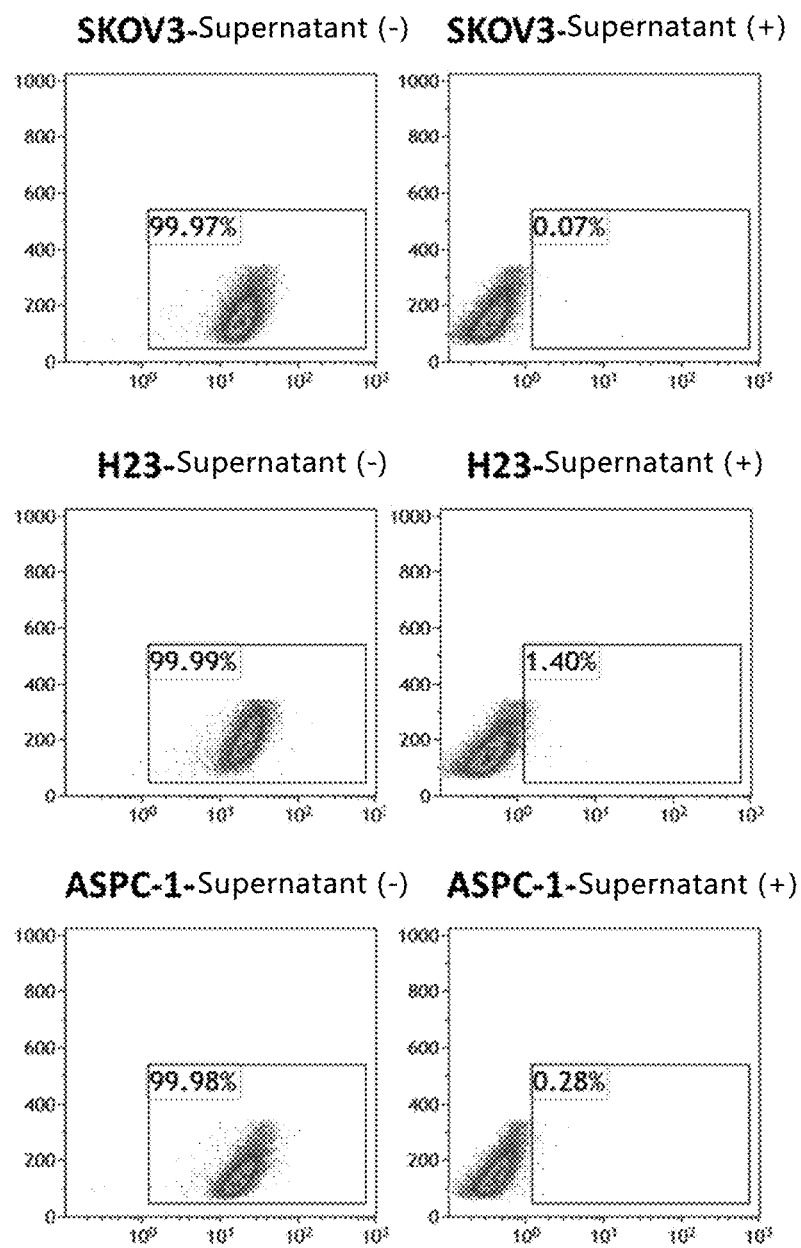
FIG. 34: αCD47-EGFR-CAR T cell supernatant was co-cultured with different tumor cells to block CD47 on the surface of the tumor cells.

The results are shown in FIG. 34. The CD47 antibody in the supernatant of the αCD47-EGFR-CAR T cells can block the CD47 on the surface of the tumor cells.

Example 40: Blocking CD47 on the Surface of the Tumor Cells can Enhance the Phagocytosis of Macrophages to the Tumor Cells 1. Isolation and culture of macrophages: Ficoll density gradient centrifugation method was used to isolate peripheral blood mononuclear cells (PBMC), which were adherently cultured at 37° C. in a 5% $CO_2$ incubator for 4 hours. The non-adherent cells were washed away by pre-warmed medium, and AIM-V medium and rhGM-CSF were added (final concentration of 1000 U/ml). After two and a half days, the medium was exchanged and the cells were cultured for 7 days to obtain adherent cells, which are macrophages.

2. Phagocytosis of macrophages to tumor cells: the tumor cells were stained to blue with Hoechst dye, and the macrophages were stained to red with CM-Dil, by the staining methods according to the manufacturer's instructions. The two stained cells were mixed and divided to two parts: one was added with the culture supernatant of EGFR-CAR T cells prepared according to Example 2 as a control, and the other was added with the culture supernatant of αCD47-EGFR-CAR T cells prepared according to Example 2. Phagocytosis was observed using a confocal microscope, and the phagocytosis efficiency was counted.

Figure 35:
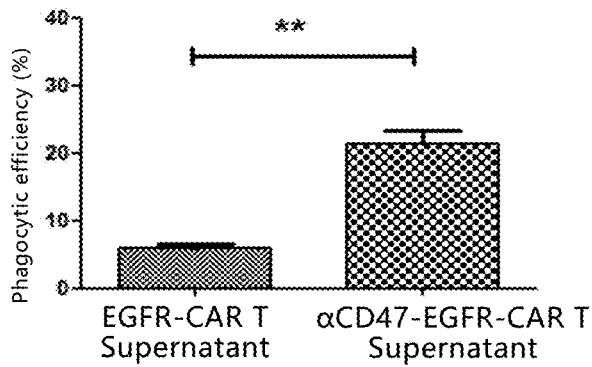
FIG. 35: Blocking CD47 on the surface of the tumor cells can enhance the phagocytosis of macrophages to the tumor cells.

The results are shown in FIG. 35. The phagocytosis by macrophage for the αCD47-EGFR-CAR T cells culture supernatant group is significantly higher than that of the control group.

Example 41: Anti-Tumor Effect of αCD47-EGFR-CAR T Cells In Vivo

Figure 36:
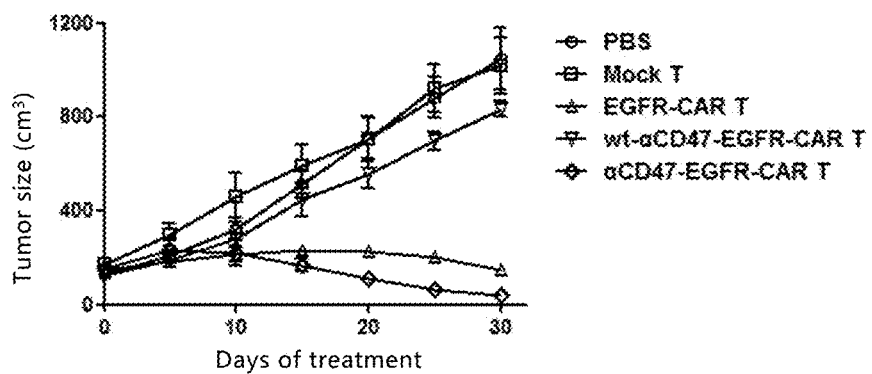
FIG. 36: Anti-tumor effect of αCD47-EGFR-CAR T cell in mice in vivo.

Twenty NSG mice of 4-6 weeks were divided into 5 groups on average, with 4 mice of each group inoculated with lung cancer cell line H23 for $1\times10^7$ per mouse. 10 days after tumor being formed, each group was injected via tail vein with PBS (100 ul PBS), Mock T cells, EGFR-CAR T cells, wt-αCD47-EGFR-CAR T cells and αCD47-EGFR-CAR T cells obtained in Example 2 ($1\times10^7$/100 ul of each), respectively. The tumor volume was observed and recorded. The results show that PBS, Mock T cells, wt-αCD47-EGFR-CAR T cells have no therapeutic effect on tumor models, EGFR-CAR T cells and αCD47-EGFR-CAR T cells have good anti-tumor effects, and αCD47-EGFR-CAR T cells are more effective. The details are shown in FIG. 36.

Example 42: Detection of CD47 Expression in Mock, Meso3CAR and αCD47-Meso3CAR T Cells The Mock T cells, Meso3CAR T cells and αCD47-Meso3CAR T cells prepared according to Example 2 were collected, and the expression of PD1 was detected using the flow cytometry antibody FITC-murine anti-human CD47 (BD) by the flow cytometry method as in Example 3.

The results are shown in FIG. 37. The CD47 antibody secreted by αCD47-Meso3CAR T cells can block the expression of CD47 on the surface of the cells.

Example 43: Killing Effect of Mock, Meso3CAR and αCD47-Meso3CAR T Cells on Tumor Cells Three types of EGFR-positive cells were selected as target cells: gastric cancer cell line Hgc27, ovarian cancer cell line SKOV3, and pancreatic cancer cell line ASPC-1. Real-time label-free cell analysis system (RTCA, ACEA) was used to detect the in vitro killing effect of the Mock T cells, Meso3CAR T cells and αCD47-Meso3CAR T cells obtained in Example 2. The steps are as follows:

(1) Zero adjustment: Add 50 µl DMEM or 1640 culture medium to each well, put it into the instrument, select step 1, and adjust zero;

(2) Target cell plating: Plate gastric cancer cell line Hgc27, ovarian cancer cell line SKOV3, pancreatic cancer cell line ASPC-1 (American Type Culture Collection ATCC) at $10^4$ cells/50 µl per well on a plate containing detection electrodes, let rest for a few minutes to stabilize the cells, then put them into the instrument, start step 2 to culture the cells;

(3) Adding effector cells: After 24 h culture of target cells, pause step 2 and add effector cells at 50 µl per well, with the effect target ratio of 4:1 and Mock T cells transferred with empty pNB328 as the control, start step 3 to continue co-cultivation for 24 h, then generate the cell proliferation curve.

Figure 38:
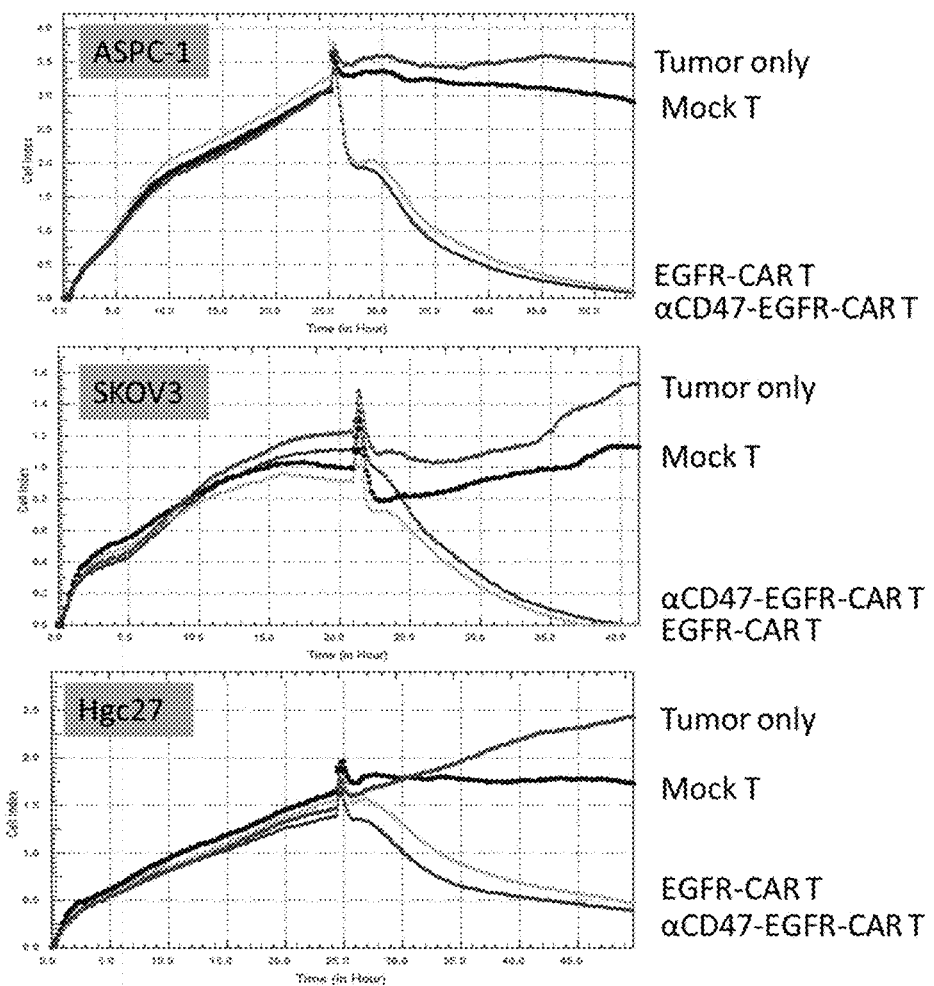
FIG. 38: Killing of tumor cell line by αCD47-Meso3CAR T cells.

The results are shown in FIG. 38. The in vitro killing effects of Meso3CAR T cells and αCD47-Meso3CAR T cells are significantly higher than that of Mock T cells, and the expression of CD47 antibody does not affect the killing effect of CAR-T cells.

Example 44: αCD47-Meso3CAR T Cell Culture Supernatant can Block CD47 on the Surface of Tumor Cells The culture supernatants of αCD47-Meso3CAR T cells obtained in Example 2 were co-cultured with gastric cancer cell line Hgc27, ovarian cancer cell line SKOV3, and pancreatic cancer cell line ASPC-1, respectively. After 24 hours, the tumor cells were collected to detect CD47 expression, compared with those without co-culture with αCD47-Meso3CAR T cell supernatant. The flow cytometry method is the same as above.

Figure 39:
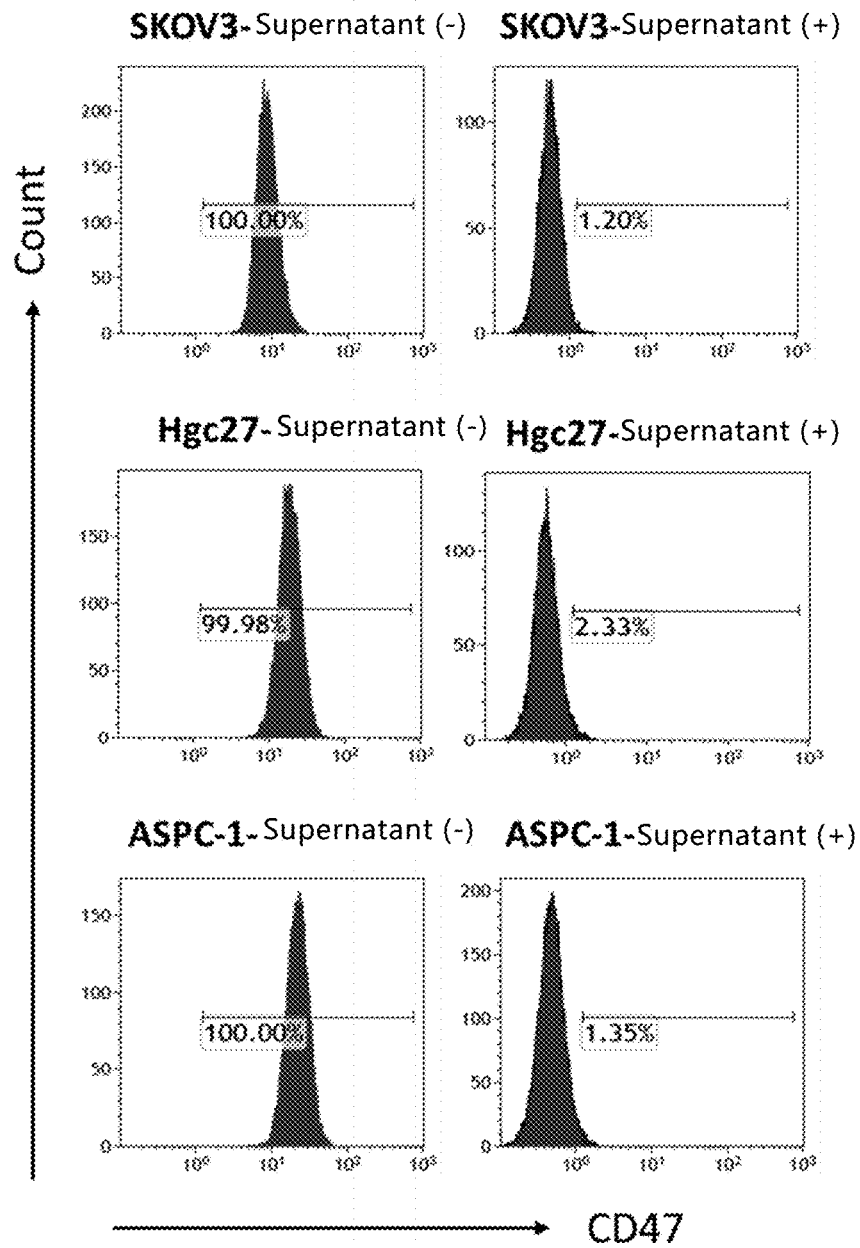
FIG. 39: αCD47-Meso3CAR T cell supernatant was co-cultured with tumor cells to block CD47 on the surface of the tumor cells.

The results are shown in FIG. 39. The CD47 antibody in the supernatant of the αCD47-Meso3CAR T cells can block the expression of CD47 by the tumor cells.

Example 45: Blocking CD47 on the Surface of the Tumor Cells can Enhance the Phagocytosis of Macrophages to the Tumor Cells 1. Isolation and culture of macrophages: Ficoll density gradient centrifugation method was used to isolate peripheral blood mononuclear cells (PBMC), which were adherently cultured at 37° C. in a 5% $CO_2$ incubator for 4 hours. The non-adherent cells were washed away by pre-warmed medium, and AIM-V medium and rhGM-CSF were added (final concentration of 1000 U/ml). After two and a half days, the medium was exchanged and the cells were cultured for 7 days to obtain adherent cells, which are macrophages.

2. Phagocytosis of macrophage to tumor cells: the tumor cells were stained to blue with Hoechst dye, and the macrophages were stained to red with CM-Dil, by the staining methods according to the manufacturer's instructions. The two stained cells were mixed and divided to two parts: one was added with the culture supernatant of Meso3CAR T cells prepared according to Example 2 as a control, and the other was added with the culture supernatant of αCD47-Meso3CAR T cells prepared according to Example 2. Phagocytosis was observed using a confocal microscope, and the phagocytosis efficiency was counted.

Figure 40:
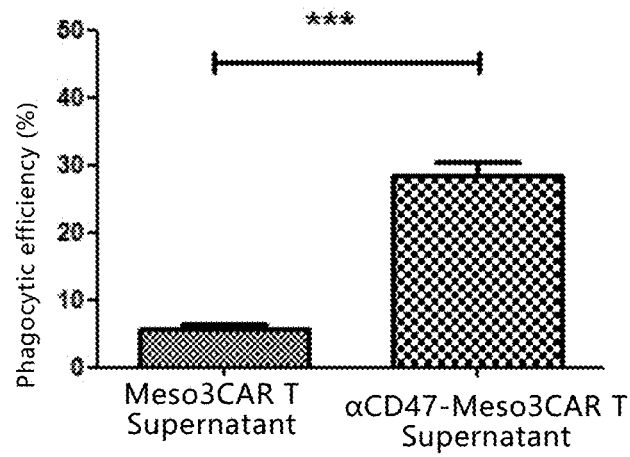
FIG. 40: Blocking CD47 on the surface of the tumor cells can enhance the phagocytosis of macrophages to the tumor cells.

The results show that the phagocytosis by macrophage for the αCD47-Meso3CAR T cells culture supernatant group is significantly higher than that of the control group. The statistical results are shown in FIG. 40.

Example 46: Anti-Tumor Effect of αCD47-Meso3CAR T Cells In Vivo

Twenty NSG mice of 4-6 weeks were divided into 5 groups on average, with 4 mice of each group inoculated with lung cancer cell line H23 for $1\times10^7$ per mouse. 10 days after tumor being formed, each group was injected via tail vein with PBS (100 ul PBS), Mock T cells, Meso3CAR T cells, wt-αCD47-Meso3CAR T cells and αCD47-Meso3CAR T cells obtained according to Example 2 ($1\times10^7$/mouse), respectively. The tumor volume was observed and recorded. The results show that PBS, Mock T cells, wt-αCD47-Meso3CAR T cells have no therapeutic effect on the tumor models, while αCD47-Meso3CAR T cells have good anti-tumor effects.

Figure 41:
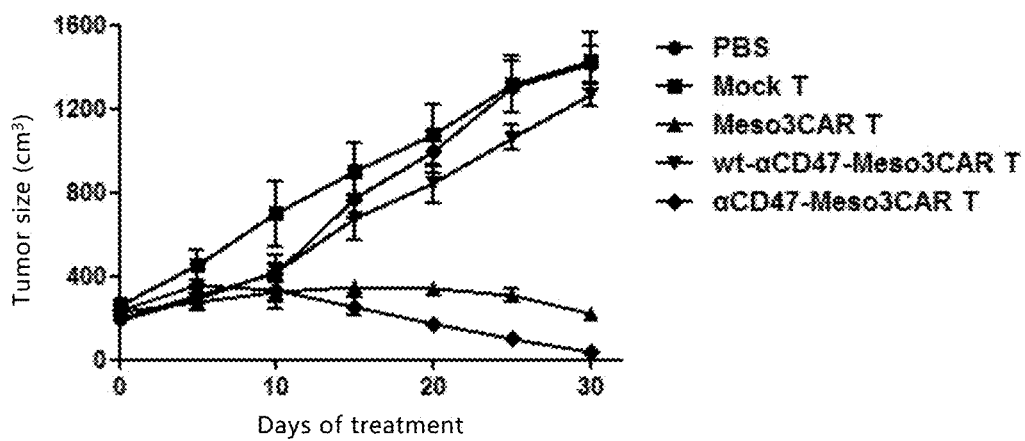
FIG. 41: Anti-tumor effect of αCD47-Meso3CAR T cell in vivo.

The details are shown in FIG. 41.

We claim:

1. A T cell expressing an antibody, or comprising a coding sequence of the antibody or an expression vector thereof, or with an expression cassette comprising a nucleic acid encoding the antibody integrated into the genome of the T cell, wherein:
the antibody comprises, an antigen binding sequence, a mutant Fc segment and optionally a signal peptide, wherein the mutant Fc segment is a mutant IgG4 Fc segment consists of the amino acid sequence shown in amino acid residues 269-497 of SEQ ID NO: 1; and
the T cell is a CAR-T cell expressing a chimeric antigen receptor, wherein the chimeric antigen receptor contains, an antigen recognition region, a hinge region of CD8 or IgG4 Fc CH2CH3, a transmembrane region of CD8 or CD28, an intracellular co-stimulatory signal domain of CD28 or 4-1BB, an intracellular signal domain of CD3ζ, and optionally a signal peptide.

2. The T cell according to claim 1, wherein the coding sequence of the mutant IgG4 Fc segment is as shown in nucleotide residues 805-1491 of SEQ ID NO: 2.

3. The T cell according to claim 1, wherein:
the signal peptide is a light chain signal peptide consists of the amino acid sequence shown in amino acid residues 1-20 of SEQ ID NO: 1 or its coding sequence shown in nucleotide residues 1-60 of SEQ ID NO: 2; and/or
the antigen binding sequence is derived from an antibody or an antigen-binding fragment thereof that specifically binds to the antigen, or from a ligand of a protein that functions in a tumor microenvironment or a fragment thereof that binds to the protein.

4. The T cell according to claim 3, wherein the antibody from which the antigen binding sequence is derived is a single-chain antibody, or is an agonistic antibody selected from antibodies directed against one or more of the following antigens: CD28, CD137, CD134, CD40, CD40L, ICOS, HVEM, CD2, CD27, CD30, GITR, LIGHT, DR3, SLAM, CD226, CD80 and CD86, or is an inhibitory antibody selected from antibodies directed against one or more of the following antigens: PD-1, CTLA4, PDL1, PDL2, PDL3, TIM3, LAG3, CD47, BTLA, TIGIT, CD160, LAIR1, B7-H1, B7-1, VSIR and CD244.

5. The T cell according to claim 3, wherein:
the antibody from which the antigen binding sequence is derived is an agonistic antibody which is a CD40 single-chain antibody; wherein the amino acid sequence of the light chain variable region of the CD40 single-chain antibody is as shown in amino acid residues 21-146 of SEQ ID NO: 1, and/or the amino acid sequence of the heavy chain variable region of the CD40 single-chain antibody is as shown in amino acid residues 161-268 of SEQ ID NO: 1, or the amino acid sequence of the CD40 single-chain antibody is as shown in amino acid residues 21-268 of SEQ ID NO: 1 or as shown in SEQ ID NO: 1; or the coding sequence of the light chain variable region of the CD40 single-chain antibody is as shown in nucleotide residues 60-438 of SEQ ID NO: 2, and/or the coding sequence of the heavy chain variable region thereof is as shown in nucleotide residues 481-804 of SEQ ID NO: 2, or the coding sequence of the CD40 single-chain antibody is as shown in nucleotide residues 60-1491 of SEQ ID NO: 2, or as shown in SEQ ID NO: 2;
the antibody from which the antigen binding sequence is derived is an inhibitory antibody which is a PD-1 single-chain antibody; wherein the amino acid sequence of the light chain variable region of the PD-1 single-chain antibody is as shown in amino acid residues 21-131 of SEQ ID NO: 3, and/or the amino acid sequence of the heavy chain variable region of the PD-1single-chain antibody is as shown in amino acid residues 147-266 of SEQ ID NO: 3, or the amino acid sequence of the PD-1 single-chain antibody is as shown in amino acid residues 21-266 of SEQ ID NO: 3 or as shown in SEQ ID NO:3; or the coding sequence of the light chain variable region of the PD-1 single-chain antibody is as shown in nucleotide residues 60-393 of SEQ ID NO: 4, and/or the coding sequence of the heavy chain variable region thereof is as shown in nucleotide residues 439-798 of SEQ ID NO: 4, or the coding sequence of the PD-1 single-chain antibody is as shown in nucleotide residues 60-1491 of SEQ ID NO: 4, or as shown in SEQ ID NO: 4; and/or
the ligand is a CD47 ligand with its amino acid sequence shown in amino acid residues 21-138 of SEQ ID NO: 5 or as shown in SEQ ID NO:5; or the coding sequence of the CD47 ligand is as shown in nucleotide residues 60-414 of SEQ ID NO: 6 or as shown in SEQ ID NO:6.

6. The T cell according to claim 1, wherein the T cell further comprises an expression cassette comprising a nucleic acid encoding the chimeric antigen receptor, and both the expression cassette comprising the nucleic acid encoding the antibody and the expression cassette comprising the nucleic acid encoding the chimeric antigen receptor are integrated into the genome of the T cell.

7. The T cell according to claim 6, wherein the chimeric antigen receptor recognizes, targets, or specifically binds to one or more of the following antigens:
CD19, CD20, CEA, GD2, FR, PSMA, PMEL, CA9, CD171/L1-CAM, IL-13Rα2, MART-1, ERBB2, NY-ESO-1, MAGE family proteins, BAGE family proteins, GAGE family proteins, AFP, MUC1, CD22, CD23, CD30, CD33, CD44v7/8, CD70, VEGFR1, VEGFR2, IL-11Rα, EGP-2, EGP-40, FBP, GD3, PSCA, FSA, PSA, HMGA2, fetal acetylcholine receptor, LeY, EpCAM, MSLN, IGFR1, EGFR, EGFRVIII, ERBB3, ERBB4, CA125, CA15-3, CA19-9, CA72-4, CA242, CA50, CYFRA21-1, SCC, AFU, EBV-VCA, POA, B2-MG and PROGRP.

8. The T cell according to claim 1, wherein in the chimeric antigen receptor:
the amino acid sequence of the signal peptide is as shown in amino acid residues 1-21 of SEQ ID NO: 7, or amino acid residues 1-22 of SEQ ID NO: 9, or amino acid residues 1-20 of SEQ ID NO: 11; or the coding sequence of the signal peptide is as shown in the nucleotide residues 1-63 of SEQ ID NO: 8, or the nucleotide residues 1-66 of SEQ ID NO: 10, or the nucleotide residues 1-60 of SEQ ID NO: 12;
the antigen recognition region is a single-chain antibody that recognizes, targets, or specifically binds to CD19, mesothelin, EGFR, or mucin, or consists of an amino acid sequence that recognizes, targets, or specifically binds to ErbB receptor family;
the amino acid sequence of the hinge region is as shown in amino acid residues 264-308 of SEQ ID NO: 7, or amino acid residues 273-500 of SEQ ID NO: 9, or amino acid residues 264-318 of SEQ ID NO: 17; or the coding sequence of the hinge region is as shown in nucleotide residues 790-924 of SEQ ID NO: 8, or nucleotide residues 817-1500 of SEQ ID NO: 10, or nucleotide residues 790-954 of SEQ ID NO: 18;

the amino acid sequence of the transmembrane region is as shown in amino acid residues 309-332 of SEQ ID NO: 7, or amino acid residues 501-528 of SEQ ID NO: 9, or amino acid residues 319-344 of SEQ ID NO: 17; or the coding sequence of the transmembrane region is as shown in the nucleotide residues 925-996 of SEQ ID NO: 8, or the nucleotide residues 1501-1584 of SEQ ID NO: 10, or the nucleotide residues 955-1032 of SEQ ID NO: 18;

the amino acid sequence of the intracellular co-stimulatory signal domain is as shown in amino acid residues 333-374 of SEQ ID NO: 7, or amino acid residues 529-569 of SEQ ID NO: 9; or the coding sequence of the intracellular co-stimulatory signal domain is as shown in the nucleotide residues 997-1122 of SEQ ID NO: 8, or the nucleotide residues 1585-1707 of SEQ ID NO: 10; and/or the amino acid sequence of the intracellular signal domain is as shown in amino acid residues 375-486 of SEQ ID NO: 7; or the coding sequence of the intracellular signal domain is as shown in the nucleotide residues 1123-1458 of SEQ ID NO: 8.

9. The T cell according to claim 8, wherein:

the amino acid sequence of the light chain variable region of the single-chain antibody that recognizes, targets or specifically binds to CD19 is as shown in amino acid residues 22-128 of SEQ ID NO: 7, and/or the amino acid sequence of the heavy chain variable region thereof may be as shown in amino acid residues 144-263 of SEQ ID NO: 7;or the amino acid sequence of the single-chain antibody is as shown in amino acid residues 22-263 of SEQ ID NO: 7;

the single-chain antibody that recognizes, targets or specifically binds to mesothelin antigen is a single-chain antibody directed against Region I or III of mesothelin; wherein the amino acid sequence of the light chain variable region of the anti-mesothelin Region III single-chain antibody is as shown in amino acid residues 23-146 of SEQ ID NO: 9, and/or the amino acid sequence of the heavy chain variable region of the anti-mesothelin Region III single-chain antibody is as shown in amino acid residues 162-272 of SEQ ID NO: 9;or the amino acid sequence of the single chain antibody that recognizes, targets or specifically binds to mesothelin antigen is as shown in amino acid residues 23-272 of SEQ ID NO:9;

the antigen recognition region that recognizes, targets or specifically binds to the ErbB receptor family contains a fusion protein of natural TIE and Herin; wherein the TIE consists of 7 amino acids at the N-terminus of human transcription growth factor a (TGFa) and 48 amino acids at the C-terminus of epidermal growth factor (EGF), or the TIE consists of an amino acid sequence as shown in amino acid residues 23-77 of SEQ ID NO: 13; the Herin is the 79 amino acids encoded by intron 8 in Herstatin; or the amino acid sequence of Herin is as shown in amino acid residues 93-171 of SEQ ID NO: 13, and/or the antigen recognition region is as shown in amino acid residues 23-171 of SEQ ID NO: 13;

the amino acid sequence of the light chain variable region and the amino acid sequence of the heavy chain variable region of the single-chain antibody that recognizes, targets or specifically binds to mucin antigen are derived from an antibody against the amino acid sequence of the membrane-proximal end of Muc1 or against an amino acid sequence shown in SEQ ID NO: 24; or the amino acid sequence of the light chain variable region of the single chain antibody is as shown in amino acid residues 23-133 of SEQ ID NO: 15, and/or the amino acid sequence of the heavy chain variable region is as shown in amino acid residues 149-269 of SEQ ID NO: 15;

or the amino acid sequence of the single chain antibody is as shown in amino acid residues 23-269 of SEQ ID NO: 15; and/or the antigen recognition region that recognizes, targets, or specifically binds to EGFR is a single chain antibody formed by the light chain variable region and the heavy chain variable region of an antibody specific for EGFR, or is a single chain antibody with its amino acid sequence of the light chain variable region shown in amino acid residues 23-129 of SEQ ID NO: 17 and/or its amino acid sequence of the heavy chain variable region shown in amino acid residues 145-263 of SEQ ID NO: 17, or is a single chain antibody with its amino acid sequence shown in amino acid residues 23-263 of SEQ ID NO: 17.

10. The T cell according to claim 9, wherein the chimeric antigen receptor contains, in the order from the N-terminus to the C-terminus, an optional signal peptide sequence, an antigen recognition region, the hinge region of CD8α or the hinge region of IgG4 CH2CH3, the transmembrane region of CD8 or the transmembrane region of CD28, the intracellular domain of 4-1BB or CD28, and the intracellular signal domain of CD3ζ.

11. The T cell according to claim 10, wherein the chimeric antigen receptor is selected from the group consisting of:
(1) a chimeric antigen receptor targeting CD19, with the amino acid sequence thereof being as shown in amino acid residues 22-486 of SEQ ID NO: 7, or as shown in SEQ ID NO: 7, and the coding sequence thereof being as shown in nucleotide residues 64-1458 of SEQ ID NO: 8, or as shown in SEQ ID NO: 8;
(2) a chimeric antigen receptor targeting mesothelin, with the amino acid sequence thereof being as shown in amino acid residues 23-681 of SEQ ID NO: 9, or as shown in SEQ ID NO: 9, the coding sequence thereof being as shown in nucleotide residues 67-2043 of SEQ ID NO: 10, or as shown in SEQ ID NO: 10, or the amino acid sequence thereof being as shown in amino acid residues 21-679 of SEQ ID NO: 11, or as shown in SEQ ID NO: 11, the coding sequence thereof being as shown in nucleotide residues 61-2037 of SEQ ID NO: 12, or as shown in SEQ ID NO: 12;
(3) a chimeric antigen receptor targeting ErbB family, with the amino acid sequence thereof being as shown in amino acid residues 23-580 of SEQ ID NO: 13, or as shown in SEQ ID NO: 13, and the coding sequence thereof being as shown in nucleotide residues 67-1740 of SEQ ID NO: 14, or as shown in SEQ ID NO: 14;
(4) a chimeric antigen receptor targeting mucin, with the amino acid sequence thereof being as shown in amino acid residues 23-678 of SEQ ID NO: 15, or as shown in SEQ ID NO: 15, and the coding sequence thereof being as shown in nucleotide residues 67-2034 of SEQ ID NO: 16,or as shown in SEQ ID NO: 16; and
(5) a chimeric antigen receptor targeting EGFR, with the amino acid sequence thereof being as shown in amino acid residues 23-497 of SEQ ID NO: 17, or as shown in SEQ ID NO: 17, or the coding sequence thereof being as shown in nucleotide residues 67-1491 of SEQ ID NO: 18, or as shown in SEQ ID NO: 18.

12. A pharmaceutical composition, comprising the T cell according to claim 1 or comprising the T cell and the antibody expressed by the T cell.

13. A method for preparing the T cell according to claim 6, wherein the method comprises a step of transfecting the T cell with the following vectors:
   (1) the vector that is for transferring the expression cassette of the chimeric antigen receptor into the genome of the T cell and contains a transposase coding sequence, and
   (2) the vector that is for transferring the expression cassette of the antibody into the genome of the T cell and does not contain a transposase coding sequence;
   wherein the mass ratio of the vectors of (1) to (2) is 1-7:1-7.

* * * * *